United States Patent
Measamer et al.

(10) Patent No.: US 10,188,386 B2
(45) Date of Patent: Jan. 29, 2019

(54) SURGICAL STAPLER WITH ANVIL STATE INDICATOR

(71) Applicant: Ethicon Endo-Surgery, LLC, Guaynabo, PR (US)

(72) Inventors: John P. Measamer, Cincinnati, OH (US); Christopher C. Miller, Loveland, OH (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 477 days.

(21) Appl. No.: 14/751,517

(22) Filed: Jun. 26, 2015

(65) Prior Publication Data

US 2016/0374671 A1     Dec. 29, 2016

(51) Int. Cl.
| | |
|---|---|
| *A61B 17/04* | (2006.01) |
| *A61B 17/10* | (2006.01) |
| *A61B 17/068* | (2006.01) |
| *A61B 17/115* | (2006.01) |
| *A61B 17/00* | (2006.01) |

(Continued)

(52) U.S. Cl.
CPC ........ *A61B 17/068* (2013.01); *A61B 17/1155* (2013.01); *A61B 2017/00017* (2013.01); *A61B 2017/00398* (2013.01); *A61B 2017/2943* (2013.01); *A61B 2090/061* (2016.02); *A61B 2090/062* (2016.02); *A61B 2090/064* (2016.02); *A61B 2090/0811* (2016.02)

(58) Field of Classification Search
CPC .... A61B 2017/2913; A61B 2017/2933; A61B 17/068; A61B 17/105
USPC .................... 227/175.1–182.1; 606/139, 219
See application file for complete search history.

(56) References Cited

U.S. PATENT DOCUMENTS

| | | | |
|---|---|---|---|
| 4,606,344 A | * | 8/1986 | Di Giovanni ........ A61B 17/072 112/169 |
| 5,205,459 A | | 4/1993 | Brinkerhoff et al. |

(Continued)

FOREIGN PATENT DOCUMENTS

| | | |
|---|---|---|
| EP | 2792308 | 10/2014 |
| WO | WO 2010/045533 | 4/2010 |

OTHER PUBLICATIONS

International Search Report and Written Opinion dated Dec. 29, 2016 re Apptication No. PCT/US16/38939.

(Continued)

*Primary Examiner* — Robert Long
(74) *Attorney, Agent, or Firm* — Frost Brown Todd LLC

(57) ABSTRACT

A surgical instrument includes a stapling head assembly, an anvil, an anvil adjustment assembly, and an indicator assembly. The anvil is configured to couple with the stapling head assembly. The anvil adjustment assembly includes a translating member, which is operable to translate relative to the body to thereby adjust a gap distance between the anvil and a distal surface of the stapling head assembly. The indicator assembly includes a first member and a second member. The first member is configured to translate in response to translation of the translating member relative to the body. The second member is configured to remain stationary relative to the body. The indicator assembly is configured to provide feedback indicating whether the gap distance is sized to release tissue from between the anvil and the distal surface based on positioning of the first member in relation to the second member.

19 Claims, 49 Drawing Sheets

(51) Int. Cl.
*A61B 17/29* (2006.01)
*A61B 90/00* (2016.01)

(56) References Cited

U.S. PATENT DOCUMENTS

| | | | |
|---|---|---|---|
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,443,198 A * | 8/1995 | Viola | A61B 17/072 227/175.1 |
| 5,533,661 A | 7/1996 | Main et al. | |
| 6,050,472 A | 4/2000 | Shibata | |
| 6,050,742 A | 4/2000 | Held et al. | |
| 6,945,444 B2 | 9/2005 | Gresham et al. | |
| 7,464,847 B2 | 12/2008 | Viola et al. | |
| 7,794,475 B2 | 9/2010 | Hess et al. | |
| 8,220,688 B2 | 7/2012 | Laurent et al. | |
| 8,408,439 B2 | 4/2013 | Huang et al. | |
| 8,453,914 B2 | 6/2013 | Laurent et al. | |
| 8,910,847 B2 | 12/2014 | Nalagatla et al. | |
| 9,161,803 B2 | 10/2015 | Yates et al. | |
| 9,186,148 B2 | 11/2015 | Felder et al. | |
| 9,220,505 B2 | 12/2015 | Vasudevan et al. | |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 9,532,783 B2 | 1/2017 | Swayze et al. | |
| 9,572,573 B2 | 2/2017 | Scheib et al. | |
| 9,597,081 B2 | 3/2017 | Swayze et al. | |
| 9,724,100 B2 | 8/2017 | Scheib et al. | |
| 2006/0273135 A1* | 12/2006 | Beetel | A61B 17/068 227/175.1 |
| 2007/0062017 A1* | 3/2007 | Dycus | A61B 18/1445 29/407.04 |
| 2007/0270784 A1* | 11/2007 | Smith | A61B 17/115 606/1 |
| 2008/0185419 A1* | 8/2008 | Smith | A61B 17/1114 227/179.1 |
| 2009/0057369 A1* | 3/2009 | Smith | A61B 17/07207 227/175.1 |
| 2010/0096431 A1* | 4/2010 | Smith | A61B 17/00 227/175.2 |
| 2010/0211053 A1* | 8/2010 | Ross | A61B 17/068 606/1 |
| 2011/0017801 A1* | 1/2011 | Zemlok | A61B 17/07207 227/175.1 |
| 2011/0155785 A1* | 6/2011 | Laurent | A61B 17/068 227/180.1 |
| 2013/0153631 A1* | 6/2013 | Vasudevan | A61B 17/115 227/175.2 |
| 2013/0168431 A1* | 7/2013 | Zemlok | A61B 17/07207 227/175.1 |
| 2014/0158747 A1 | 6/2014 | Measamer et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2016/0367248 A1* | 12/2016 | Baxter, III | A61B 17/068 |
| 2016/0374668 A1* | 12/2016 | Measamer | A61B 17/068 227/175.1 |
| 2017/0065209 A1* | 3/2017 | Radl | A61B 5/1076 |

OTHER PUBLICATIONS

European Search Report, Partial, dated Sep. 29, 2016 for Application No. EP 16176106.9, 7 pgs.
European Search Report, Extended, and Written Opinion dated Jan. 23, 2017 for Application No. EP 16176106.9, 11 pgs.

* cited by examiner

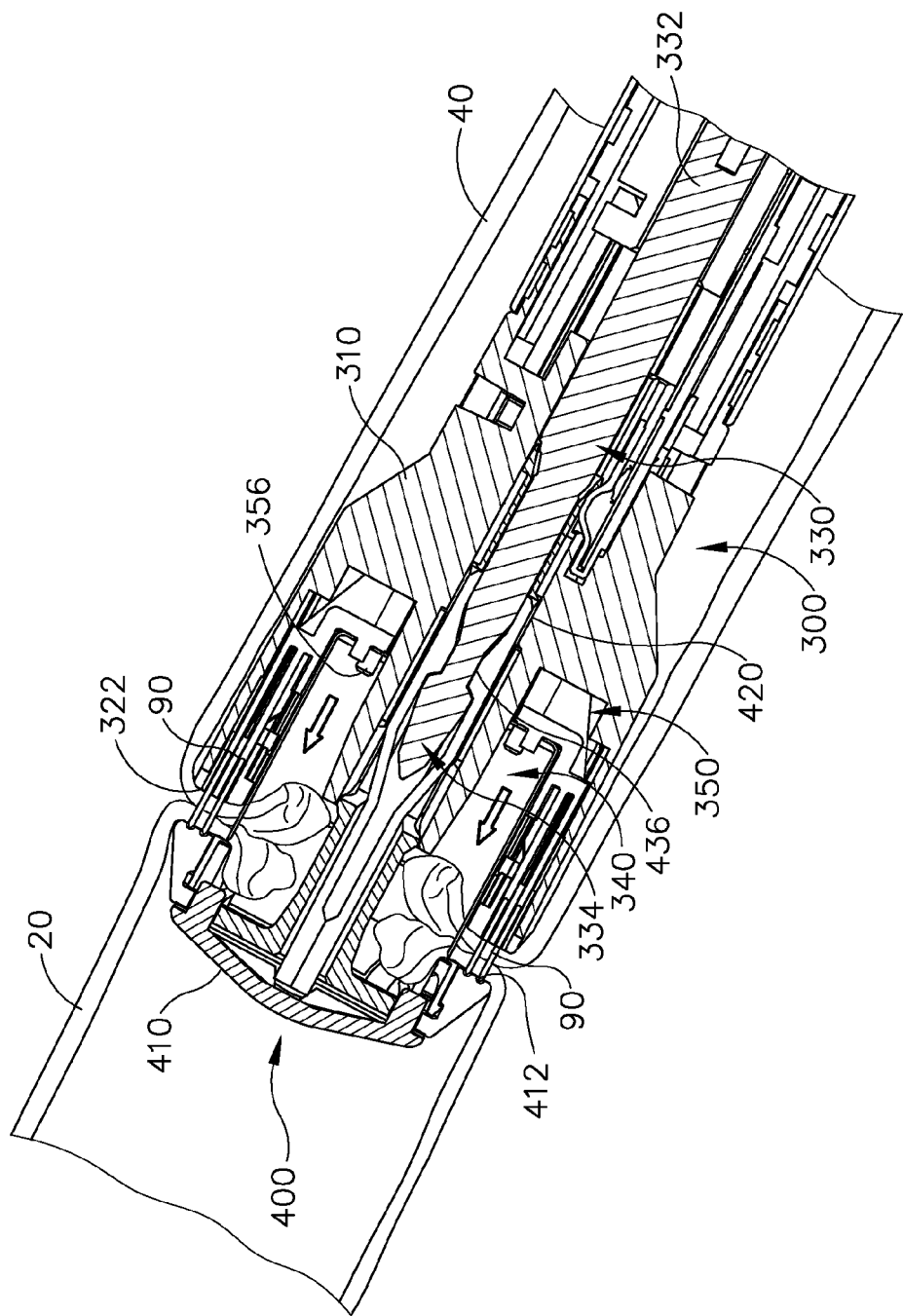

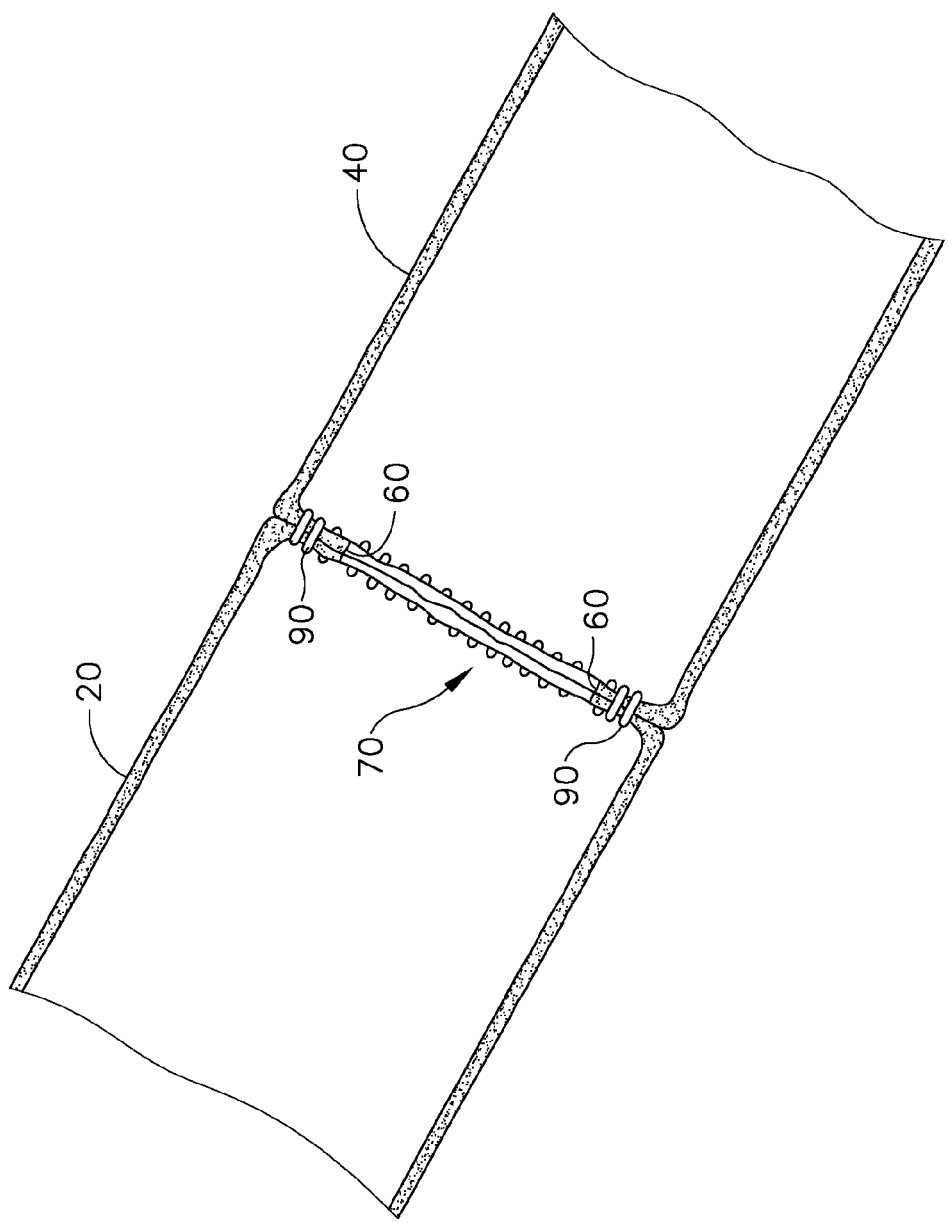

ism. Examples of circular staplers with motorized
SURGICAL STAPLER WITH ANVIL STATE INDICATOR

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015 now abandoned; U.S. Pub. No. 2015/0083773, entitled "Surgical Stapling Instrument with Drive Assembly Having Toggle Features," published Mar. 26, 2015, now U.S. Pat. No. 9,936,949, issued Apr. 20, 2018; U.S. Pub. No. 2015/0083774, entitled "Control Features for Motorized Surgical Stapling Instrument," published Mar. 26, 2015, now U.S. Pat. No. 9,907,552, issued Mar. 6, 2018; and U.S. Pub. No. 2015/0083775, entitled "Surgical Stapler with Rotary Cam Drive," published Mar. 26, 2015, now U.S. Pat. No. 9,713,469, issued Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue; and FIG. 21E depicts a cross-sectional side view of the first and second sections of the digestive tract of FIG. 21A joined together at an end-to-end anastomosis;

Figure 1:
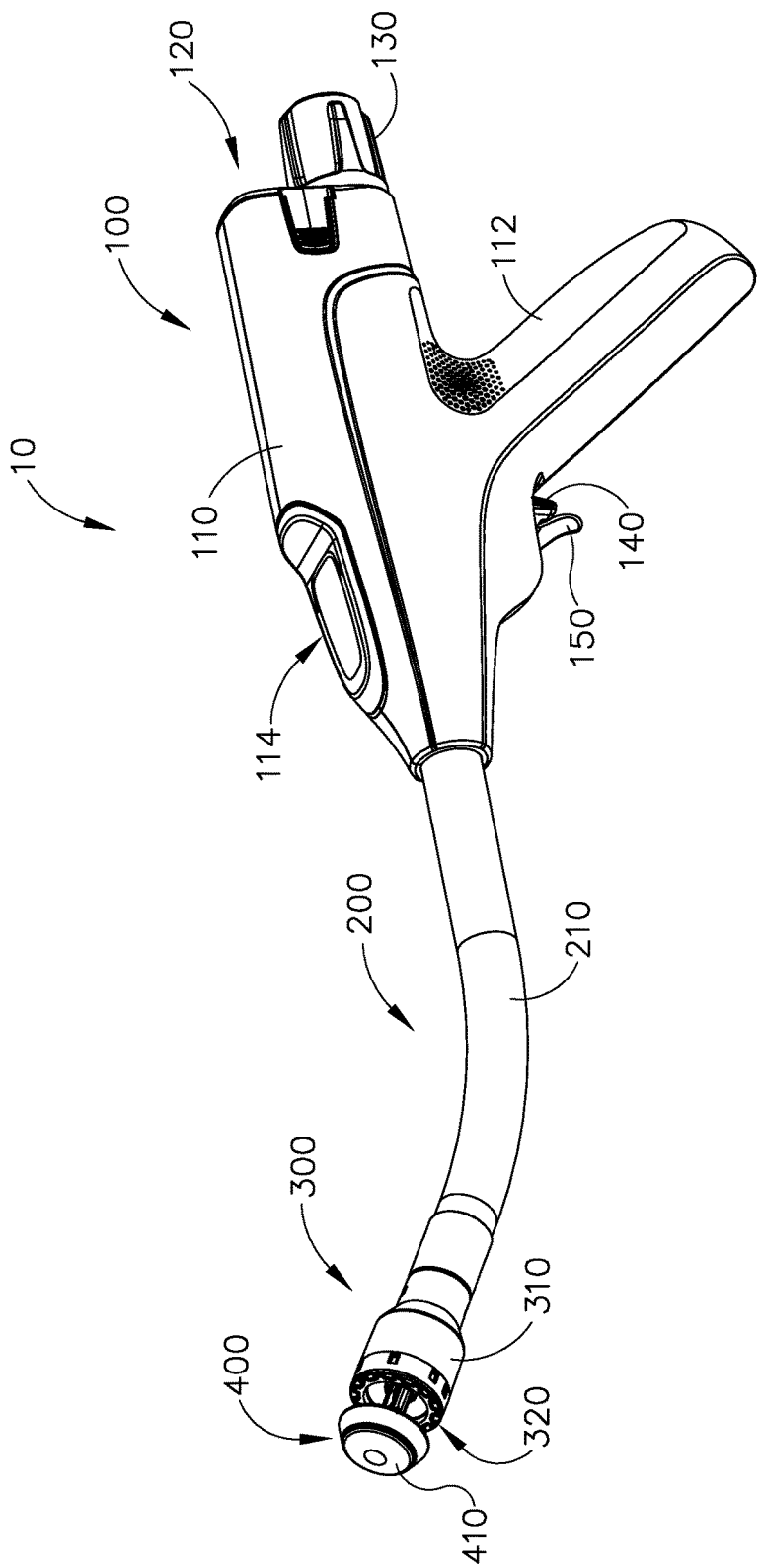
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
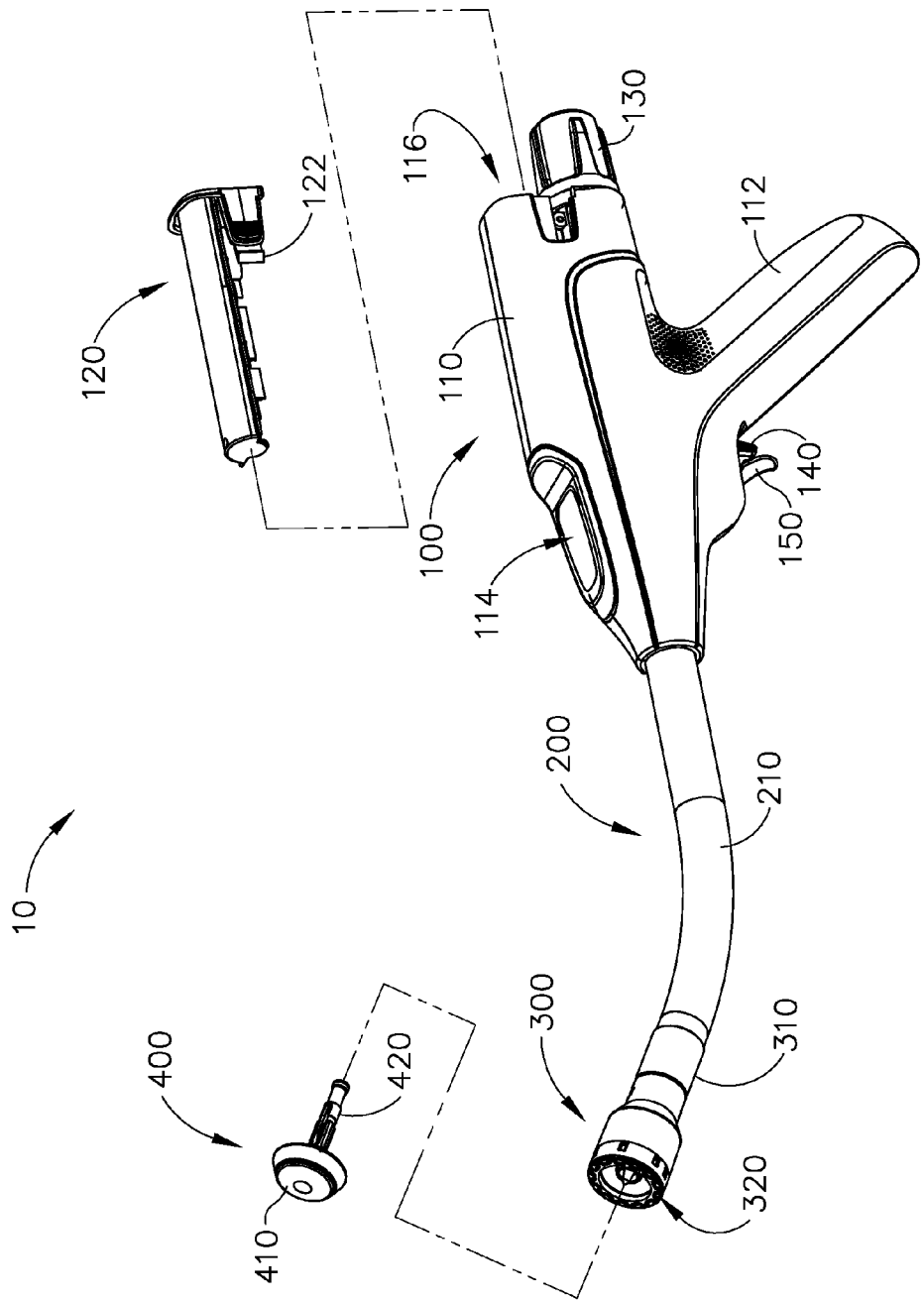
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A depicts (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
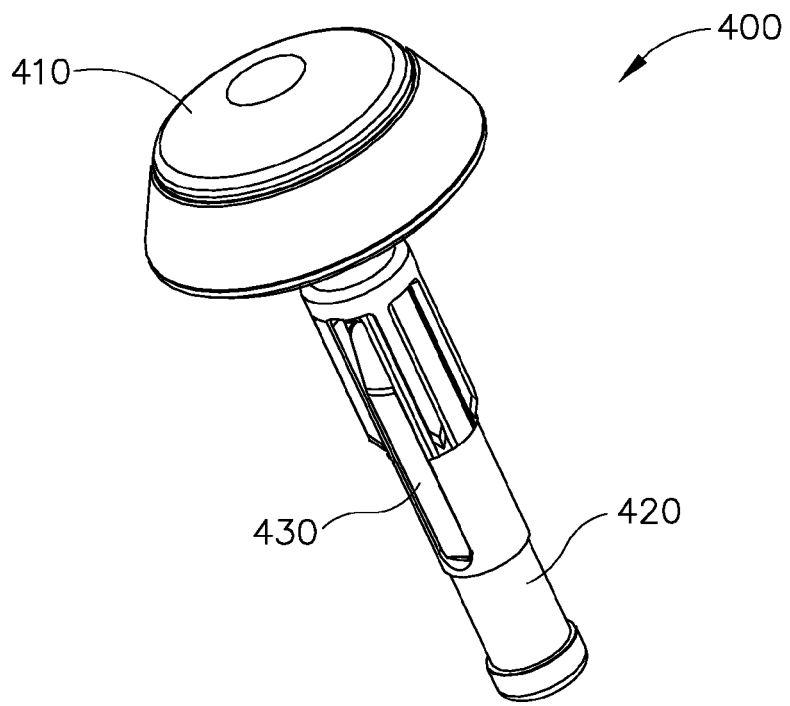
FIG. 3 depicts a perspective view of the anvil of the circular stapler of FIG. 1.
Figure 4:
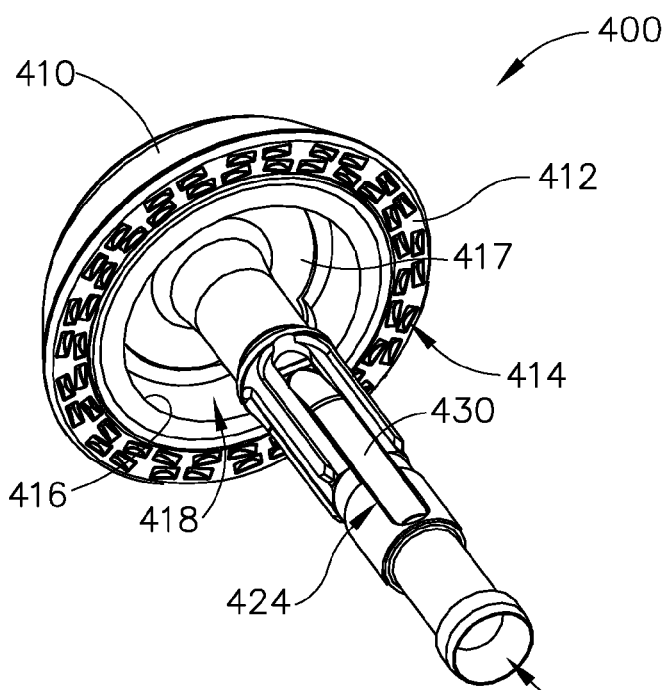
FIG. 4 depicts another perspective view of the anvil of FIG. 3.
Figure 5:
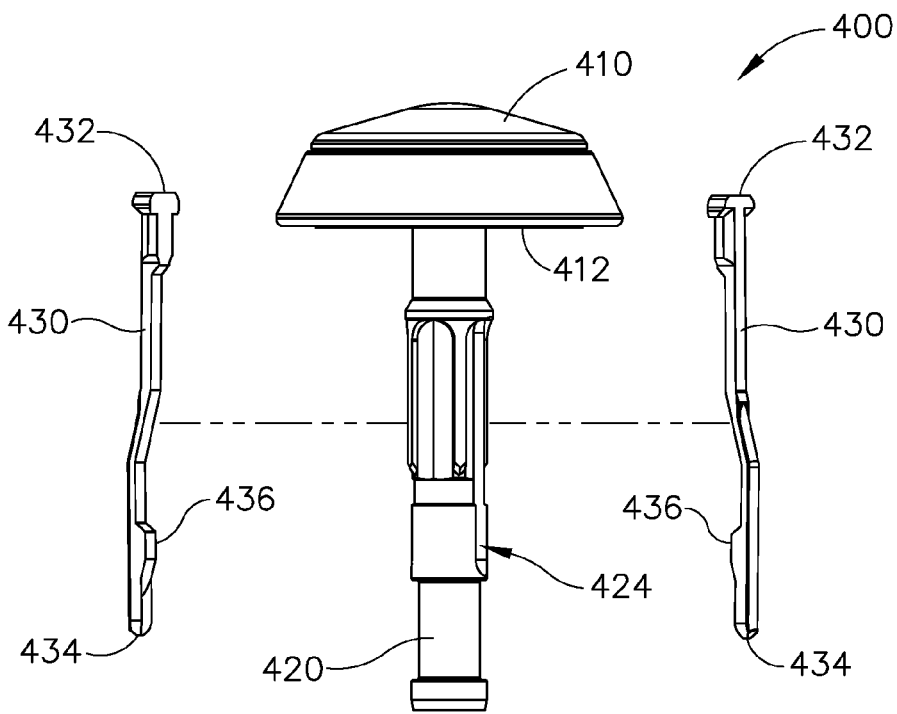
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pat. No. 8,910,847, the disclosures of which are incorporated by reference herein. Still other suitable configurations will be apparent to one of ordinary skill in the art in view of the teachings herein.

B. Exemplary Stapling Head Assembly

Figure 6:
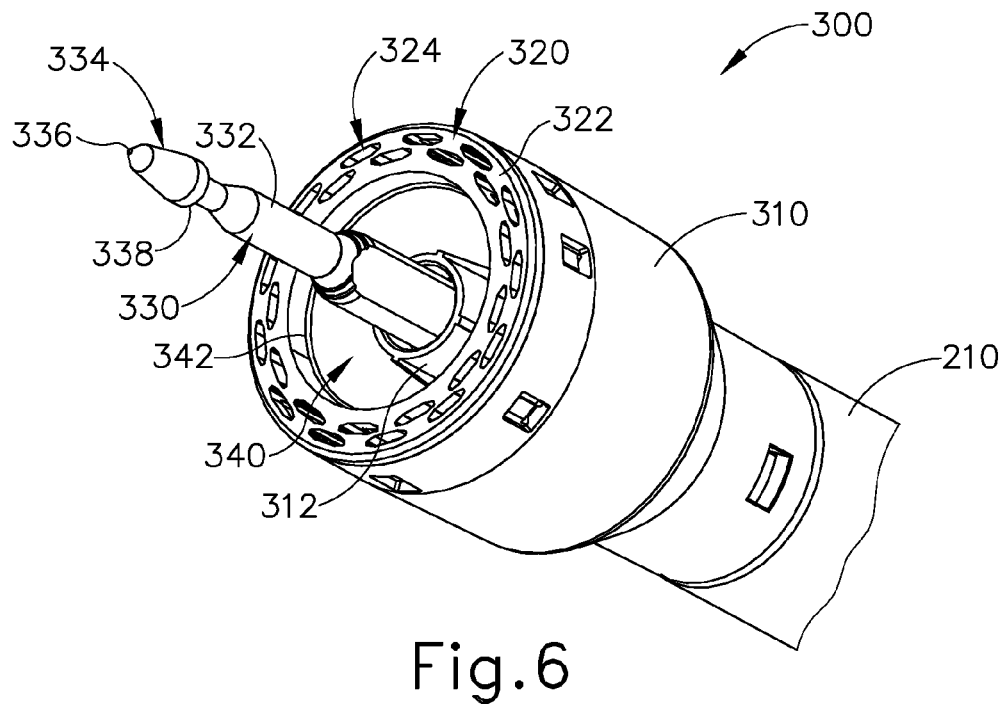
FIG. 6 depicts a perspective view of the stapling head assembly of the circular stapler of FIG. 1.
Figure 7:
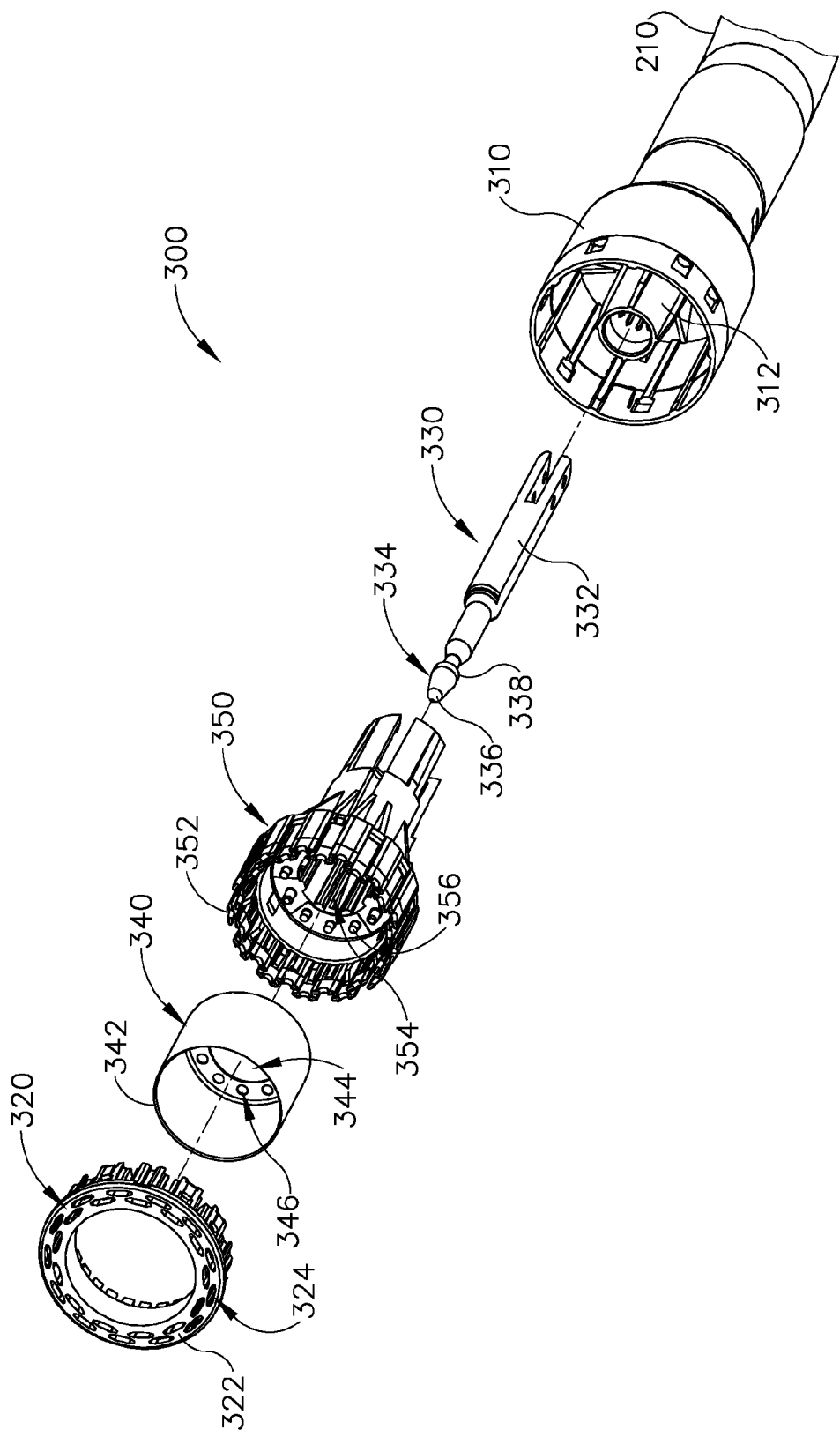
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pat. No. 8,910,847, the disclosures of which are incorporated by reference herein. Still other suitable configurations will be apparent to one of ordinary skill in the art in view of the teachings herein.

C. Exemplary Shaft Assembly

Figure 8:
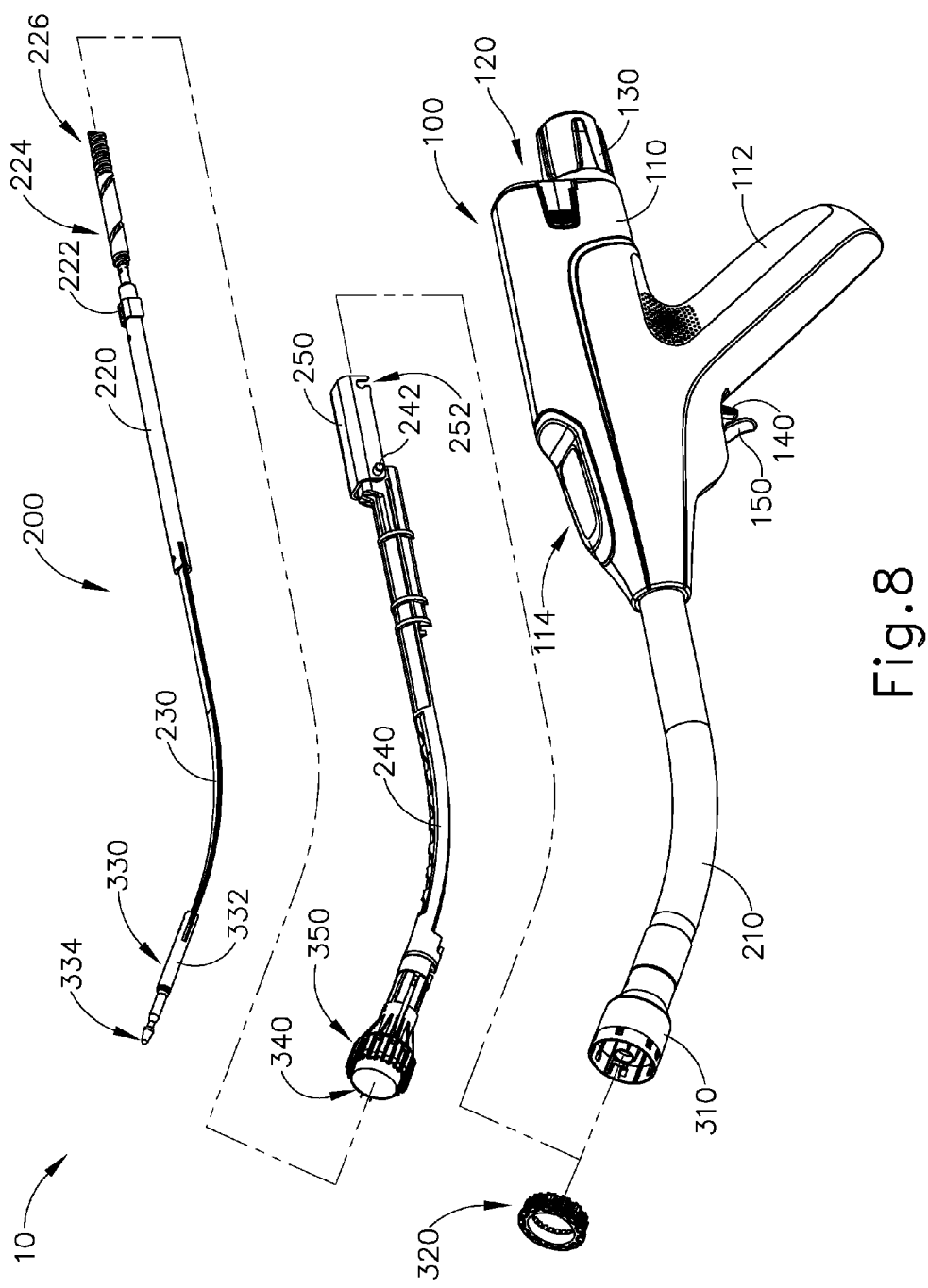
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pat. No. 8,910,847, the disclosures of which are incorporated by reference herein. Still other suitable configurations will be apparent to one of ordinary skill in the art in view of the teachings herein.

D. Exemplary Actuator Handle Assembly

Figure 9:
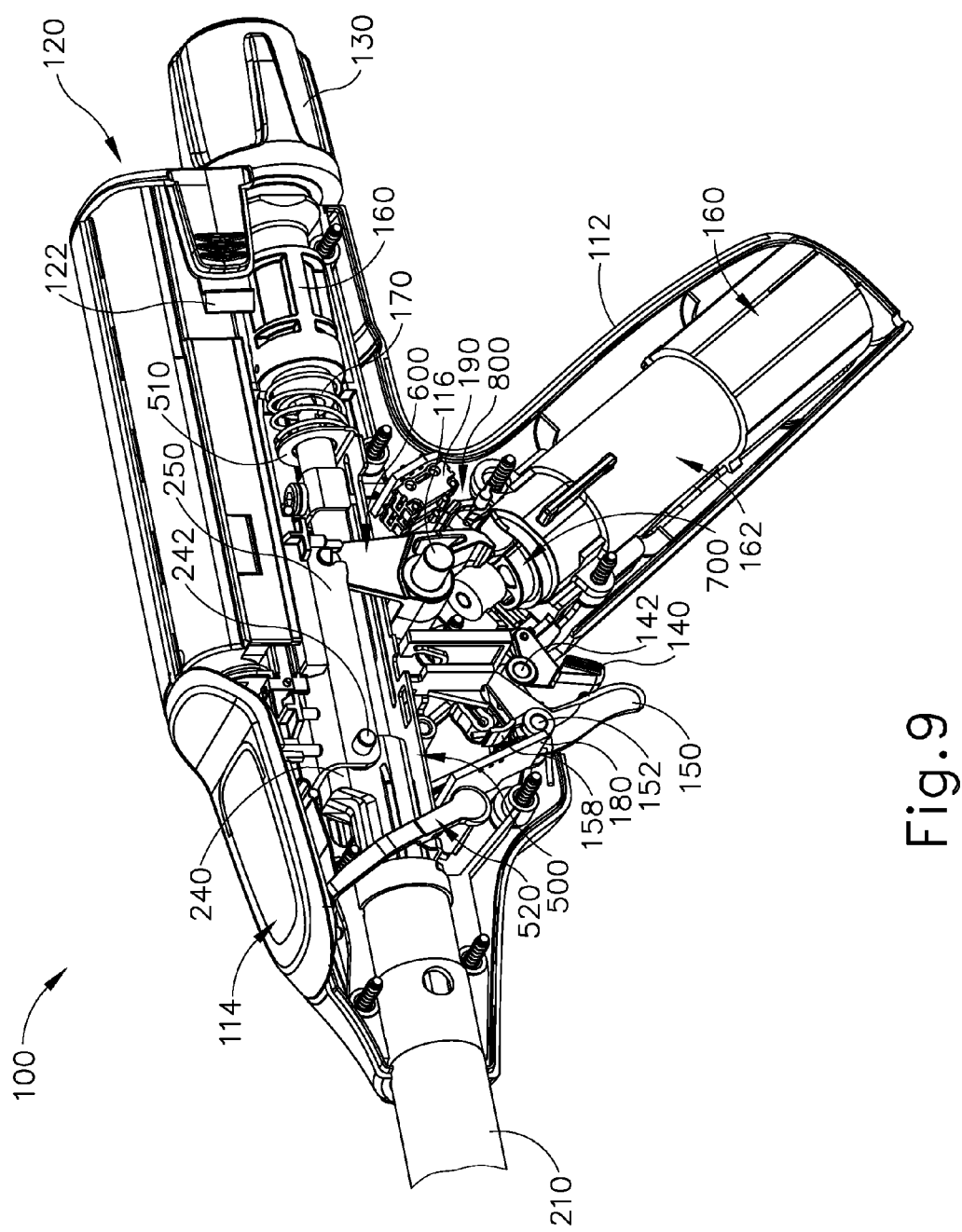
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
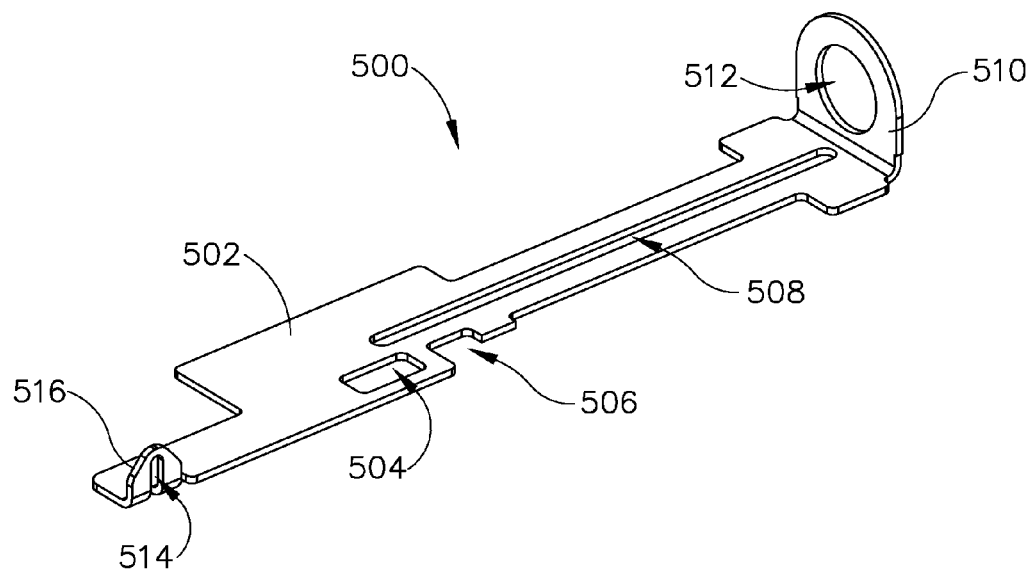
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
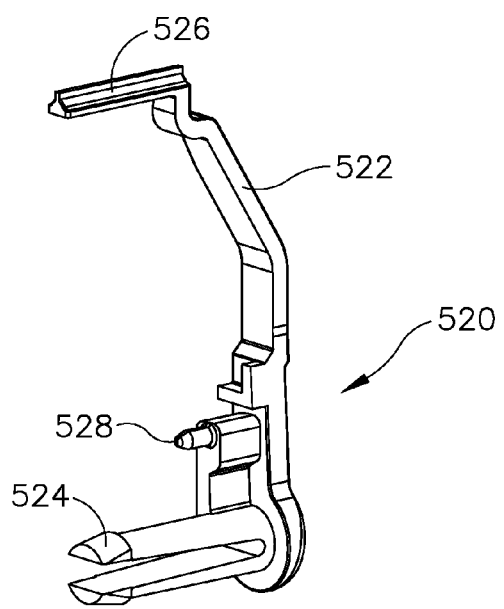
FIG. 11 depicts a perspective view of an indicator member of the handle assembly of FIG. 9.
Figure 12A:
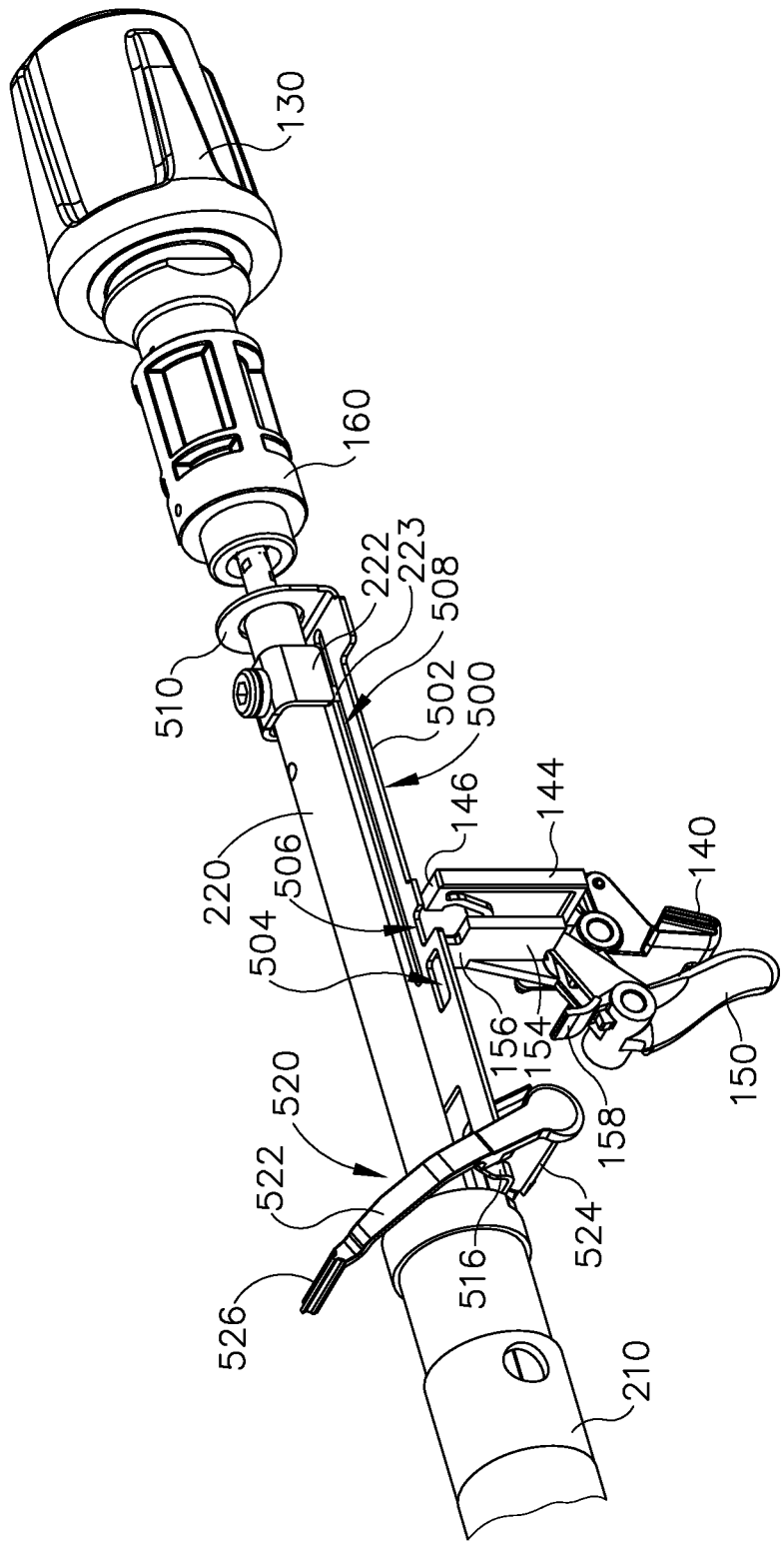
FIG. 12A depicts a perspective view of an anvil actuation assembly of the circular stapler of FIG. 1, with an actuation rod in a first position.
Figure 12B:
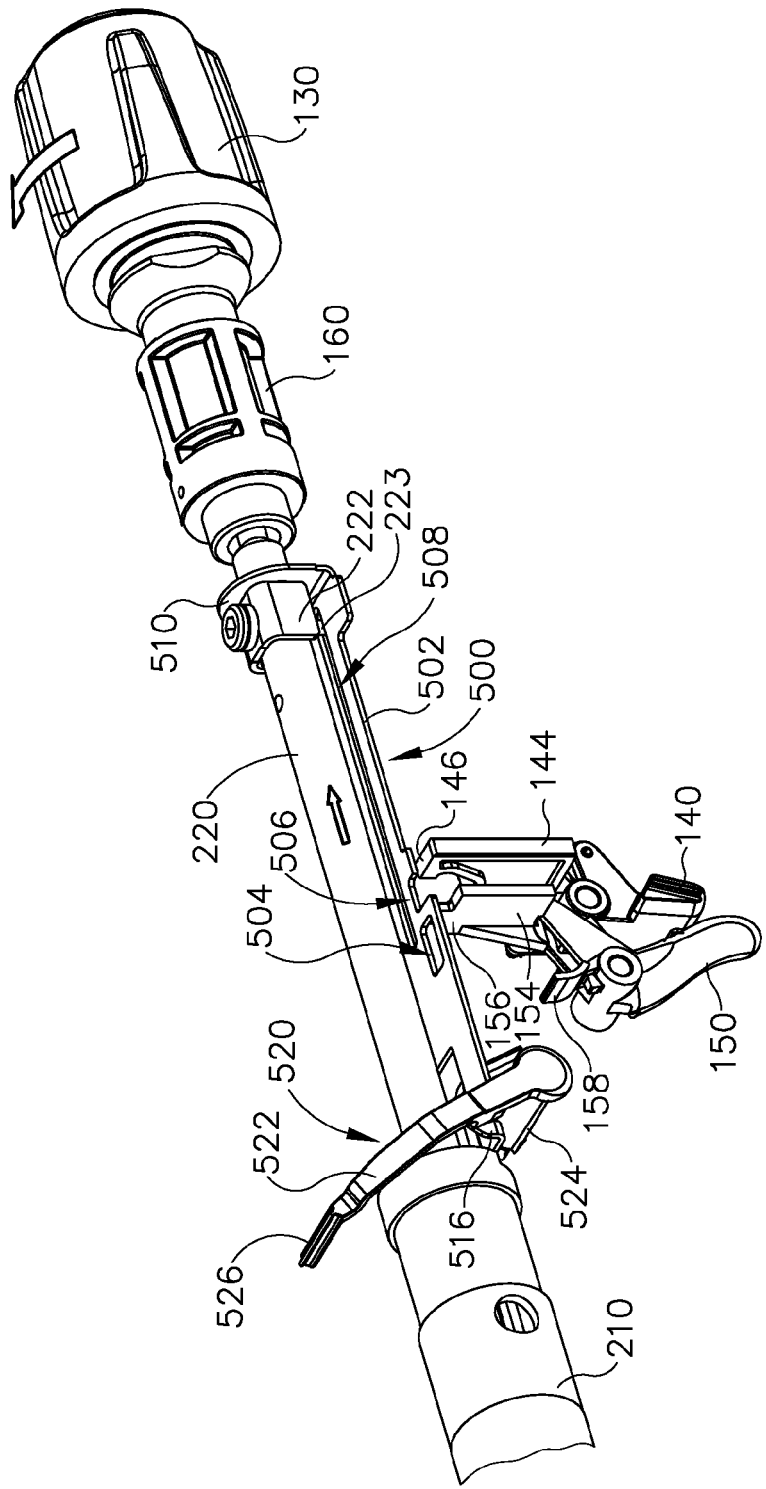
FIG. 12B depicts a perspective view of the anvil actuation assembly of FIG. 12A, with the actuation rod moved to a second position to engage the bracket of FIG. 10.
Figure 12C:
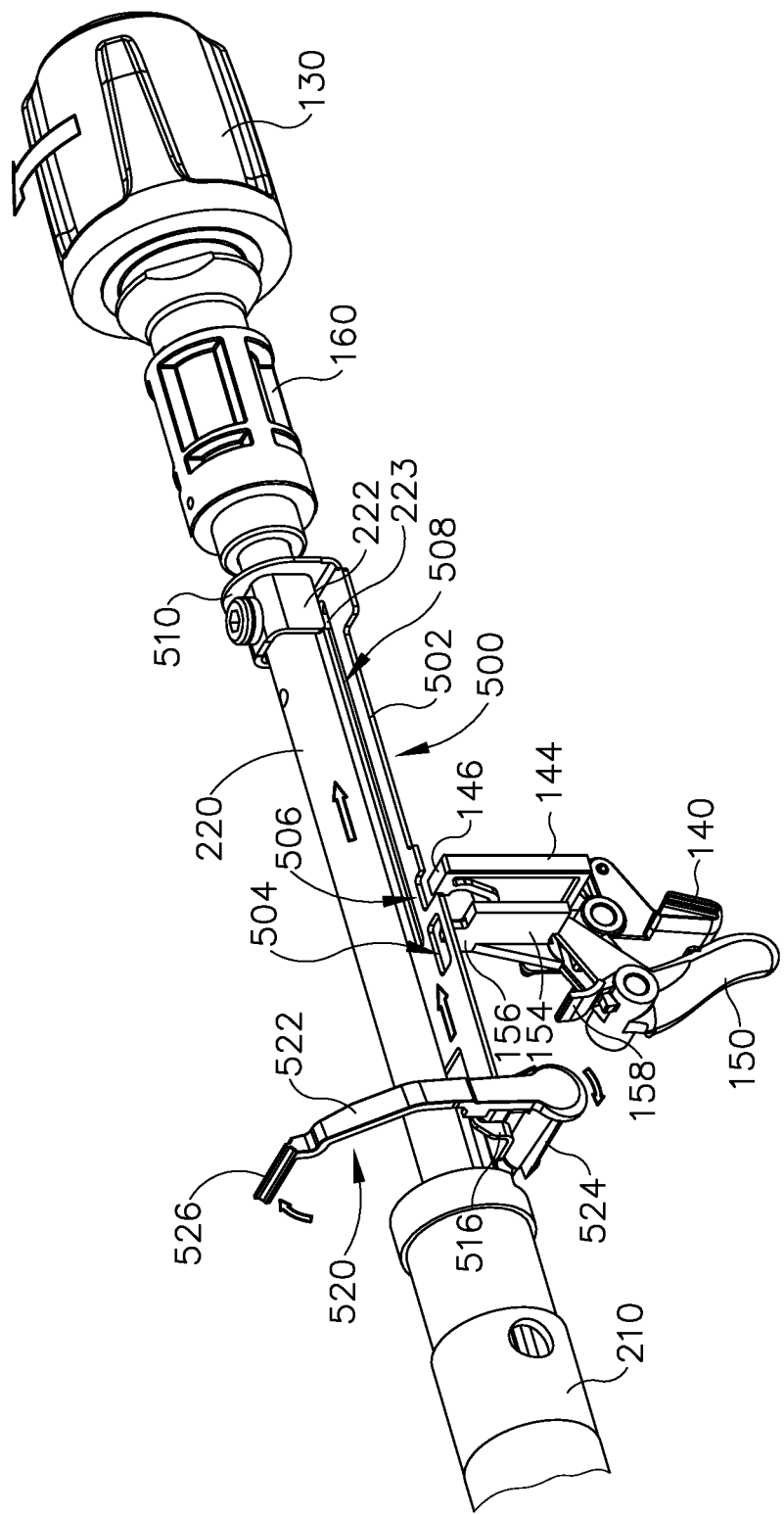
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG.

12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
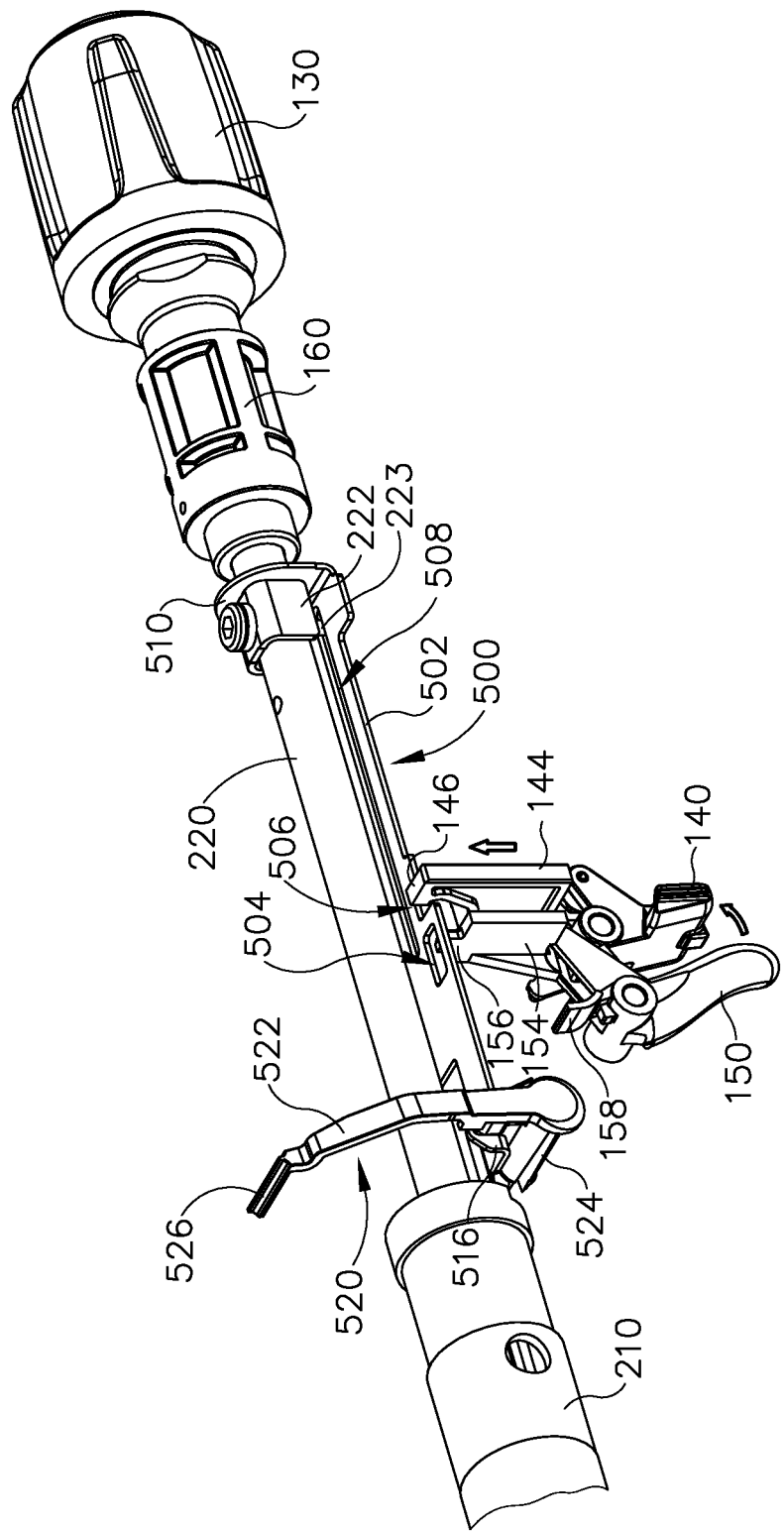
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
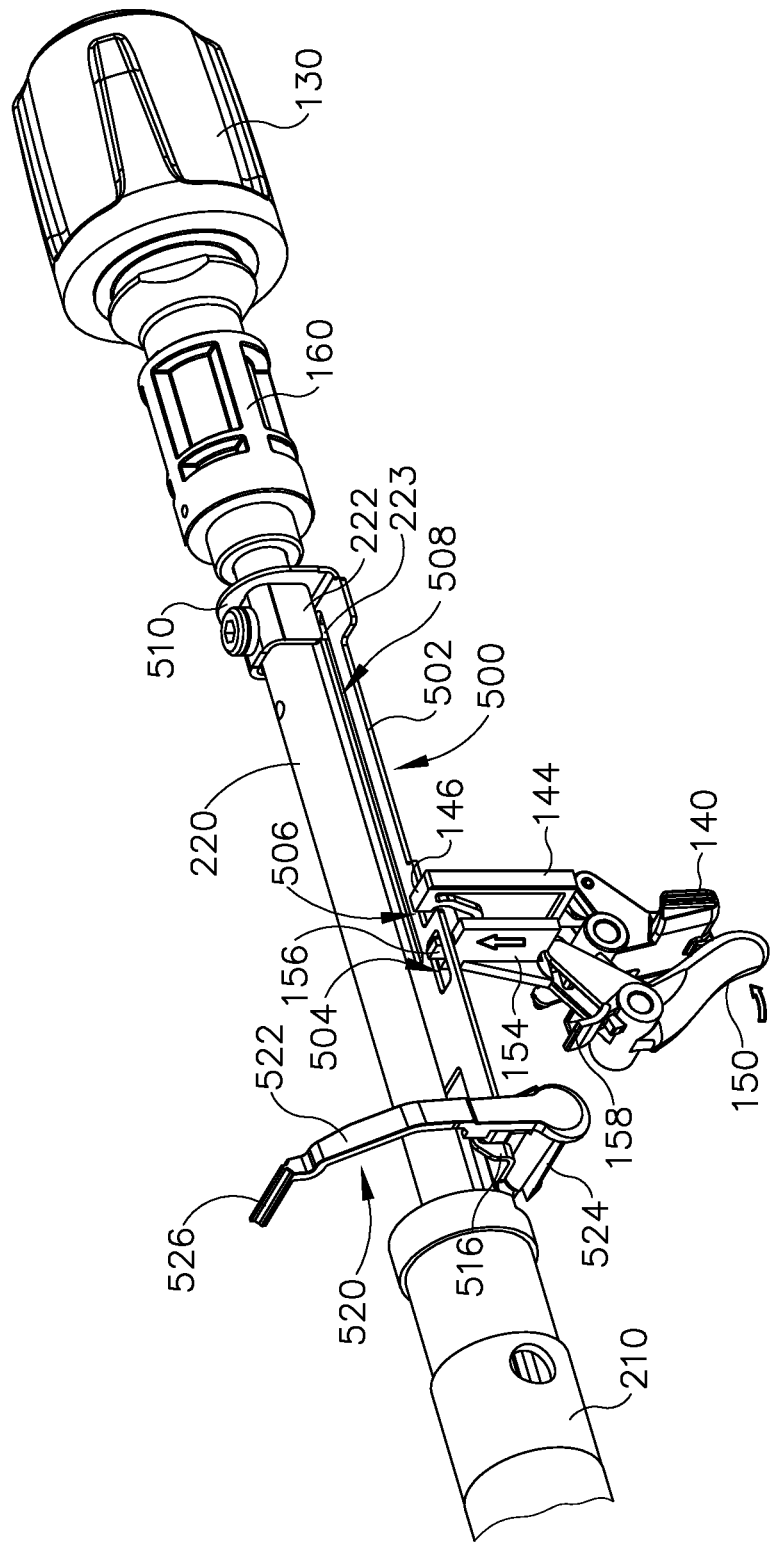
FIG. 12E depicts a perspective view of the anvil actuation assembly of FIG. 12A, with a firing trigger pivoted from a first position to a second position.
Figure 13:
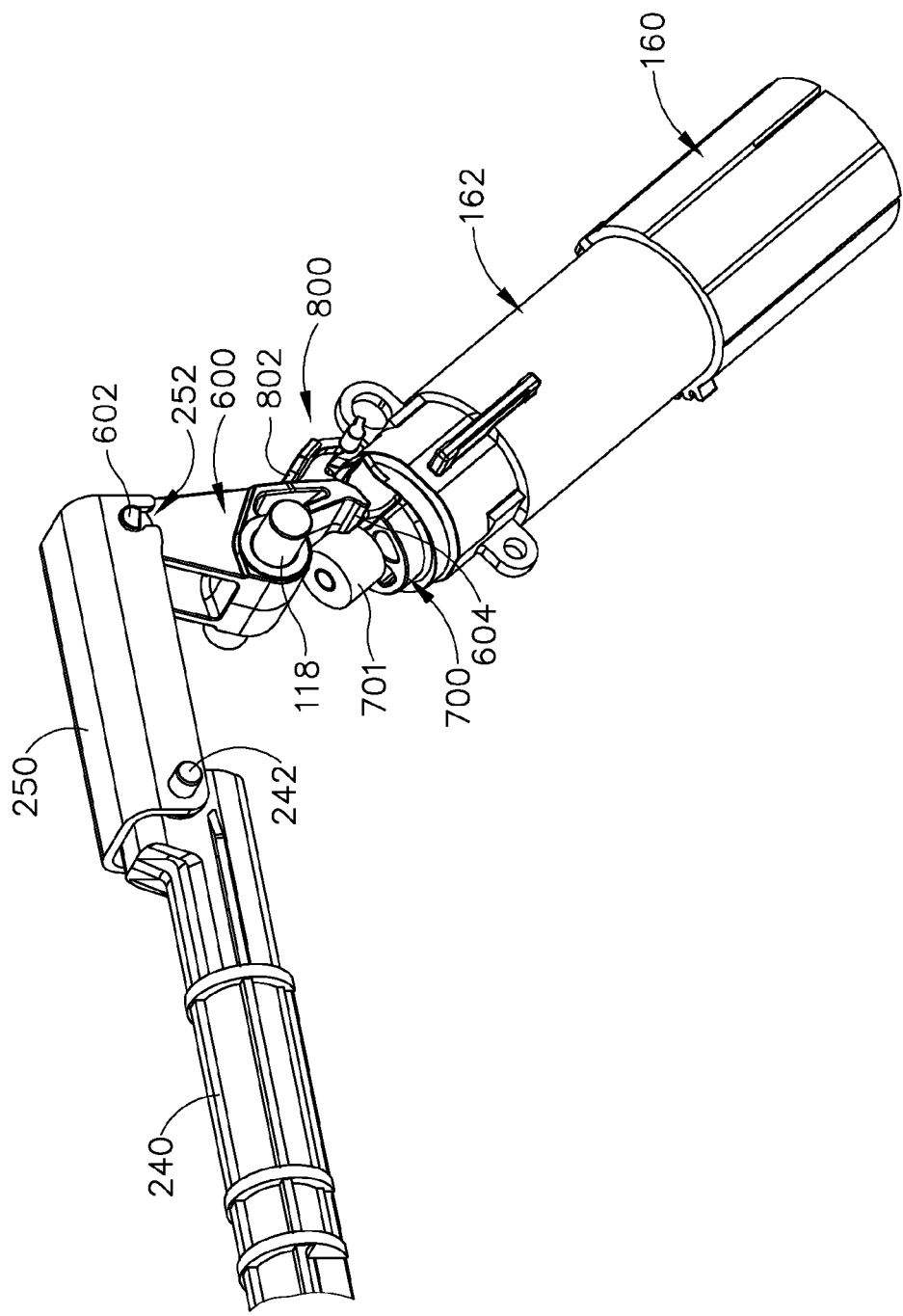
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
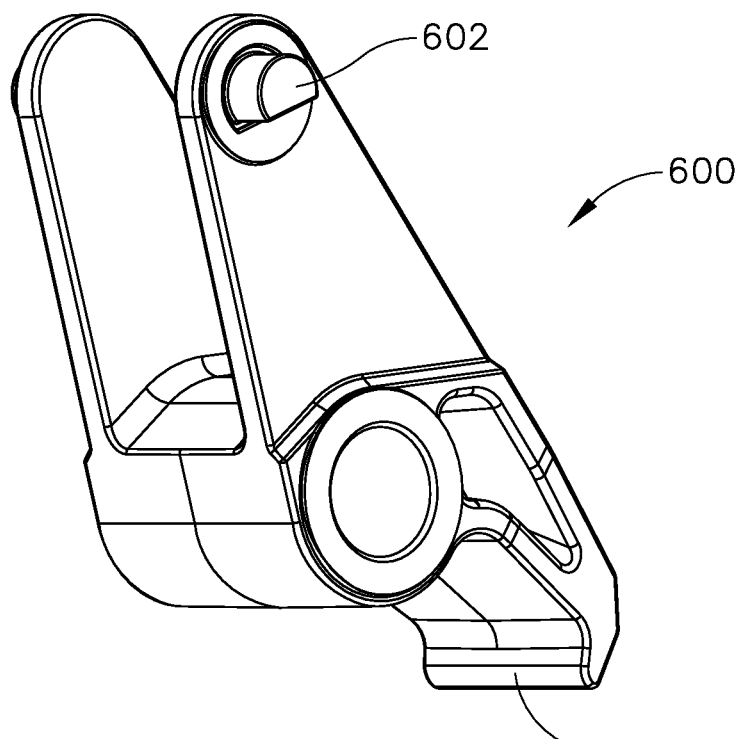
FIG. 14 depicts a perspective view of a cam follower of the stapling head actuation assembly of FIG. 13.
Figure 15:
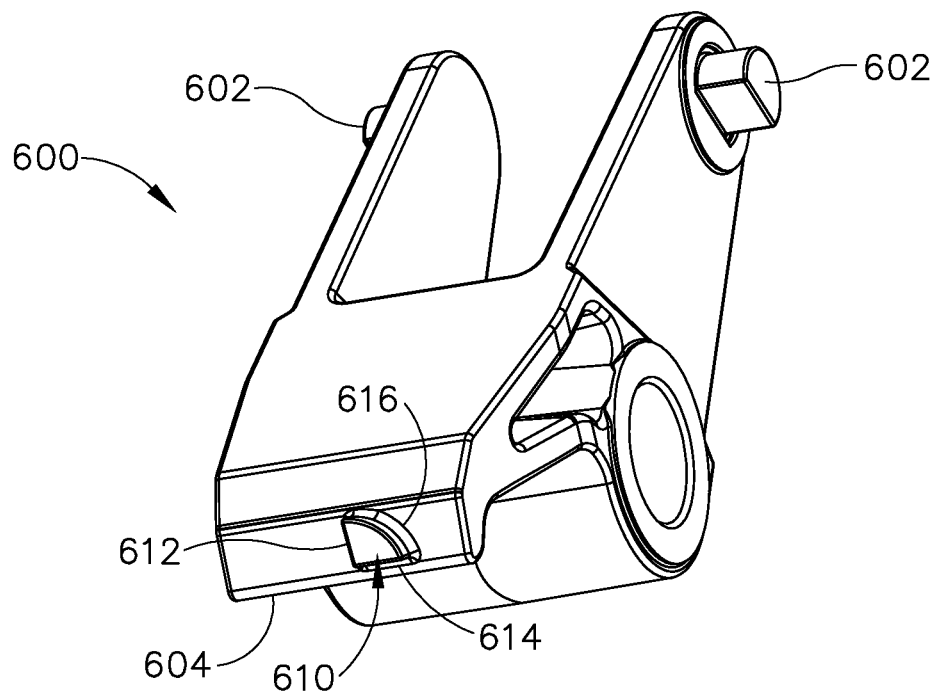
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
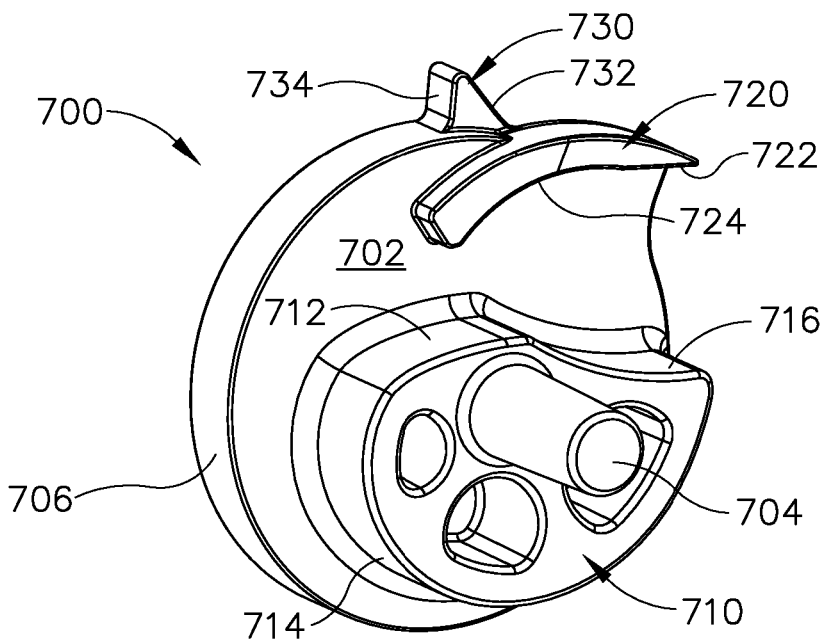
FIG. 16 depicts a perspective view of a rotary cam of the stapling head actuation assembly of FIG. 13.
Figure 17:
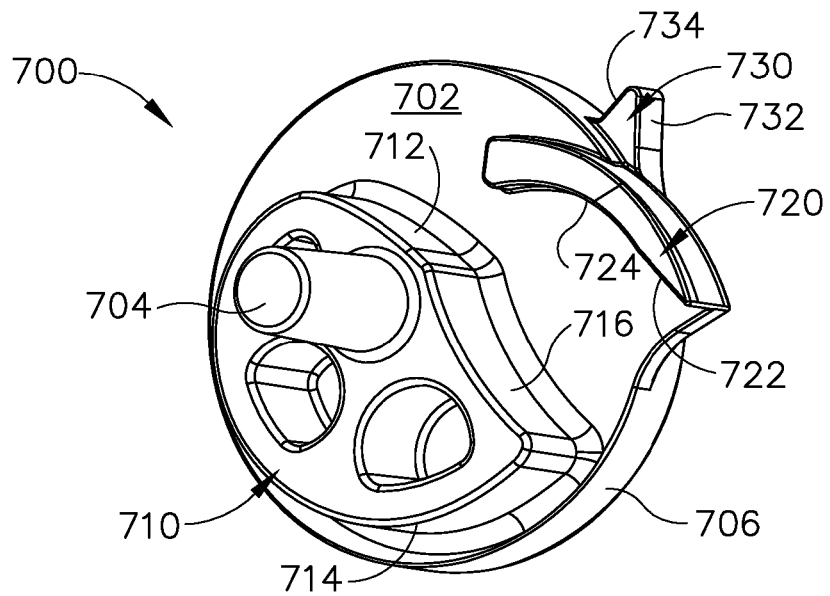
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
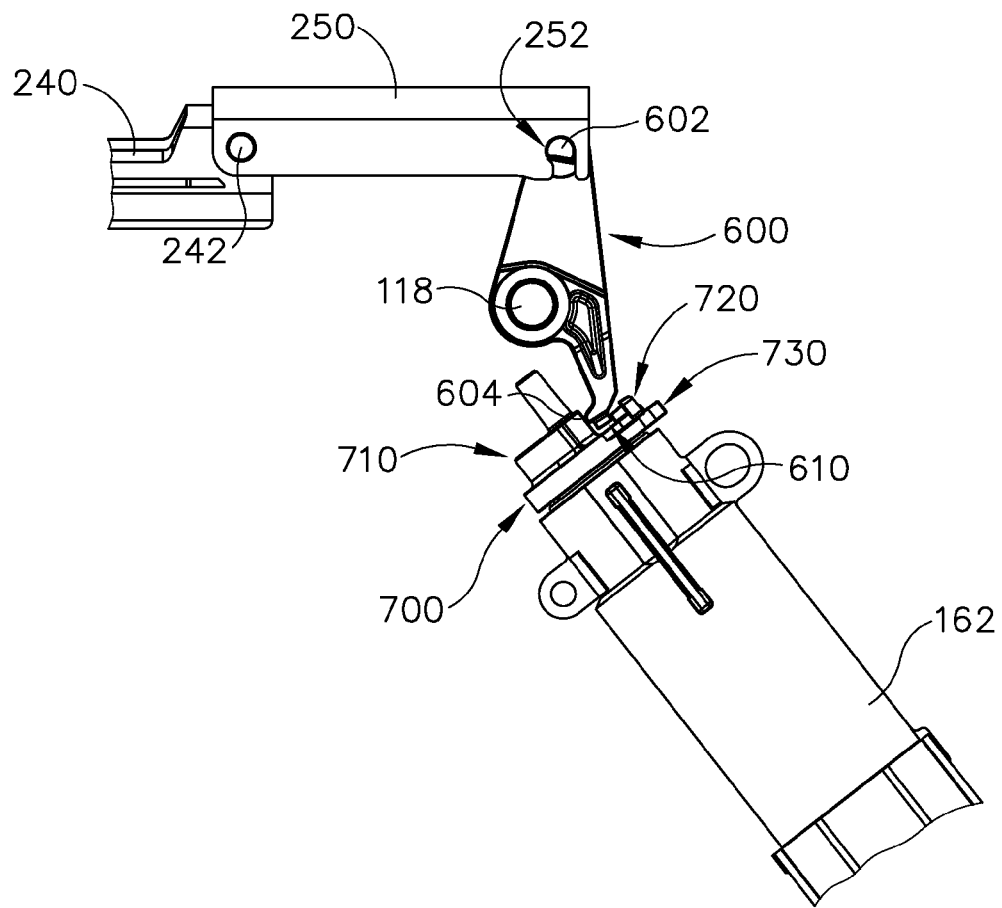
FIG. 18A depicts a side elevational view of the stapling head actuation assembly of FIG. 13, with the rotary cam in a first angular position and the cam follower in a first pivotal position.
Figure 18B:
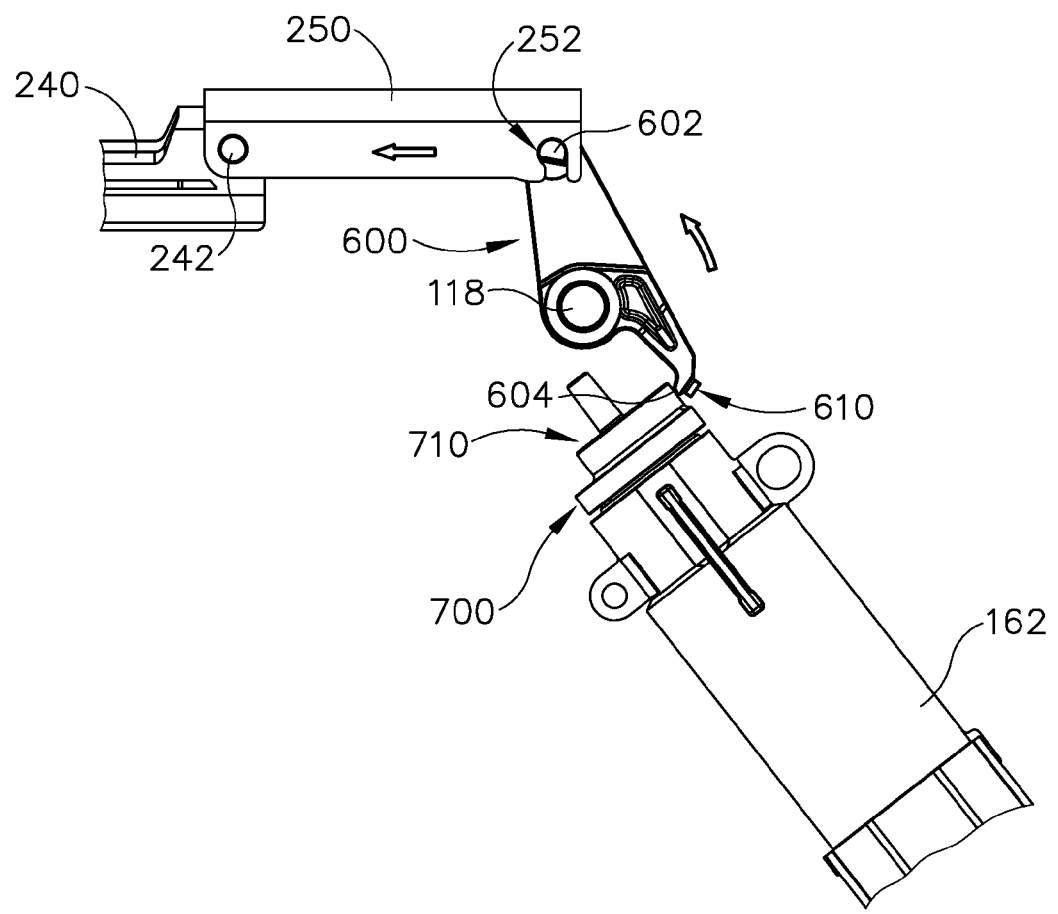
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118).

In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
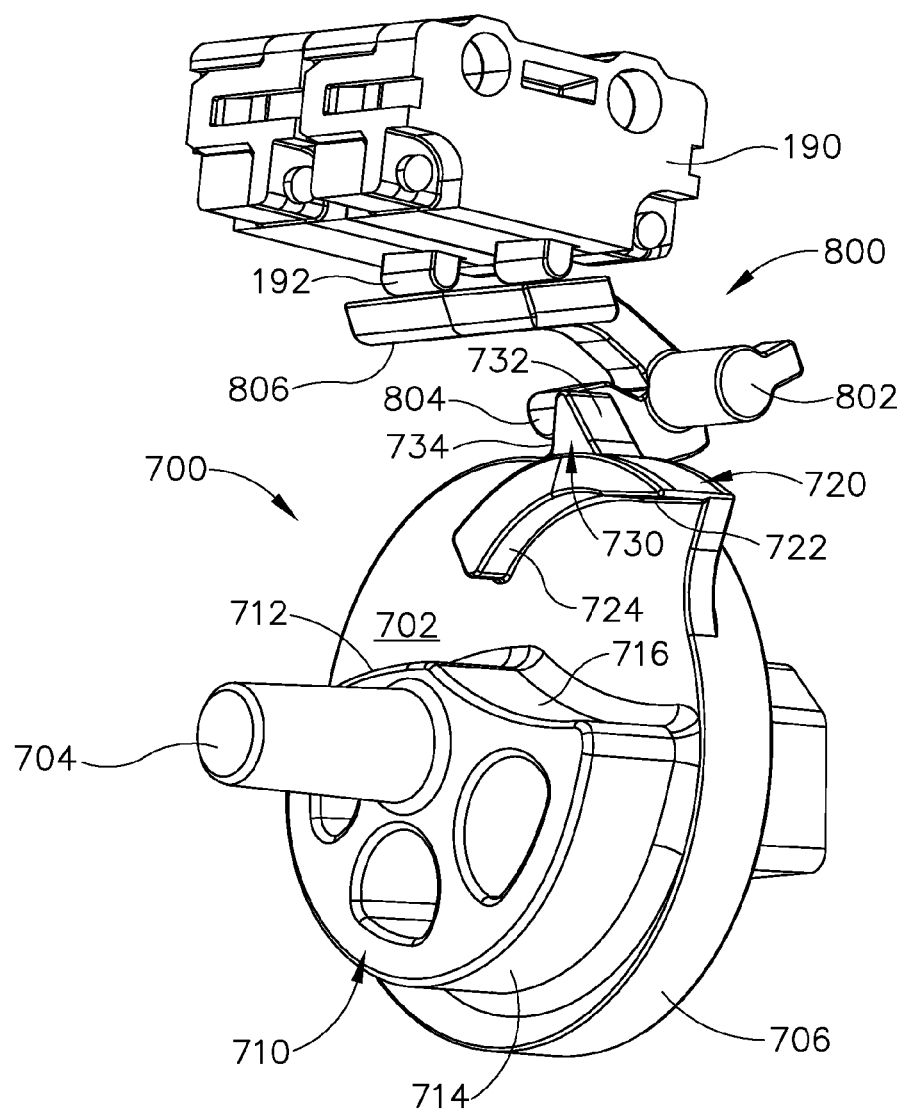
FIG. 19A depicts a perspective view of the rotary cam of FIG. 16, a rocker member, and a stop switch, with the rotary cam in a first angular position and the rocker member in a first pivotal position.
Figure 19B:
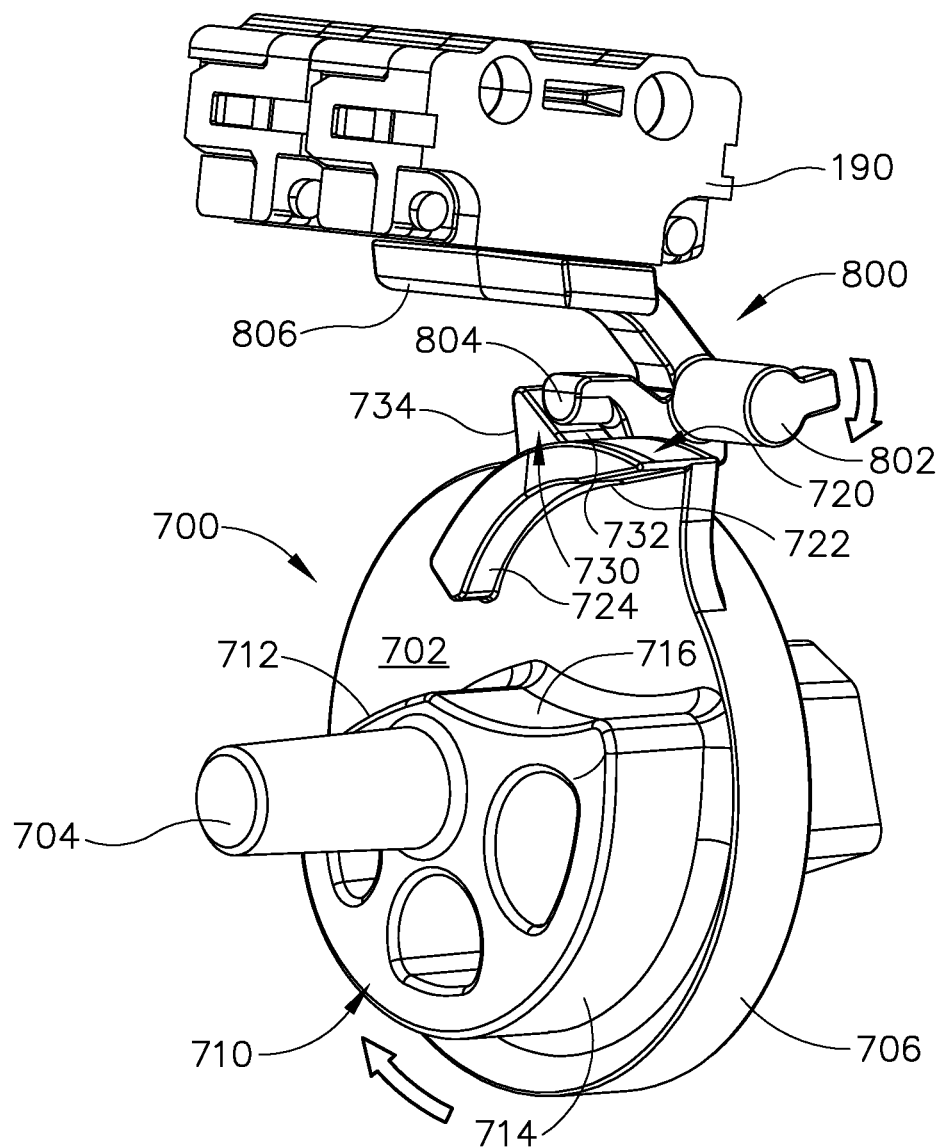
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, now U.S. Pat. No. 9,907,552, issued Mar. 6, 2018, the disclosure of which is incorporated by reference herein. Other suitable configurations will be apparent to those of ordinary skill in the art in view of the teachings herein.

Figure 20A:
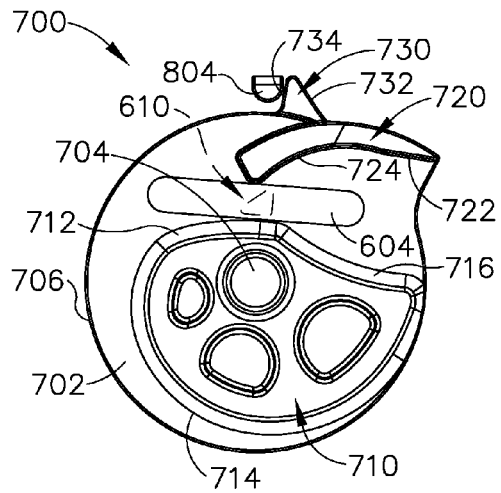
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
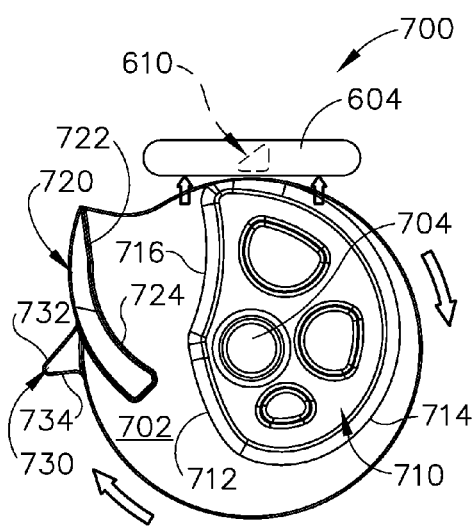
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
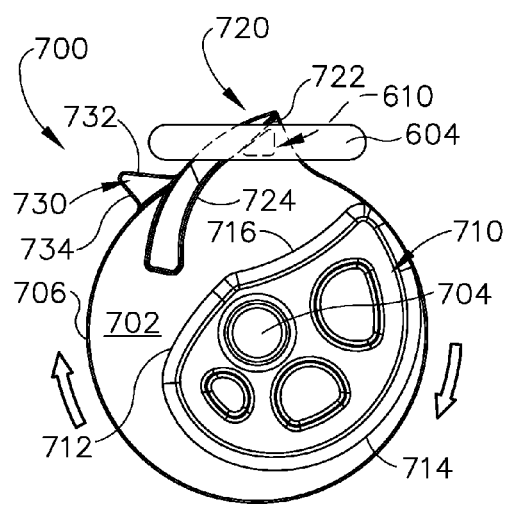
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
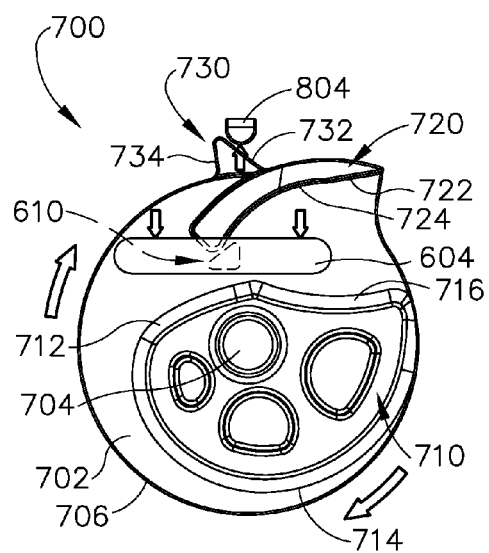
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
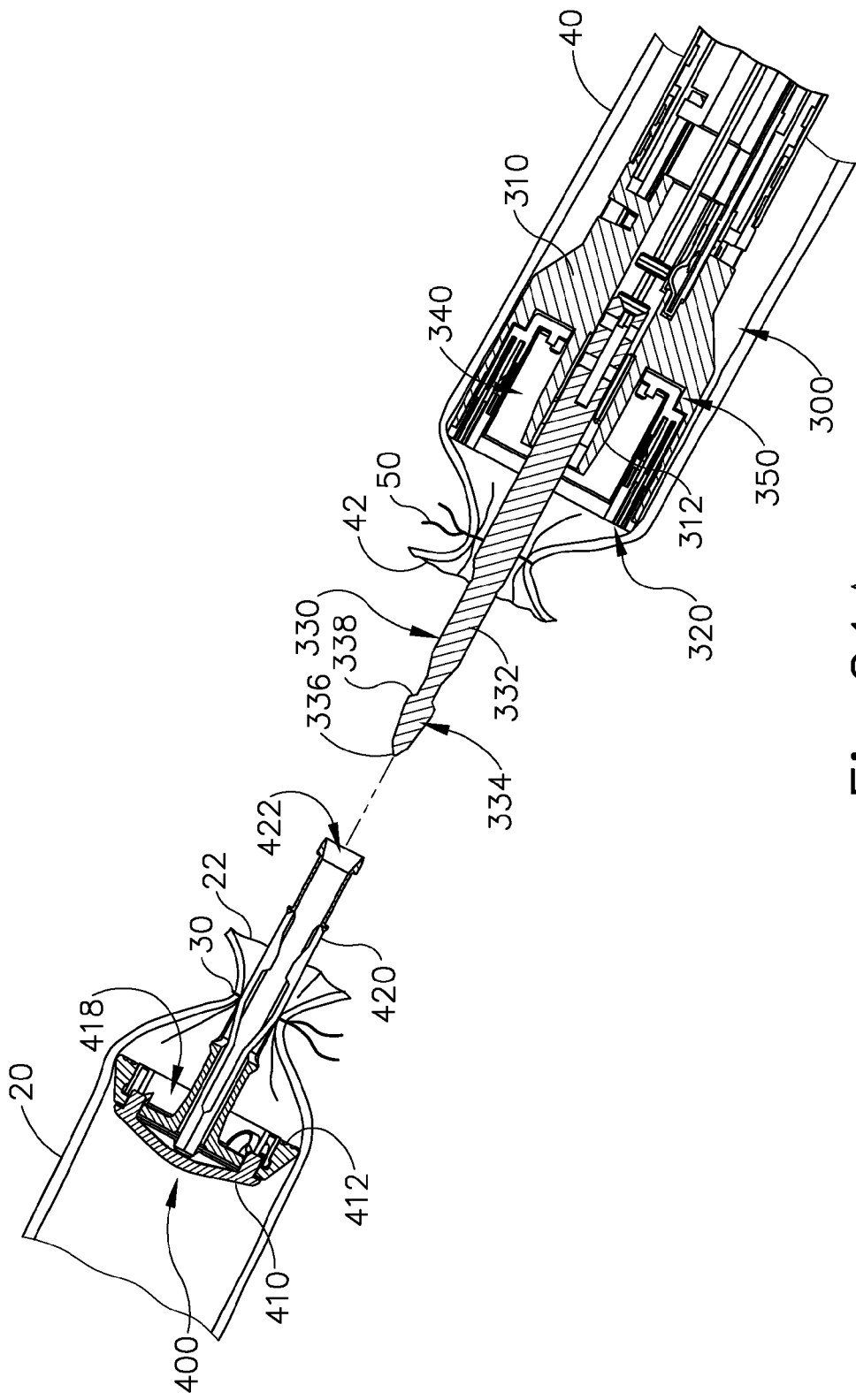
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
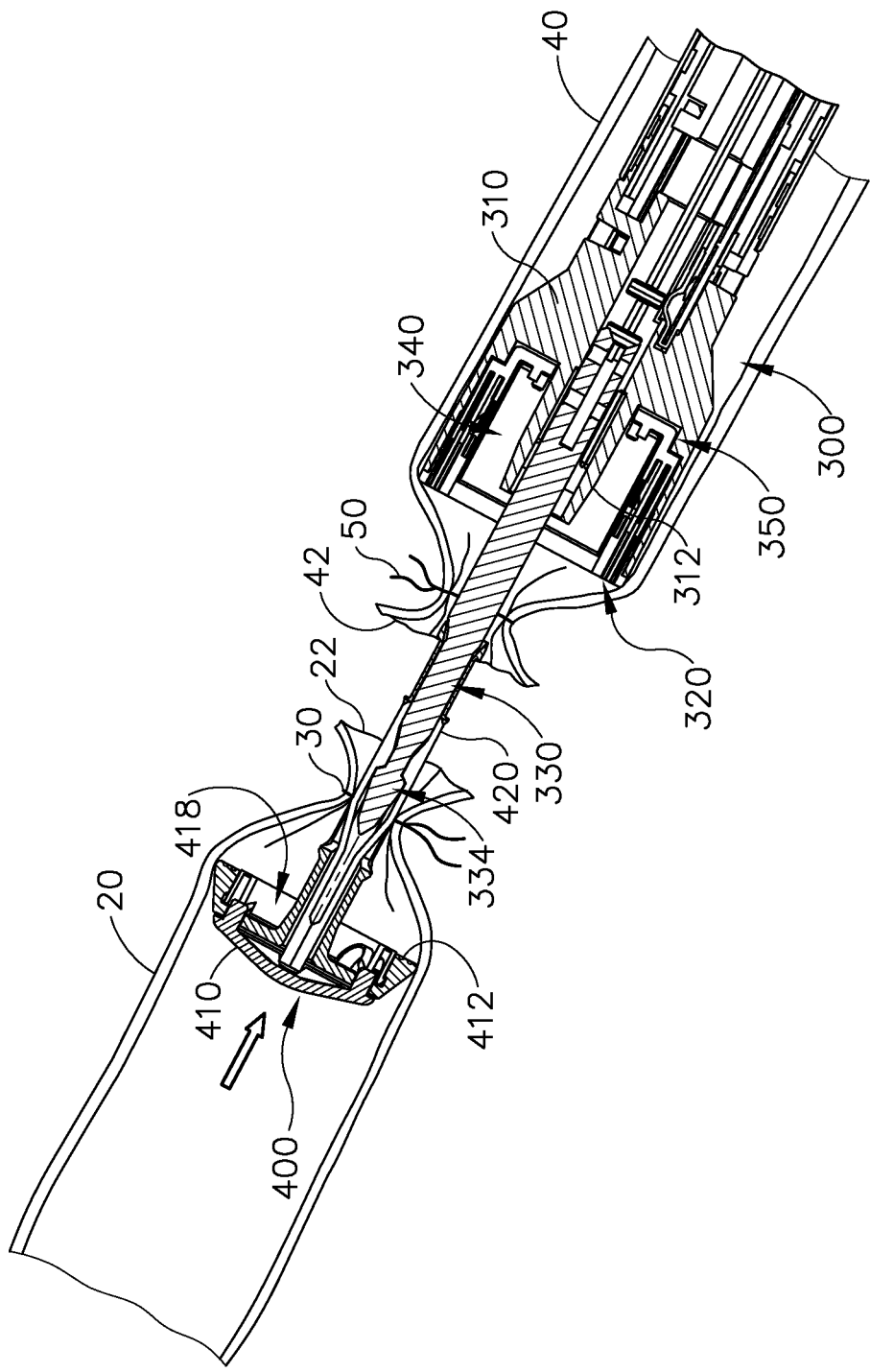
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
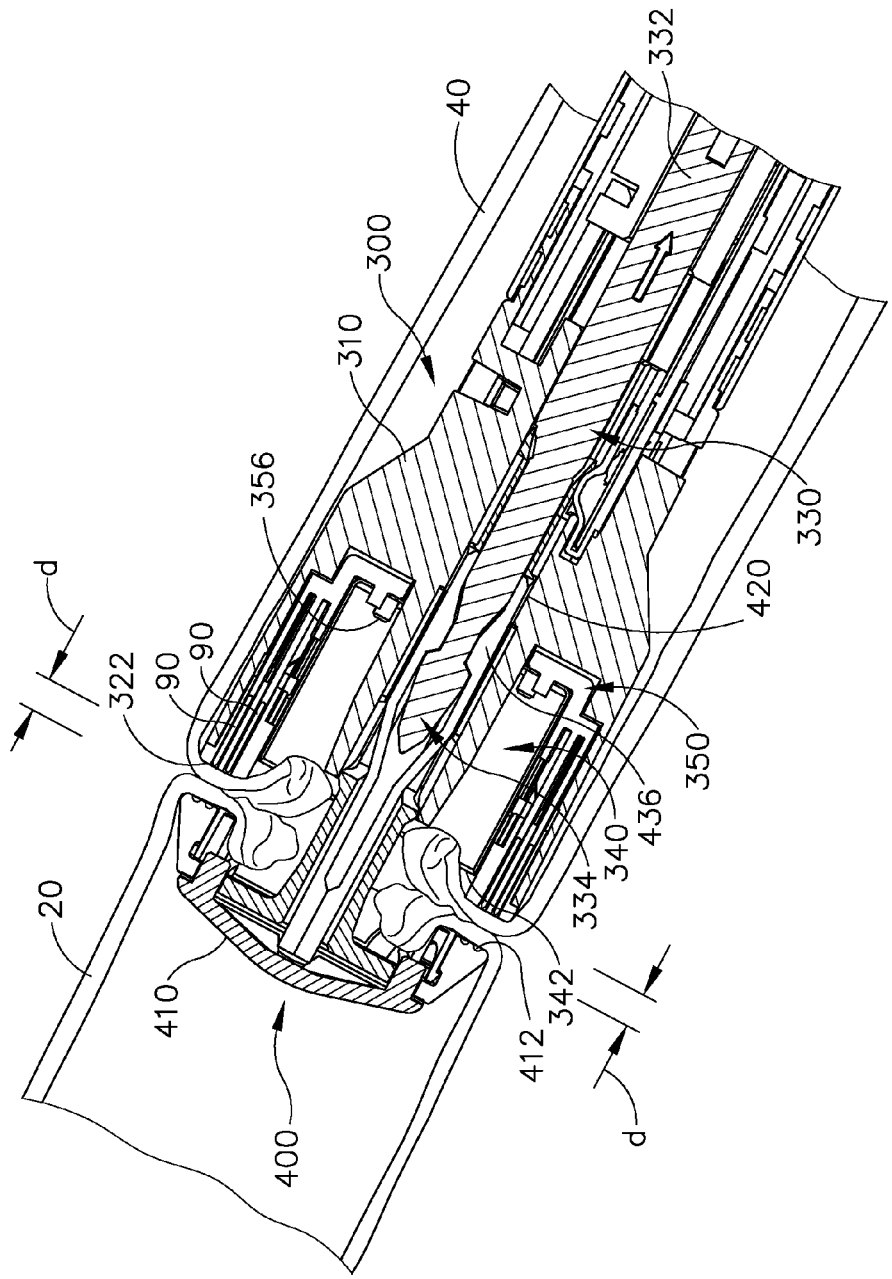
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Firing Indication System

In some instances, it may be desirable for an operator to verify complete actuation of stapling head assembly (300). In particular, it may be helpful for an operator to know when staple driver member (350) has driven staples (90) and cutting edge (342) of knife member (340) has successfully sheared off excess tissue so the operator can determine when it is appropriate to drive anvil (400) distally away from stapling head assembly (300), thereby increasing the gap distance (d) to facilitate release of tissue between surfaces (412, 322) before removing instrument (10) from the patient. The following are merely illustrative examples of various ways to indicate when the firing of staple driver member (350) and knife member (340) has been completed. Other variations or appropriate combinations of present examples and/or other variations will be apparent to one having ordinary skill in the art in view of the teachings herein.

A. Microprocessor Firing Indication System

Figure 22:
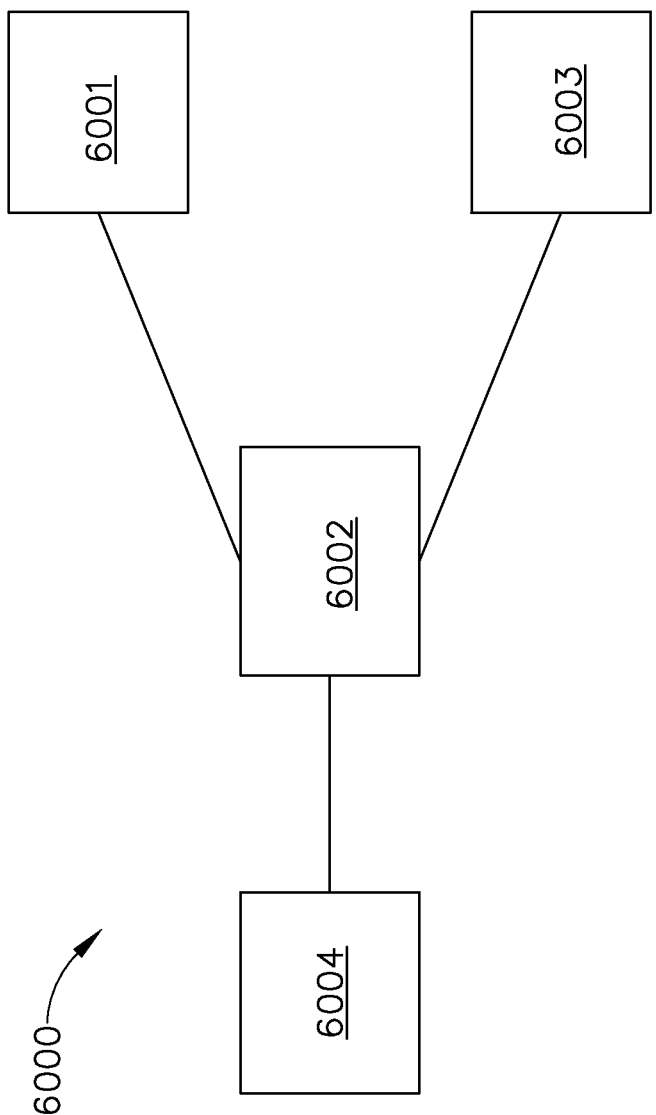
FIG. 22 depicts a schematic view of an exemplary firing indication system that may be incorporated into the circular stapler of FIG. 1.

FIG. 22 depicts a block diagram of an exemplary system (6000) that may be readily incorporated into instrument (10) in order to indicate when stapling head assembly (300) has been fully actuated. System (6000) of this example comprises a microprocessor (6002) that is in communication with a power source (6001), a motor (6003), and an indicator (6004). Power source (6001) is configured to provide electrical power to motor (6003) when an operator activates the appropriate firing mechanisms (not shown). By way of example only, motor (6003) may comprise motor (160) described above; and power source (6001) may comprise battery pack (120) described above.

Indicator (6004) may be located anywhere on, within, or near the instrument in order to appropriately communicate information to an operator. For example, indicator (6004) could comprise an auditory feedback feature (capable of generating a variety of sounds when activated) that is located inside or outside surgical instrument. Additionally, indicator (6004) may include an LED light located within a translucent portion of the body of instrument, capable of emitting light outside surgical stapler to communicate information to operator. Indicator (6004) could also be positioned outside the body of instrument in such a manner to communicate appropriate information to operator. Indicator (6004) could also comprise an LCD screen attached to the body of instrument or separated from instrument. In some instances, indicator (6004) is viewable through window (114) or is otherwise placed at the location of window (114). Various suitable forms that indicator (6004) may take, as well as various places where indicator (6004) may be located, will be apparent to those of ordinary skill in the art in view of the teachings herein.

Figure 23:
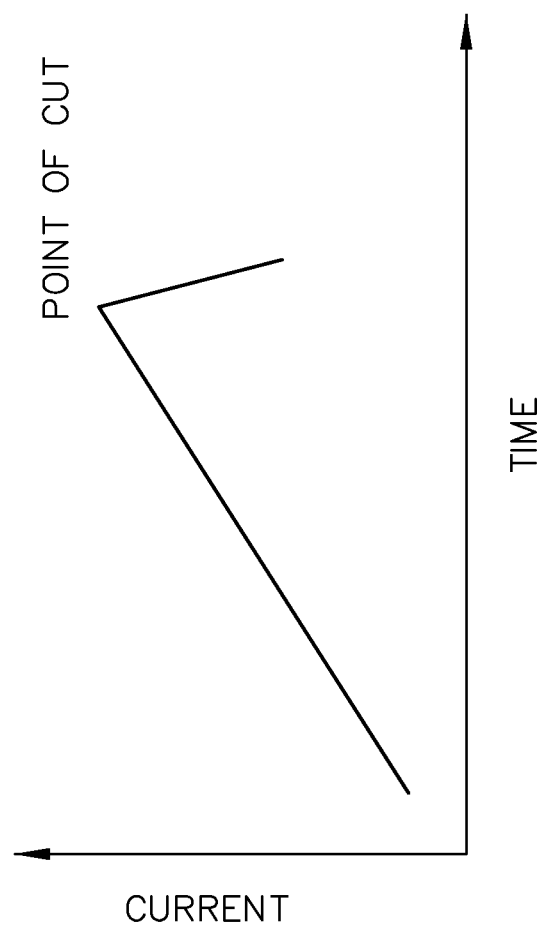
FIG. 23 depicts a graph of current as a function of time in relation to a power source supplying power to a motor of the firing indication system of FIG. 22.

Microprocessor (6002) is electrically coupled to both power source (6001) and motor (6003). Therefore, microprocessor (6002) is capable of measuring the electrical current supplied from power source (6001) to motor (6003). Of course, any other means of measuring current could be utilized instead of microprocessor (6002). As best shown in FIG. 23, current supplied from power source (6001) to motor (6003) increases once appropriate firing mechanisms have been activated. Once motor has completed its course of travel, as exemplified in FIG. 20D, power source (6001) is no longer driving staple driver member (350) or knife member (340). This is shown approximately around the point of cut shown on FIG. 23. Because power source (6001) is no longer driving staple driver member (350) or knife member (340), the current level measured by microprocessor (6002) drops as compared to when power source (6001) was powering motor (6003).

Once microprocessor (6002) detects a drop in current associated with completion of actuation of stapling head assembly (300), microprocessor (6002) then activates indicator (6004). Indicator (6004) thus signals to an operator that the current level of power provided from power source (6001) to motor (6003) has dropped, signifying a completion of actuation of stapling head assembly (300). It should be noted that while microprocessor (6002) measures current supplied from power source (6001) to motor (6003), microprocessor (6002) does not have to strictly measure current or be connected to both power source (6001) and motor (6003) in order to determine completion of the firing process. For example, microprocessor (6002) could be in communication with only power source (6001) and indicator (6004) and measure the drop in potential of power source (6001) caused by activation of motor (6003). Other suitable configurations and techniques that may be used to measure activation and deactivation of motor (6003) will be apparent to a person having ordinary skill in the art in view of the teachings herein.

B. Physical Firing Indication System

Figure 24:
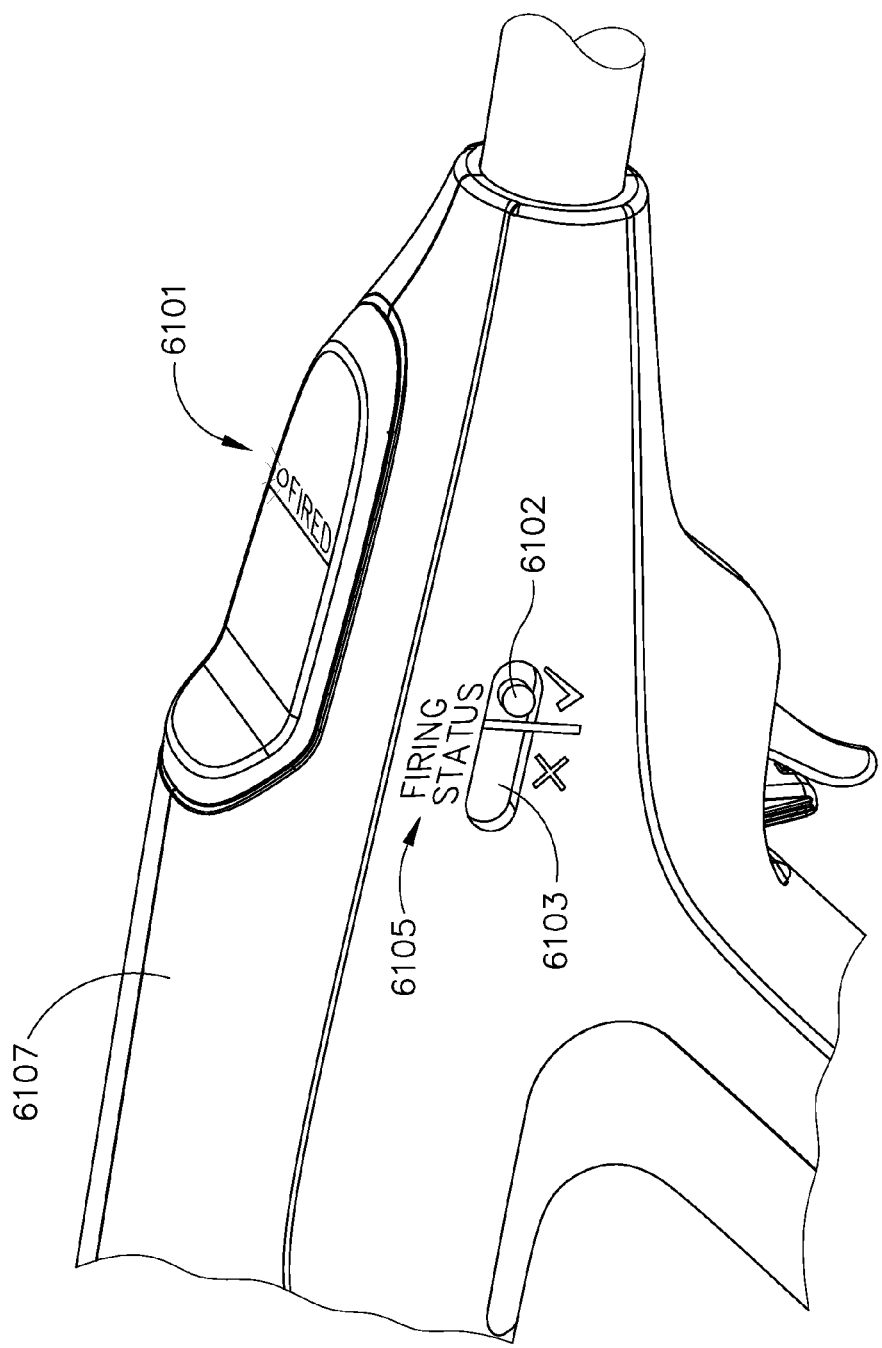
FIG. 24 depicts a partial perspective view of a handle of a an exemplary firing indication system that may be incorporated into the circular stapler of FIG. 1.
Figure 25:
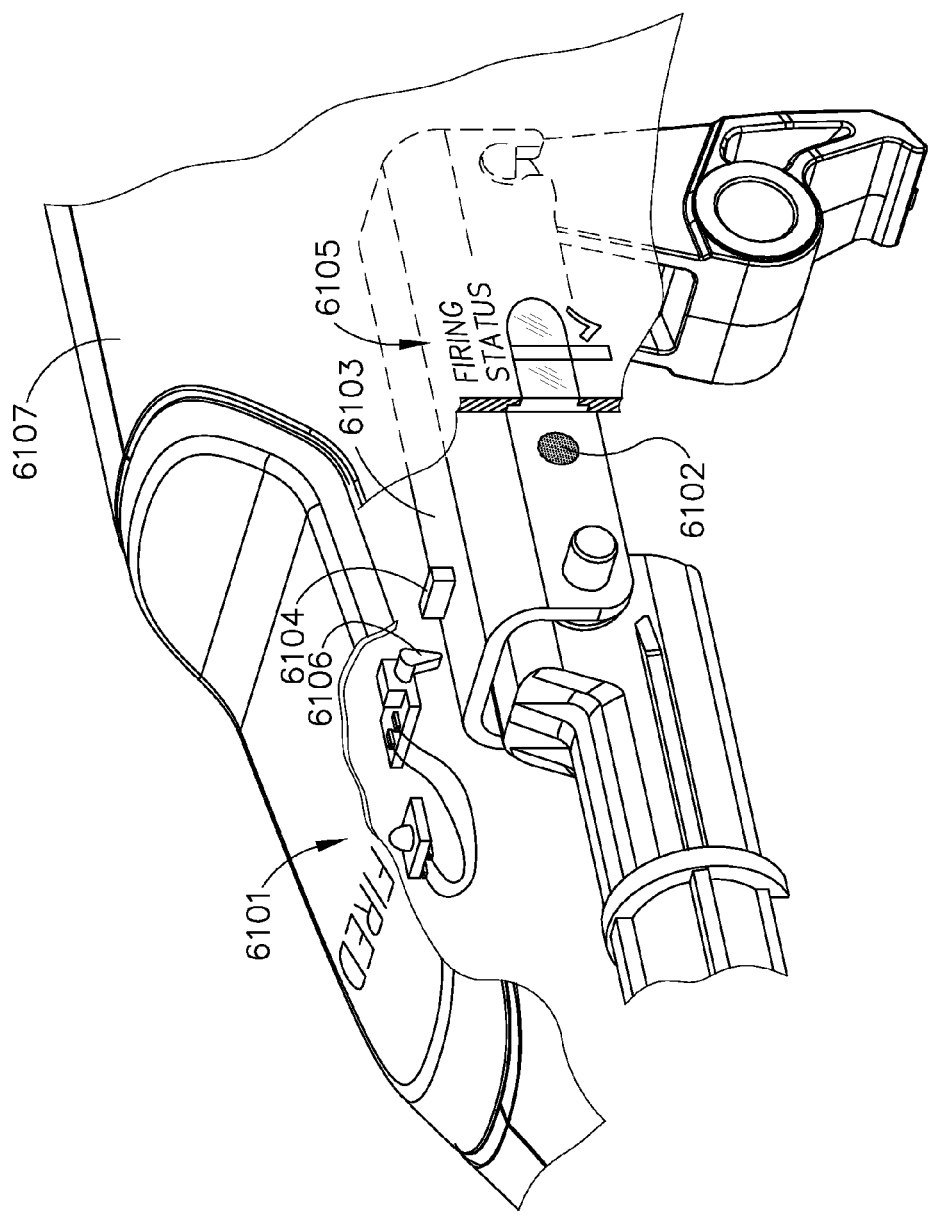
FIG. 25 depicts a partial cutaway perspective view of the firing indication system of FIG. 24.

FIGS. 24-25 depict various features that may be utilized to verify complete actuation of stapling head assembly (300). These features may be readily incorporated into instrument (10). Instead of measuring electrical properties between supply source (6001) and motor (6003), the features depicted in FIGS. 24-25 measure the physical positioning of components that actuate stapling head assembly (300). It should be understood that the physical location of components that actuate stapling head assembly (300) may indicate whether stapling head assembly (300) is in a fired state or an un-fired state.

FIG. 24 shows a casing (6107), an indication light (6101), a transparent indicator window (6105), and an indicator marking (6102) located on drive bracket (6103). It should be noted that casing (6107) is substantially similar to casing (110) mentioned above. Additionally, drive bracket (6103) is substantially similar to drive bracket (250) mentioned above. Transparent indicator window (6105) and indicator marking (6102) are used in tandem to visually display the physical location of drive bracket (6103). Transparent indicator window (6105) and casing (6107) include fixed markings that provide reference points to compare the location of indicator marking (6102) against in order to determine the position of drive bracket (6103). It should be understood that, based on the location of indicator marking (6102) relative to the predetermined markings on transparent indicator window (6105) and casing (6107), an operator may determine if stapling head assembly (300) has completed actuation.

For instance, when stapling head assembly (300) is in an unfired state, drive bracket (6103) will be in a proximal position, such that indicator marking (6102) will also be in a proximal position. In the proximal position, indicator marking (6102) will be viewable though transparent indicator window (6105) adjacent to an "X" or some other indication, thereby indicating to the operator that stapling head assembly (300) is in an unfired state. When stapling head assembly (300) is in a fired state or has been fired, drive bracket (6103) will be advanced to a distal position, such that indicator marking (6102) will also be advanced to a distal position. In the distal position, indicator marking (6102) will be viewable through transparent indicator window (6105) adjacent to a check mark or some other indication, therefore indicating to the operator that stapling head assembly (300) has been fired.

Indicator light (6101) works separately and independently from indicator marking (6102) and transparent indicator window (6105). It should therefore be understood that an instrument may include indicator light (6101) yet lack indicator marking (6102) and transparent indicator window (6105). Similarly, an instrument may include indicator marking (6102) and transparent indicator window (6105) yet lack indicator light (6101). As shown in FIG. 25, in the present example indicator light (6101) is in communication with a switch (6106) via wiring (6107). Indicator light (6101) and switch (6106) are both secured to casing (6107). Switch (6106) is operable to pivot based on contact with a protrusion (6104). Pivoting of switch (6106) will activate indicator light (6101), such that indicator light (6101) will illuminate when protrusion (6104) actuates switch (6106). Indicator light (6101) may be configured to illuminate at different colors based on the angular direction that switch (6106) is pivoted, or for any other reason that would be apparent to a personal having ordinary skill in the art in view of the teachings herein.

Protrusion (6104) is fixed to drive bracket (6103). Protrusion (6104) extends from drive bracket (6103) at a location such that protrusion (6104) will actuate switch (6106) based on the firing status of stapling head assembly (300). For instance, when stapling head assembly (300) is in an unfired state, drive bracket (6103) will be in a proximal position. Therefore, protrusion (6104) will also be in a proximal position such that protrusion (6104) is spaced away from switch (6106). Because protrusion (6104) has yet to rotate switch (6106) in any angular direction, indicator light (6101) remains turned off (i.e., non-illuminated), thereby indicating to an operator that stapling head assembly (300) is in an unfired state. When stapling head assembly (300) is in a fired state or has been fired, drive bracket (6103) will be moved to a distal position, such that protrusion (6104) will also be moved to a distal position. As protrusion (6104) travels from a proximal position to a distal position, protrusion (6104) will rotate switch (6106) in a first angular direction. Because protrusion (6104) has rotated switch in a first angular direction, indicator light (6101) illuminates at a first color of light, thereby indicating to the operator that stapling head assembly (300) has been fired.

Additionally, protrusion (6104) may be configured to actuate switch (6106) a second time when drive bracket (6103) returns to the proximal position after stapling head assembly (300) has stapled and severed tissue. If protrusion (6104) is positioned on drive bracket (6103) in this manner, protrusion will (6104) translate from a distal position back to a proximal position, therefore rotating switch (6106) in a second angular direction that is opposite to the direction in which switch (6106) rotates during distal translation of drive bracket (6103). Because protrusion (6104) has rotated switch in a second angular direction, indicator light (6101) may illuminate at a second color of light, thereby indicating to the operator that the full stroke for stapling head assembly (300) has been completed. In other words, protrusion (6104) may rotate switch (6106) in a first angular direction to indicate when stapling and severing tissue occurs, then protrusion (6104) may rotate switch (6106) in a second angular direction to indicate when stapling head assembly (300) has completed its entire course of travel.

For exemplary purposes, switch (6106) may be configured to only light up only when protrusion (6104) has rotated switch (6106) in either a first angular direction or a second angular direction. Switch (6106) may be capable of only lighting up indicator light (6101) with one color, but blinking when rotating in a first angular direction and remaining lit when rotating in a second-opposite angular direction. Indicator light (6101) might use other forms of indicating, such as auditory rather than visual. Other suitable variations will be apparent to one having ordinary skill in the art in view of the teachings herein.

III. Exemplary Anvil Position Indicators

As mentioned above, after the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). In some instances, it may be desirable for an operator to know when knob (130) has been sufficiently rotated to have driven anvil (400) far enough away from stapling head assembly (300) in order to increase an appropriate gap distance (d) to facilitate release of tissue between surfaces (412, 322). The following are merely illustrative examples of various ways to indicate when anvil (400) and stapling head assembly (300) have a sufficient gap distance (d) to facilitate release of tissue between surfaces (412, 322) of anvil (400) and stapling head assembly (300). Other variations or appropriate combinations of present examples and/ or other variations will be apparent to one having ordinary skill in the art in view of the teachings herein.

A. Electric Contact Switch Indicator

Figure 26:
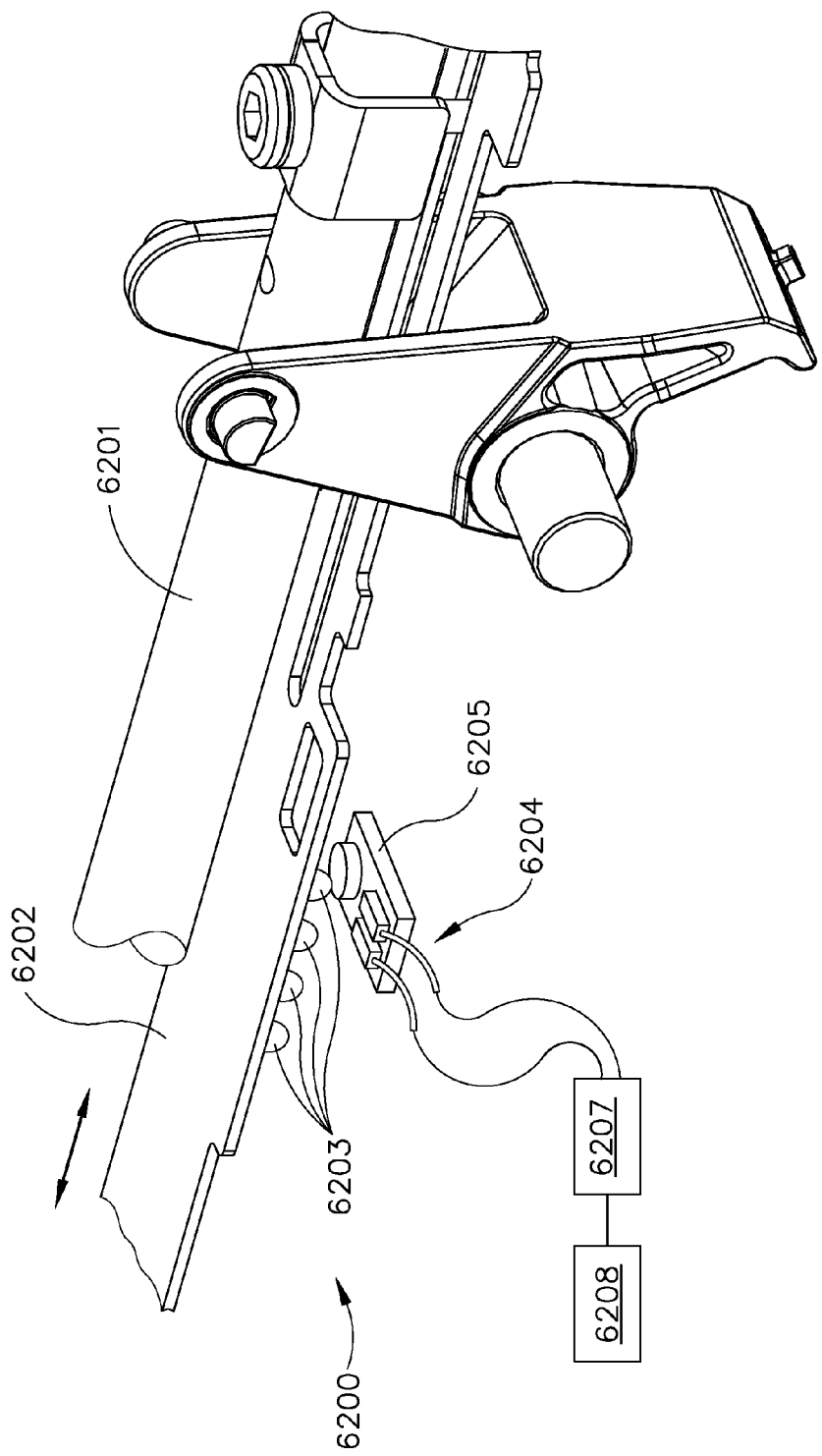
FIG. 26 depicts a partial perspective view of an exemplary trocar actuation assembly with a tissue release indicator system that may be incorporated into the circular stapler of FIG. 1.
Figure 27:
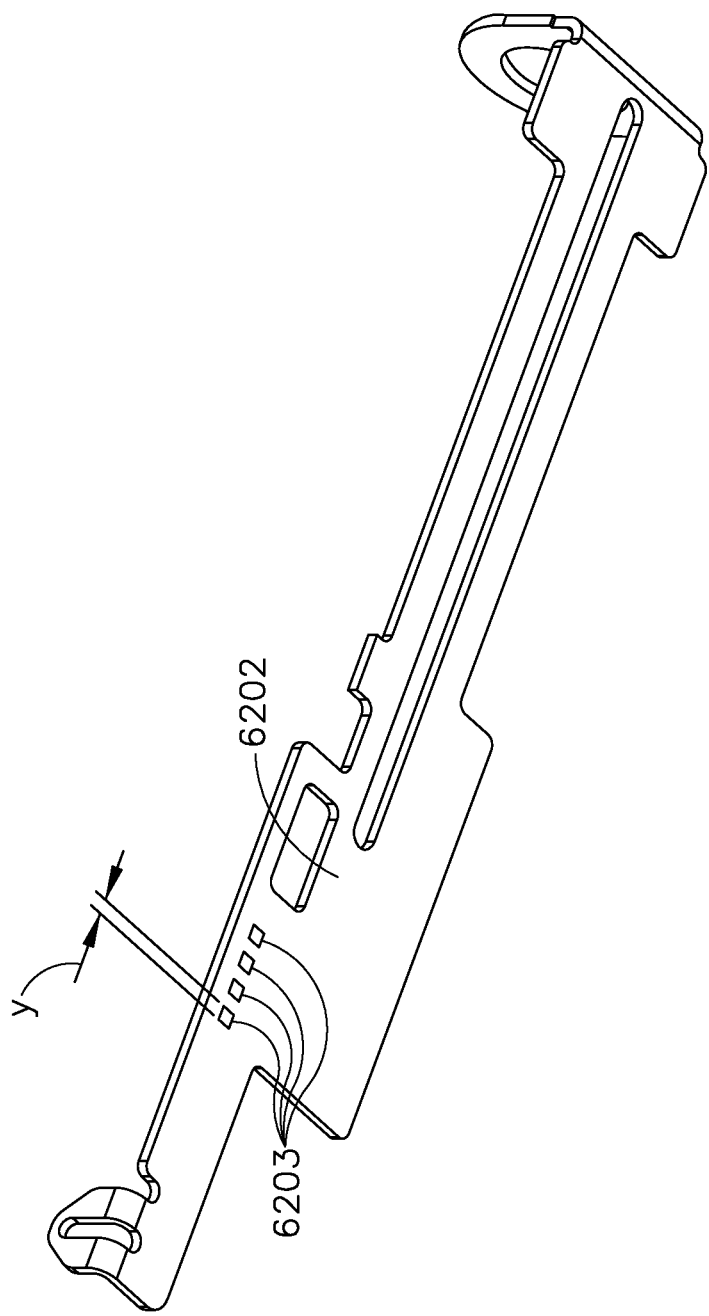
FIG. 27 depicts a perspective view of a bracket of the tissue release indicator system of FIG. 26.
Figure 28:
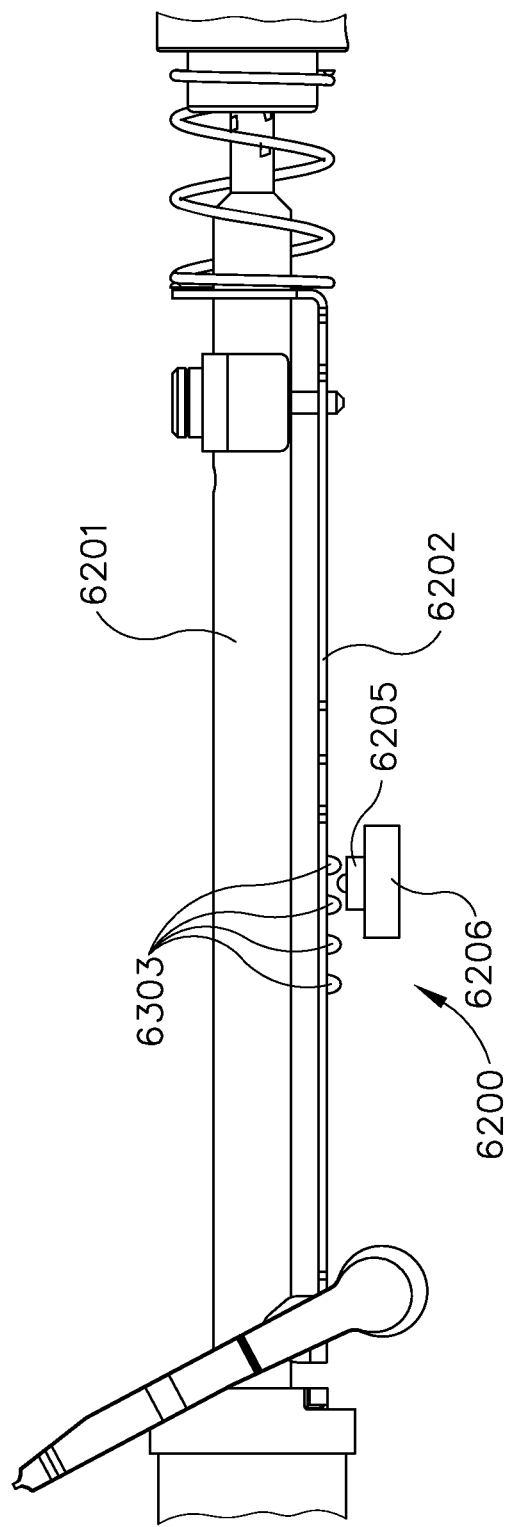
FIG. 28 depicts a side elevational view of the trocar actuation assembly of FIG. 26.

FIGS. 26-28 depict a switch system (6200) that is operable to indicate a sufficient gap distance (d) to facilitate proper release of stapled tissue between surface (412, 322) of anvil (400) and stapling head assembly (300). Switch system (6200) may be readily incorporated into instrument (10). Switch system (6200) comprises a trocar actuation rod (6201), a bracket (6202) coupled with trocar actuation rod (6201), a switch (6205) fixed to casing (6206), a counter (6207) and an indicator (6208). Trocar actuation rod (6201) is substantially similar to trocar actuation rod (220) mentioned above. Therefore, it should therefore be understood that trocar (330) and anvil (400) will translate longitudinally relative to outer sheath (210) in response to translation of trocar actuation rod (6201) relative to outer sheath (210). Bracket (6202) is substantially similar to bracket (500) mentioned above. However, bracket (6202) of this example further comprises a linear array of markers (6203) that are arranged in a longitudinally extending array along a path that is parallel with the longitudinal direction defined by trocar actuation rod (6201). Bracket (6202) is configured and positioned to move longitudinally in response to longitudinal movement of trocar actuation rod (6201).

Adjacent markers (6203) of the linear array of markers (6203) are positioned equidistantly apart. Markers (6203) are positioned along bracket (6202) in order to compress and release switch (6205) while trocar actuation rod (6201) distally actuates trocar (330) away from stapling head assembly (300) to create a sufficient gap distance (d) to release tissue. In other words, markers (6203) are driven distally with bracket (6202) and trocar actuation rod (6201), markers (6203) successively engage fixed switch (6205). In some versions, markers (6203) physically press against switch (6205) and thereby actuate switch (6205) through direct contact. In some other versions, switch (6205) comprises a proximity sensor, an optical sensor, or some other kind of sensor that is responsive to passage of markers (6203) over switch (6205) without necessarily having to come into direct contact with markers (6203).

Switch (6205) is coupled to a counter (6207) (which may be similar to microprocessor (6002)) via wiring (6204). Counter (6207) counts the number of times markers (6203) compress and release switch (6205). Since markers (6203) are spaced apart equidistantly, each compression and release of switch (6205) correlates to a predetermined distance (y) of travel by bracket (6202), trocar actuation rod (6201) and anvil (400). Therefore, once switch (6205) is compressed and released a predetermined number of times, counter (6207) will be able to determine when a sufficient gap distance (d) is created to facilitate release of tissue between surfaces (412, 322).

As shown in FIG. 28, it is important that markers (6203) are distanced far enough from each other to allow switch (6205) to fully compress and release, thereby ensuring each segment of predetermined distance (y) is accounted for by counter (6207). Additionally, while switch (6205) is currently shown as being linearly actuated, switch may also count marks through angular rotation or any other means apparent to one having ordinary skill in the art in view of the teachings herein. Also, linear array of markers (6203) can be substituted for one marker (6203) that is placed to engage switch (6405) precisely at the point where a sufficient gap distance (d) is defined for safe removal of tissue from surfaces (412, 322) of anvil (400) and stapling head assembly (300).

Once counter (6207) determines that switch (6205) has been actuated a sufficient number of times indicating an appropriate gap distance (d), counter (6207) activates indicator (6208). Activation of indicator (6208) may indicate to the operator that a sufficient gap distance (d) has been created to release tissue between surfaces (412, 322). The operator may then remove instrument (10) from the patient.

By way of example only, indicator (6208) may provide an audible tone, an automated voice response, a textual indication, a graphical indication, illumination of a light, vibration of pistol grip (112), and/or any other suitable form of audible, visual, and/or tactile feedback. Various suitable forms that indicator (6208) may take will be apparent to one of ordinary skill in the art in view of the teachings herein.

B. Knob Detent Feature Indicator

Figure 29:
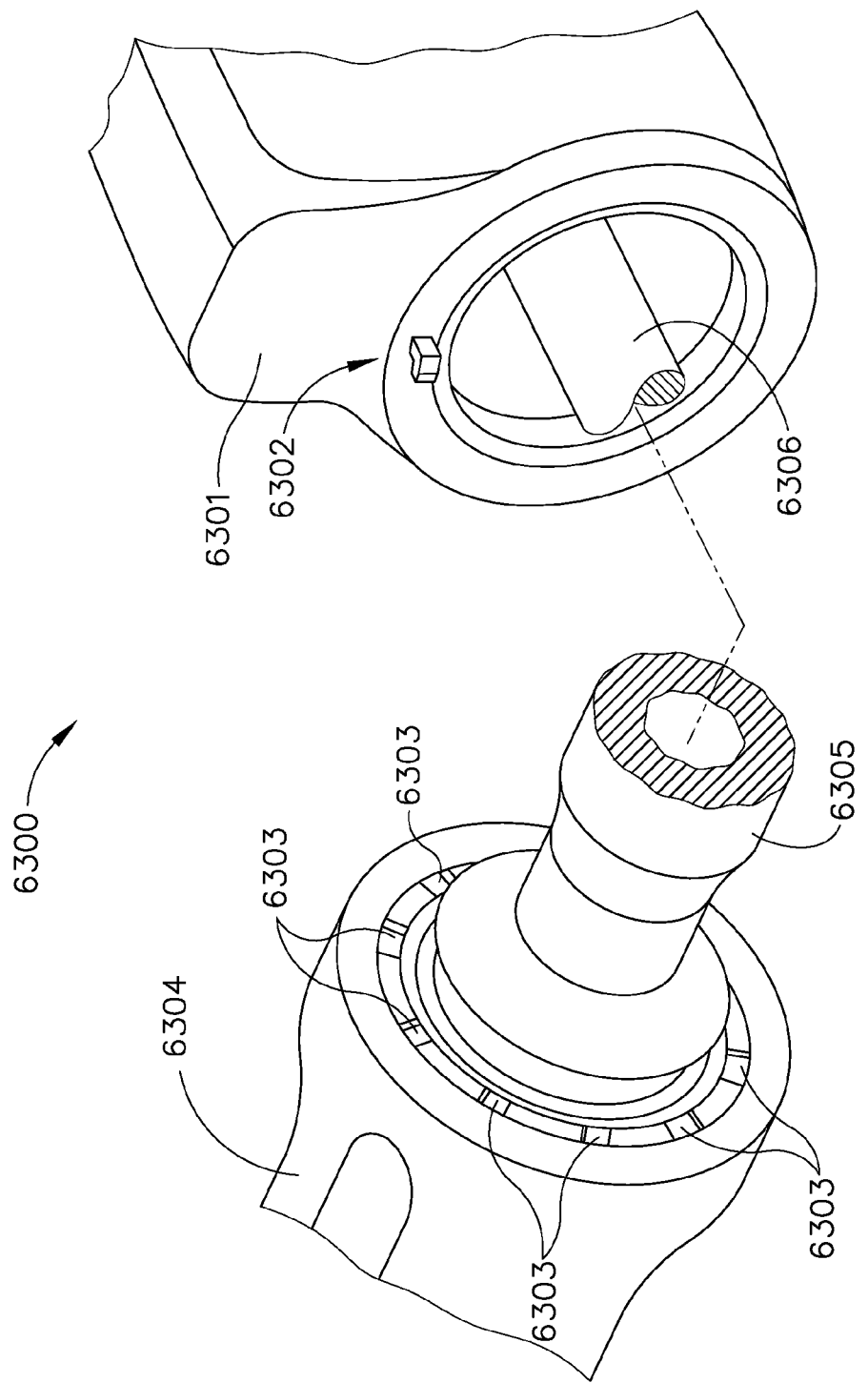
FIG. 29 depicts a broken perspective view of an exemplary tissue release indicator system that may be incorporated into the circular stapler of FIG. 1, where the tissue release indicator system is attached to a rotation knob and a handle.

FIGS. 29-31C depict an exemplary knob detent indicator (6300) that is operable to indicate a sufficient gap distance (d) to facilitate proper release of stapled tissue between surface (412, 322) of anvil (400) and stapling head assembly (300). Knob detent indicator (6300) may be readily incorporated into instrument (10). As best seen in FIG. 29, knob detent indicator (6300) comprises a knob (6304), a handle assembly (6301), and a proximal shaft segment (6305) unitarily coupled to a distal shaft segment (6306). Handle assembly (6301) is substantially similar to handle assembly (100) mentioned above, except that handle assembly (6301) comprises a resilient tab (6302) that is configured to interact with knob (6304) as will be described in greater detail below. Tab (6302) extends proximally from handle assembly (6301) and is oriented along a circumferential path.

Knob (6304) is substantially the same as knob (130) described above, except that knob (6304) further comprises an annular array of detents (6303) configured to interact with resilient tab (6306) of handle assembly (6301) as will be described in greater detail below. Detents (6303) extend distally from knob (6304) and are arranged in an annular array at a radius corresponding to the location of tab (6302) in relation to the longitudinal axis shared by shaft segments (6305, 6306). Proximal shaft segment (6305) and distal shaft segment (6306) unitarily connect knob (6304) with nut (160) so knob (6304) and nut (160) rotate together unitarily as described above.

As mentioned above, the operator rotates knob (6304) after actuating stapling head assembly (300) as shown in FIG. 21D in order to increase gap distance (d). Increasing gap distance (d) helps to facilitate release of the tissue between surfaces (412, 322). Detents (6303) are annularly spaced apart in equal angular segments and are configured to interact with resilient tab (6302) to provide an audible/tactile response in the form of a "click" when each individual detent (6303) passes over resilient tab (6302). Since detents (6303) are spaced apart in equal angular segments, each time a detent (6303) and resilient tab (6302) interact to provide an audible/tactile click, the operator may thus be informed that trocar actuation rod (220) has traveled a predetermined distance in either a proximal direction or a distal direction depending on the direction of rotation. Since the operator can determine how far trocar actuation rod (220) has traveled based on audible/tactile feedback from detents (6303) and resilient tab (6302), the operator can determine when a sufficient gap distance (d) is created to facilitate proper release of stapled tissue by counting a predetermined number of audible/tactile clicks associated with a sufficient gap distance (d). Once the predetermined number of audible/tactile clicks are counted, the operator may confirm that a sufficient gap distance (d) has been created to release tissue between surfaces (412, 322) of anvil (400) and stapling head assembly (300). The operator may thus be informed that anvil (400) has reached a position where it is proper to remove instrument (10) from the patient.

Since distal actuation of trocar actuation rod (220) is more relevant than proximal actuation of trocar actuation rod (220) when creating sufficient gap distance (d) to facilitate proper release of stapled tissue, it may be desirable to create a different level of audible/tactile response based on the direction of knob (6304) rotation. However, creating different audible/tactile responses based off direction of knob (6304) rotation is completely optional.

Figure 30A:
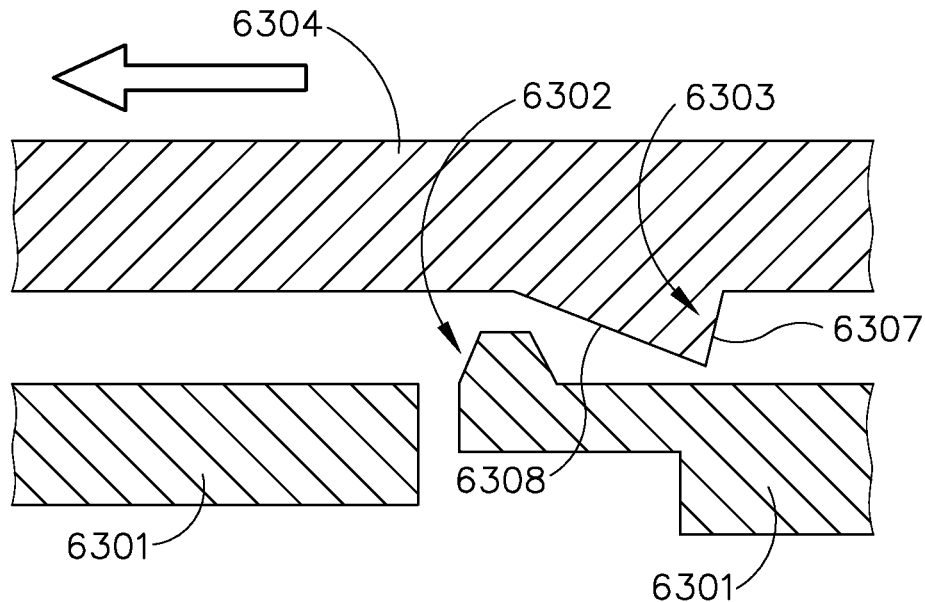
FIG. 30A depicts a top cross-sectional view of the rotation knob and handle of the tissue release indicator system of FIG. 29, with the knob being rotated in a first direction, and with a detent feature of the knob approaching a tab of the handle.
Figure 30B:
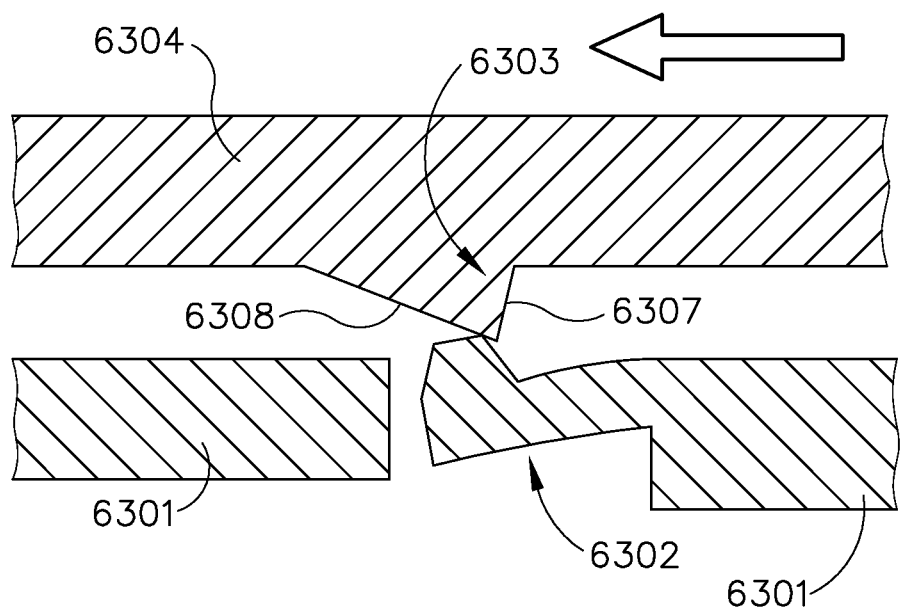
FIG. 30B depicts a top cross-sectional view of the rotation knob and handle of the tissue release indicator system of FIG. 29, with the knob being rotated further in the first direction, with the detent feature engaging the handle.
Figure 30C:
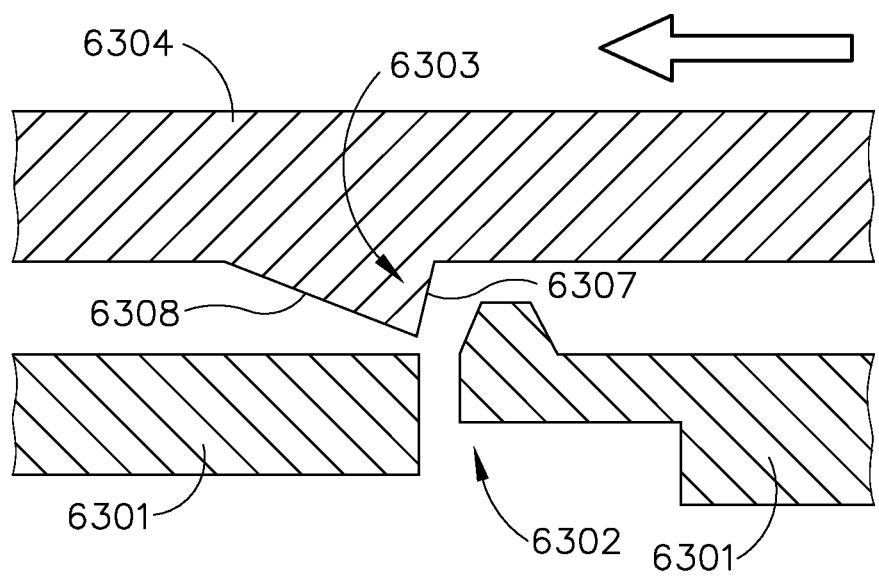
FIG. 30C depicts a top cross-sectional view of the rotation knob and handle of the tissue release indicator system of FIG. 29, with the knob being rotated further in the first direction, with the detent feature disengaging the handle to create an audible click.

As shown in FIGS. 30A-C, annular array of detents (6303) is configured to interact with resilient tab (6302) of handle (6301) to make relatively loud or pronounced clicks when rotation of knob (6304) translates trocar actuation rod (220) in a distal direction. Each detent (6303) is defined by a gradual slope (6308) extending obliquely from the distal face of knob (6304) and a steep slope (6307) extending either normal or obliquely from the distal face of knob (6304). As seen in FIG. 30B when knob (6304) is rotated in a first direction, gradual slope (6308) makes contact with resilient tab (6302), displacing resilient tab a predetermined distance based on the apex of detent (6303). As best seen in FIG. 30C, when gradual slope (6308) of detent (6303) is no longer in contact with resilient tab (6302), resilient tab (6302) pops back into a non-deformed state. However, because of the drastic change in slope between gradual slope (6308) and steep slope (6307), resilient tab (6302) is not gradually released into a non-deformed state, so resilient tab (6302) makes a loud clicking noise. As mentioned above, each time resilient tab (6302) makes this noise, the operator may hear and/or feel the click and thereby understand that trocar actuation rod (220) has traveled a predetermined distance.

Figure 31A:
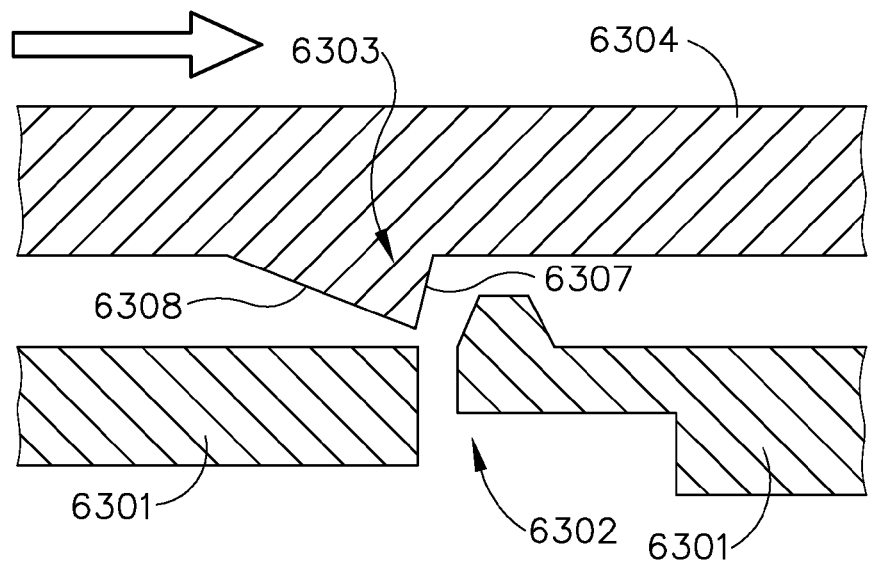
FIG. 31A depicts a top cross-sectional view of the rotation knob and handle of the tissue release indicator system of FIG. 29, with the knob being rotated in a second direction, and with a detent feature of the knob approaching a tab of the handle.
Figure 31B:
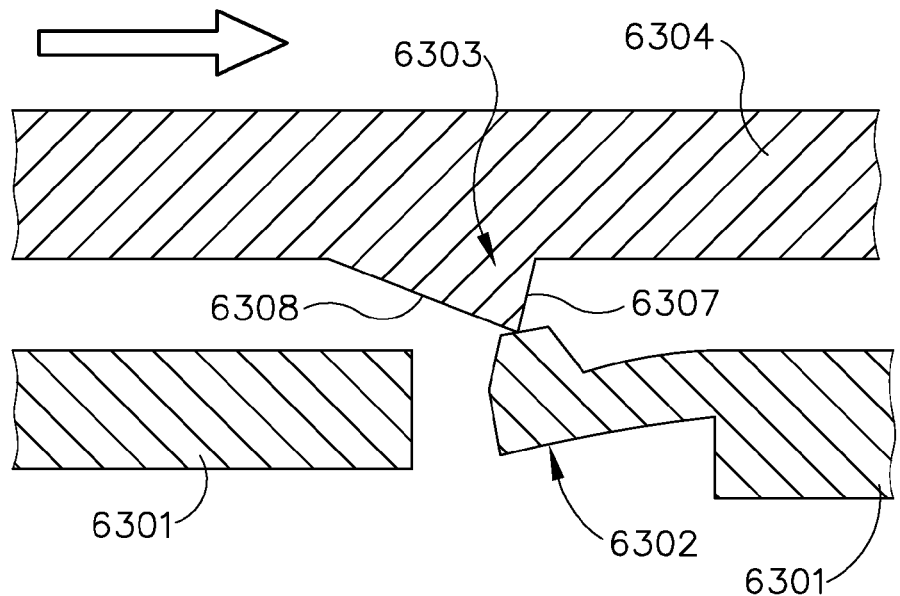
FIG. 31B depicts a top cross-sectional view of the rotation knob and handle of the tissue release indicator system of FIG. 29, with the knob being rotated further in the second direction, with the detent feature engaging the handle.
Figure 31C:
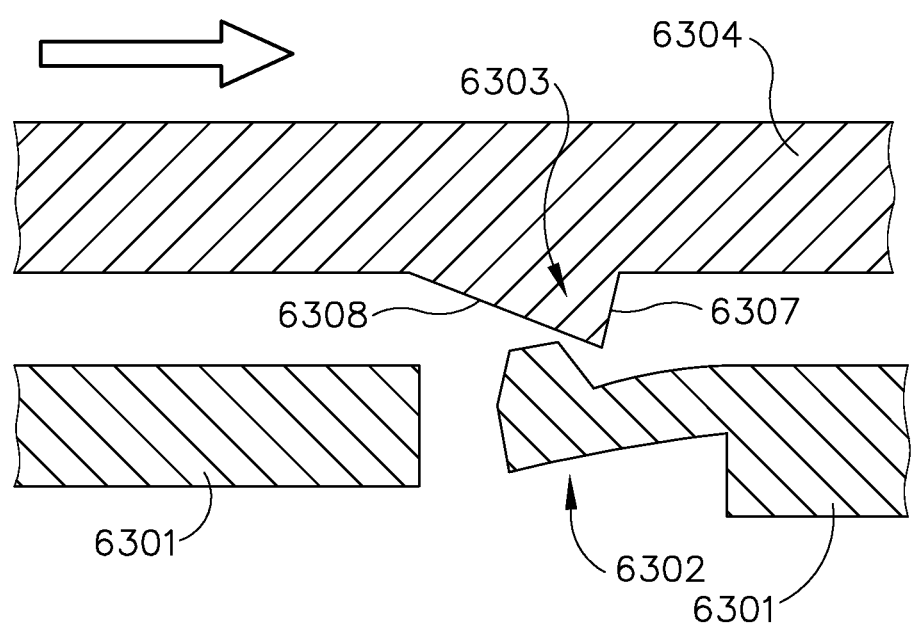
FIG. 31C depicts a top cross-sectional view of the rotation knob and handle of the tissue release indicator system of FIG. 29, with the knob being rotated further in the second direction, with the detent feature disengaging the handle to create an audible click.

As shown in FIGS. 31A-C, annular array of detents (6303) is configured to interact with resilient tab (6302) of handle (6301) to make relatively soft or subdued clicks when rotation of knob (6304) translates trocar actuation rod (220) in a proximal direction. FIGS. 31A-B show knob (6304) rotated in a second direction (opposite to the first direction associated with FIGS. 30A-30C) so that steep slope (6307) displaces resilient tab to the predetermined apex of detent (6303). However, as best seen in FIG. 31C, when steep slope (6307) is no longer in contact with resilient tab (6302), resilient tab (6302) is gradually placed back a non-deformed state through contact with gradual slope (6308). The gradual release of resilient tab (6302) makes a 'soft' click as compared to the 'loud' click when knob (6303) is rotated in the first direction. Therefore, an operator will be able to determine which direction trocar actuation rod (220) is translating based on the sound of the click, and will also be able to determine the distance traveled by trocar actuation rod (220) based on the number of clicks that are heard and/or felt.

C. Hall Effect Sensor Indicator

Figure 32A:
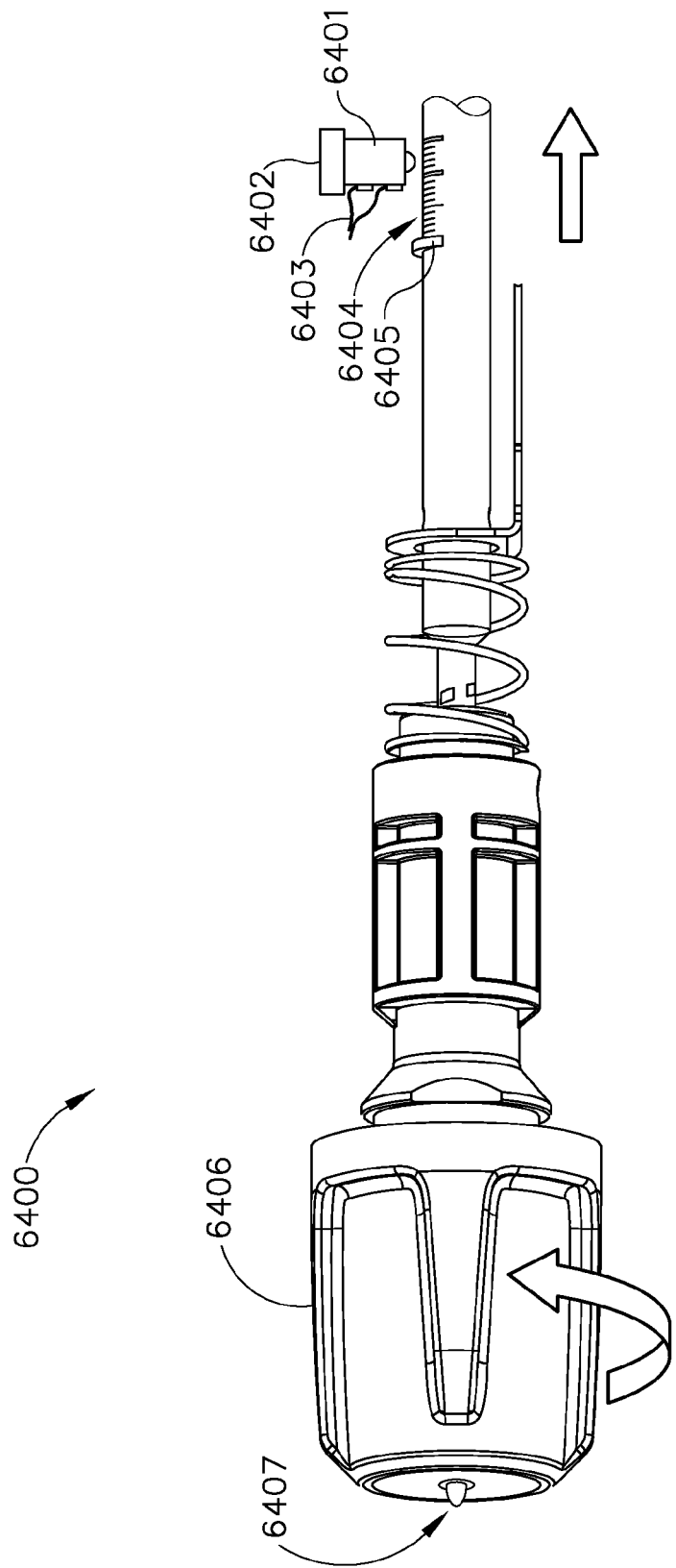
FIG. 32A depicts a side elevational view of an exemplary trocar actuation assembly including a tissue release indicator that may be incorporated into the circular stapler of FIG. 1, with a trocar actuation rod in a proximal longitudinal position and the tissue release indicator in a first state.
Figure 32B:
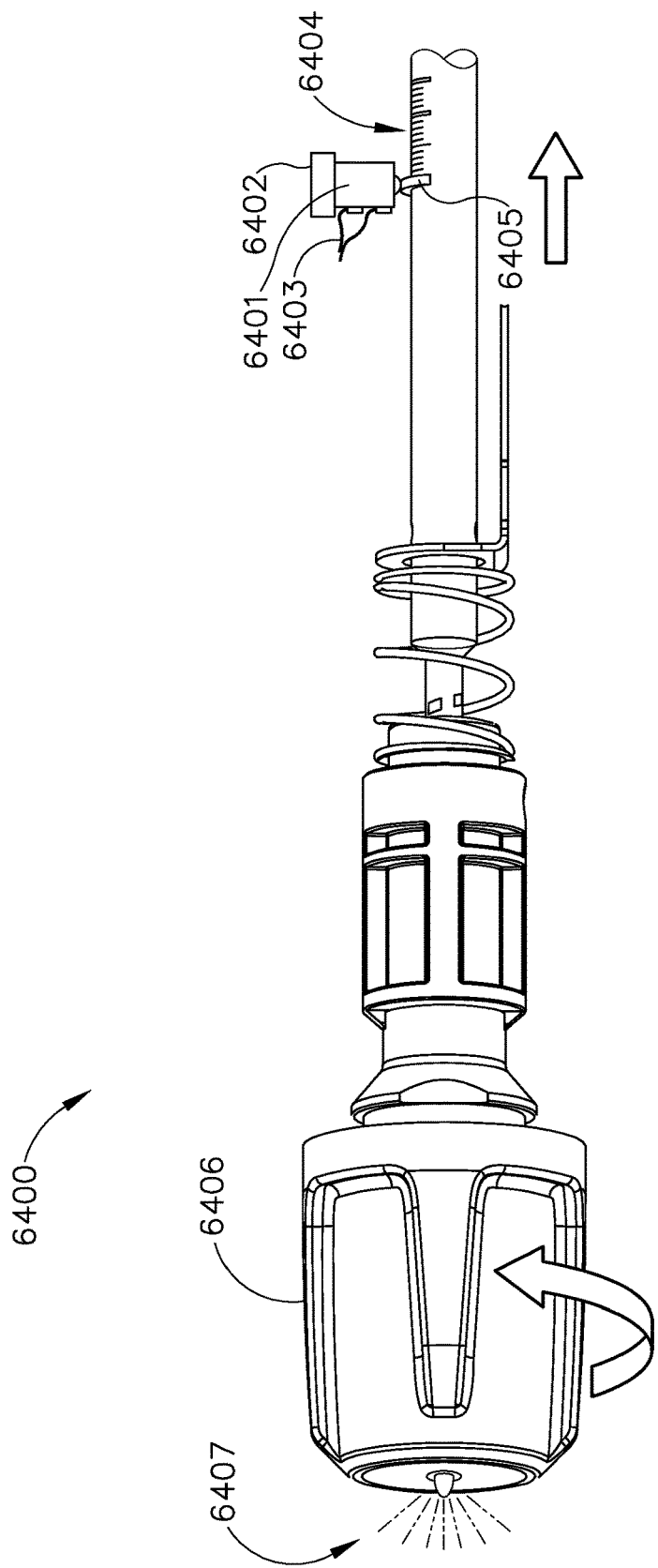
FIG. 32B depicts a side elevational view of the trocar actuation assembly of FIG. 32A, with the trocar actuation rod in a distal position and the tissue release indicator in a second state.

FIGS. 32A-32B depict a hall effect sensor indicator system (6400) that is operable to indicate a sufficient gap distance (d) to facilitate proper release of stapled tissue between surfaces (412, 322) of anvil (400) and stapling head assembly (300). Hall Effect sensor indicator system (6400) may be readily incorporated into instrument (10). Hall Effect sensor indicator system (6400) comprises a Hall Effect sensor (6401), a trocar actuation rod (6404), a magnet (6405), and an indicator (6407) attached to knob (6406). Hall Effect sensor (6401) is fixed relative to a casing (6402). Hall Effect sensor (6401) is connected to indicator (6407) via wiring (6403) such that Hall Effect sensor (6401) effectively acts as a switch to activate indicator (6407) as will be described in greater detail below. Knob (6406), casing (6402), and trocar actuation rod (6404) are substantially the same as knob (130), casing (110), and actuation rod (220) mentioned above. Therefore, it should therefore be understood that trocar (330) will translate longitudinally relative to outer sheath (210) in response to translation of trocar actuation rod (6404) relative to outer sheath (210). Additionally, rotation of knob (6406) translates trocar actuation rod (6404). However, magnet (6405) is strategically fixed to trocar actuation rod (6404) such that Hall Effect sensor (6401) is directly adjacent to magnet when trocar actuation rod (6404) is positioned in such a way to define a sufficient gap distance (d) to facilitate proper release of stapled tissue.

Hall Effect sensor (9401) acts as a switch to turn on indicator (6407). Therefore, when Hall Effect sensor (9401) is not adjacent to magnet, the switch is effectively off, leaving indicator (6407) in an inactivated state. However, when Hall Effect sensor (6401) is directly adjacent to magnet, the switch is effectively on, turning indicator (6407) into an activated state. In the present example, indicator (6407) comprises an LED that illuminates when magnet (6405) actuates Hall Effect sensor (9401). Of course, indicator (6407) may take any other suitable form and may provide feedback to the operator in the form of audible, visual, and/or tactile feedback.

As shown in FIG. 32A, when tissue has been severed and staples administered, an operator may start rotating knob to push trocar actuation rod (6404) in a distal direction to facilitate proper release of stapled tissue. As trocar actuation rod (6404) travels in the distal direction, magnet (6405) travels closer towards Hall Effect sensor (6401). As mentioned above, once magnet (6405) is adjacent to Hall Effect sensor (6401), trocar actuation rod (6404) is positioned in such a way to define a sufficient gap distance (d) to facilitate proper release of stapled tissue. Therefore, Hall Effect sensor (6401) switches indicator (6407) to an activated state, allowing operator to confirm that a sufficient gap distance (d) has been created to release tissue between surfaces (412, 322) of anvil (400) and stapling head assembly (300). The operator may thus be informed that anvil (400) has reached a position where it is proper to remove instrument (10) from the patient.

D. Deployable Audible Mechanism Indicator

Figure 33:
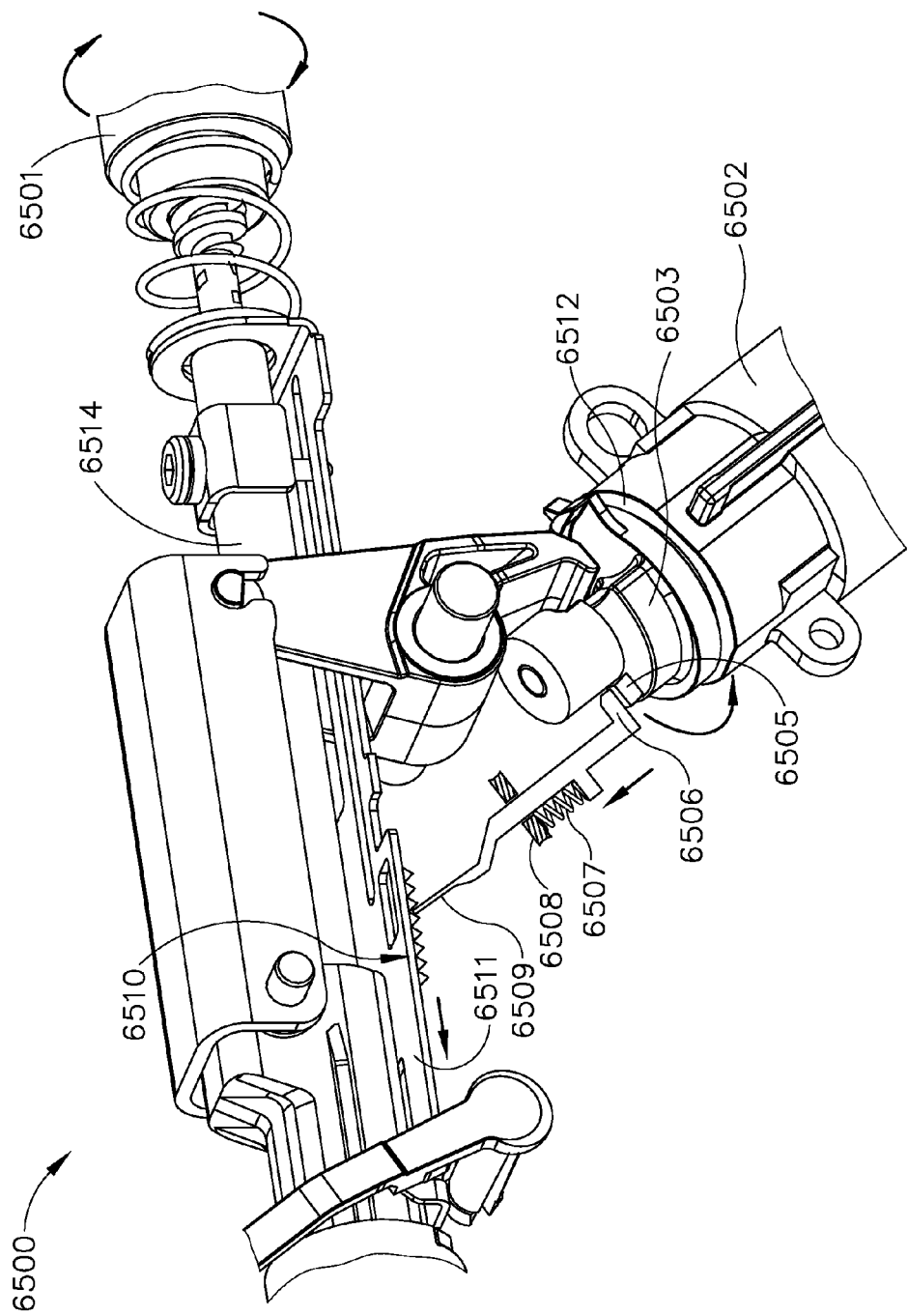
FIG. 33 depicts a perspective view of an exemplary tissue release indicator that may be incorporated into the circular stapler of FIG. 1, where the tissue release indicator comprises a deployable audible/tactile mechanism.
Figure 34A:
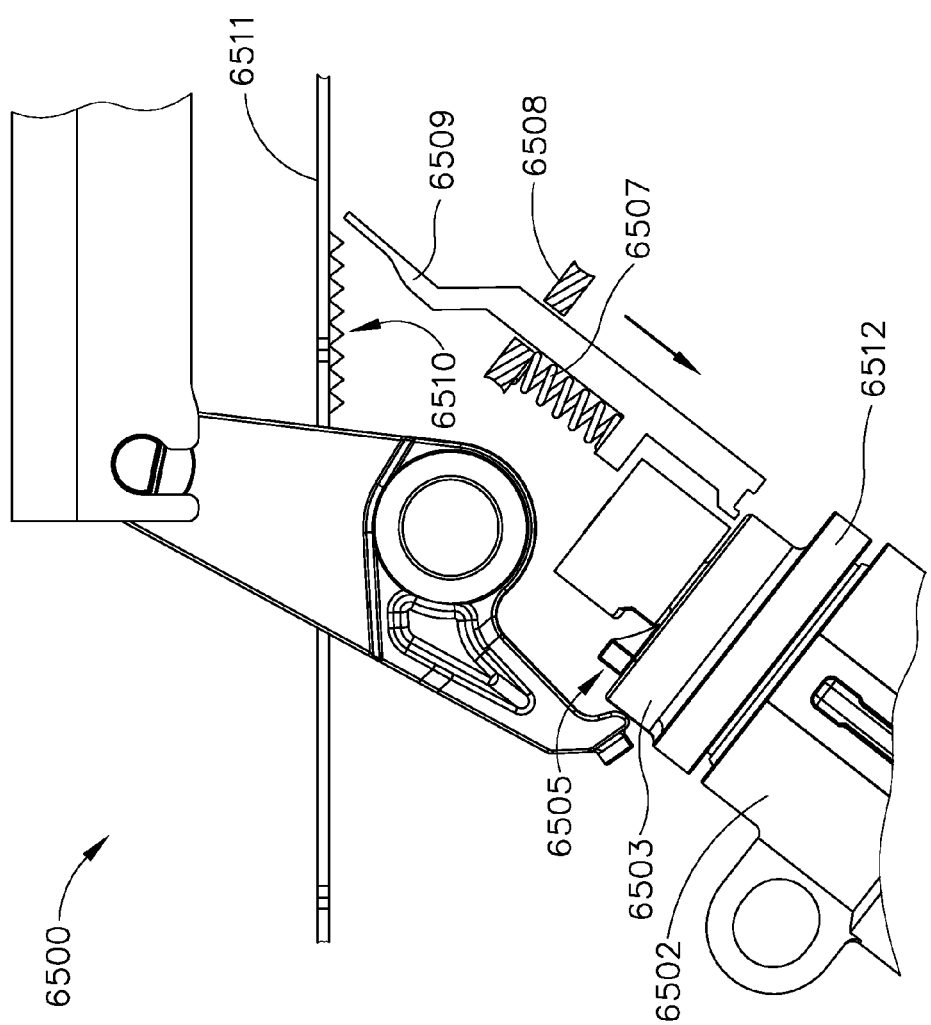
FIG. 34A depicts a side elevational view of the tissue release indicator of FIG. 33 in a pre-deployed position.
Figure 34B:
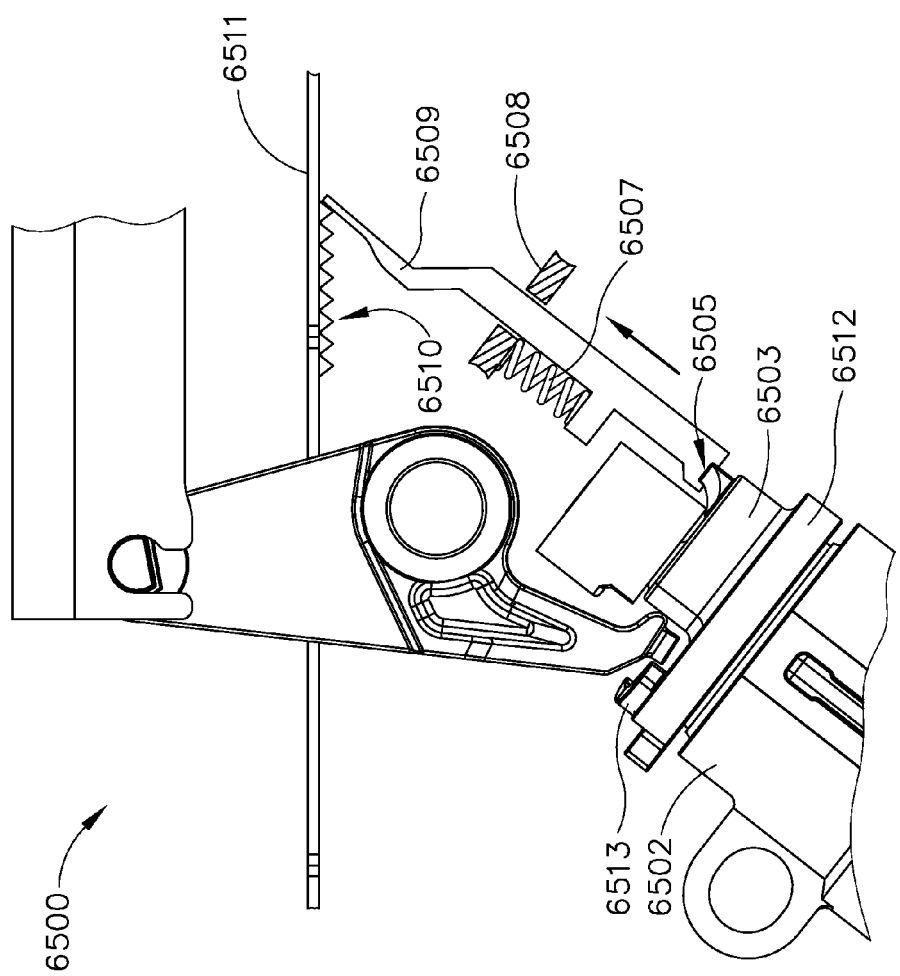
FIG. 34B depicts a side elevational view of the tissue release indicator of FIG. 33 in a deployed position while an associated bracket is stationary.
Figure 34C:
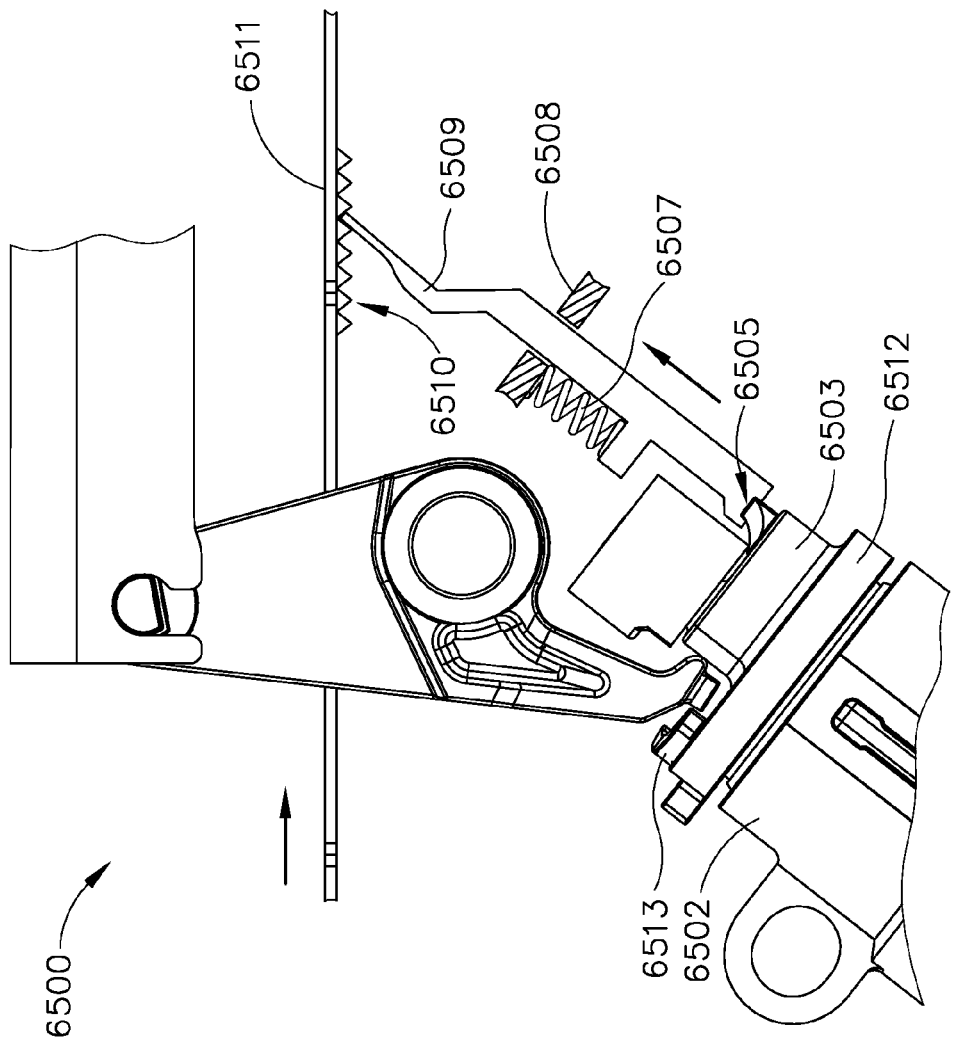
FIG. 34C depicts a side elevational view of the tissue release indicator of FIG. 33 in a deployed position while the bracket is translating longitudinally.

FIGS. 33-34C depict an exemplary deployable indicator system (6500) that provides audible feedback to indicate a sufficient gap distance (d) to facilitate proper release of stapled tissue between surfaces (412, 322) of anvil (400) and stapling head assembly (300). Deployable indicator system (6500) may be readily incorporated into instrument (10). Deployable indicator system (6500) comprises a rotary cam feature (6512) that is driven by gearbox (6502), a clicking mechanism (6509) that is slidably coupled to casing (6508), a resilient member (6507) with one end engaging clicking mechanism (6509) and one end fixed to casing (6508), and a bracket (6511). Gearbox (6502) is substantially similar to gearbox (162) in the fact gearbox (6502) is driven by motor (not shown) and drives rotary cam member (6512) to drive stapling head assembly (300).

Rotary cam member (6512) in substantially similar to rotary cam member (700) described above. Rotary cam member (6512) comprises a first cam feature (6503), a second cam feature (6513), and a third cam feature (not shown) substantially similar to the first cam feature (710), second cam feature (720), and a third cam feature (730) of rotary cam member (700), respectively. However, unlike cam member (700) described above, cam member (6512) of the present example comprises an additional fourth cam feature (6505). As best seen in FIGS. 34A-34C, fourth cam feature (6505) slopes in a radial path on top of first cam feature (6503) in such a way that the sloped face of fourth cam feature (6505) engages the proximal end of clicking mechanism (6509) when rotary cam member (6512) is driven by gearbox (6502).

Bracket (6511) is substantially similar to bracket (500) described above. Bracket (6511) is configured and positioned to translate longitudinally in response to movement of trocar actuation rod (6514). Trocar actuation rod (6514) is substantially similar to trocar actuation rod (220) described above. It should therefore be understood that trocar (330) and anvil (400) will translate longitudinally relative to outer sheath (210) in response to translation of trocar actuation rod (6514) relative to outer sheath (210). Unlike bracket (500) described above, bracket (6511) of the present example also comprises a set of teeth (6510) positioned in a longitudinally extending array that is parallel with the longitudinal direction defined by trocar actuation rod (6514). As will be described in greater detail below, teeth (6510) are configured to engage clicking mechanism (6509) when clicking mechanism (6509) is in a deployed position.

As noted above, clicking mechanism (6509) is slidably coupled to casing (6508) in such a way that clicking mechanism (6509) can slide along a linear path. Resilient member (6507) has one end fixed to casing (6508) and another end fixed to clicking mechanism (6509). As best seen in FIG. 34A, resilient member (6507) biases clicking mechanism (6509) toward cam feature (6505) and away from bracket (6511) so that clicking mechanism (6509) is resiliently biased to disengage from linear array of teeth (6510) in a pre-deployed position.

FIGS. 34A-34C depict the above-described components at various stages of operation. FIG. 34A shows deployable indicator system (6500) in a pre-deployed position. In a pre-deployed position, clicking mechanism (6509) is biased in a proximal position away from bracket (6511). Rotary cam member (6512) is positioned in a similar position as that of cam member (700) shown in FIGS. 18A, 19A, and 20A. Therefore, at this stage, knife member (340) and staple driver member (350) are in proximal positions, such that stapling head assembly (300) is in a non-actuated state.

FIG. 34B shows deployable indicator system (6500) in a post-deployed position. In a post-deployed position, rotary cam member (6512) is positioned in a similar position as that of cam member (700) shown in FIG. 20D. Therefore, at this state, knife member (340) and staple driver member (350) have been actuated both distally and proximally, completing the cutting and stapling motion. However, as noted above, fourth cam feature (6505) has been rotated such that the sloped face of fourth cam feature (6505) engages clicking mechanism (6509), thereby displacing clicking mechanism (6509) in a distal direction toward bracket (6511) in opposition to the bias provided by resilient member (6507). It is important to note, at this point, clicking mechanism (6509) is positioned at a level capable of interacting with linear array of teeth (6510) if bracket (6511) is translated longitudinally.

FIG. 34C shows deployable indicator system (6500) in a post-deployed position while bracket (6511) is being actuated via trocar actuation rod (6514) and knob (130). As can be seen, the distal end of clicking mechanism (6509) is in contact with linear array of teeth (6510) such that linear actuation of bracket (6511) drags teeth (6510) over clicking mechanism (6509) to make an audible noise. In other words, clicking mechanism (6509) provides a pawl that ratchets along teeth (6510) as bracket (6511) translates longitudinally. Teeth (6510) may be positioned along bracket (6511) such that any audible clicking between teeth (6510) and deployed clicking mechanism (6509) indicate to the operator that a sufficient gap distance (d) has been created to release tissue between surfaces (412, 322) of anvil (400) and stapling head assembly (300), signaling that removal of instrument is proper. Additionally, teeth (6510) may be positioned along bracket (65111) such that a predetermined number of clicks between teeth (6510) and deployed clicking mechanism (6509) will indicate to the operator that a sufficient gap distance (d) has been created to release tissue between surfaces (412, 322) of anvil (400) and stapling head assembly (300), thereby indicating that that removal of instrument (10) from the patient is proper.

E. Increased Resistance Indicator

Figure 35:
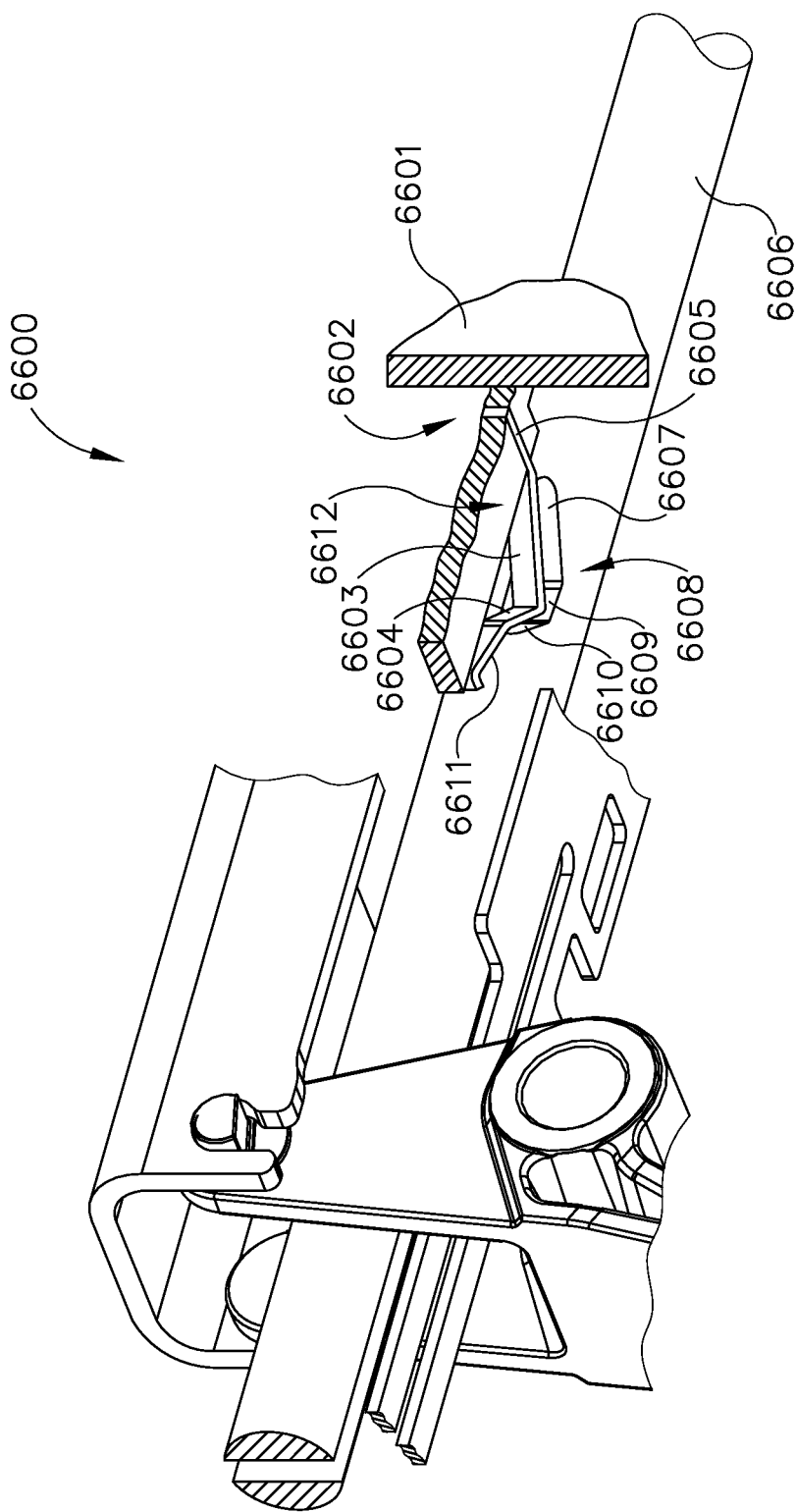
FIG. 35 depicts a prospective view of an exemplary resistance based tissue release indicator that may be incorporated into the circular stapler of FIG. 1.
Figure 36A:
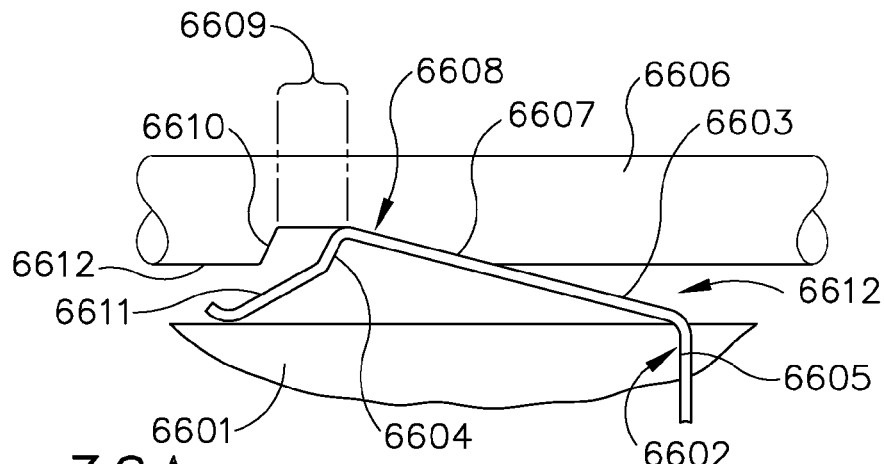
FIG. 36A depicts a side elevational view of the resistance based tissue release indicator of FIG. 35 with a trocar actuation rod in a first longitudinal position.
Figure 36B:
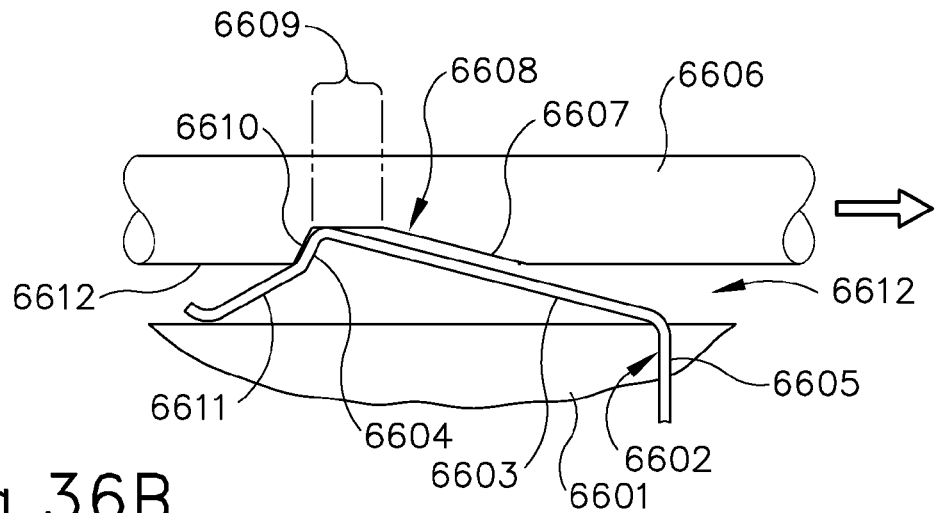
FIG. 36B depicts a side elevational view of the resistance based tissue release indicator of FIG. 35 with a trocar actuation rod in a second longitudinal position.
Figure 36C:
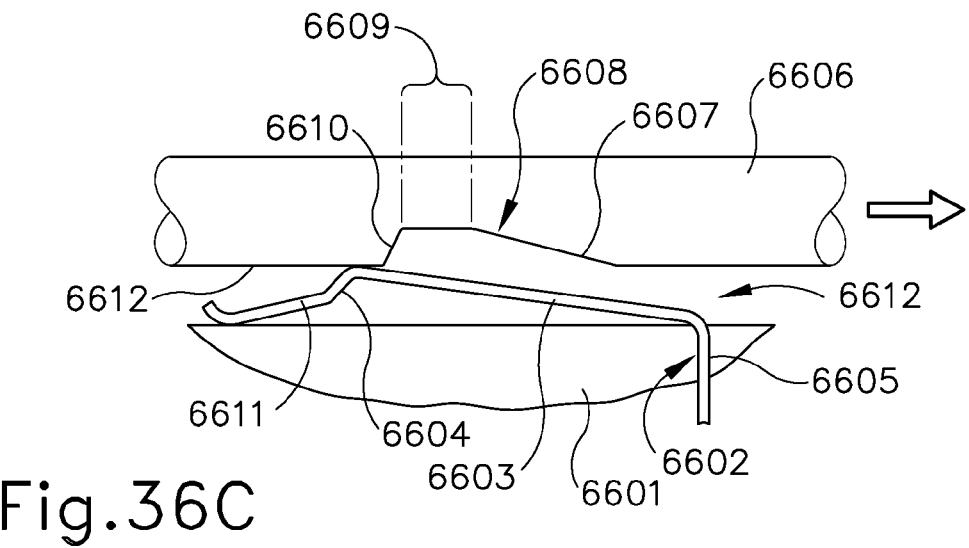
FIG. 36C depicts a side elevational view of the resistance based tissue release indicator of FIG. 35 with a trocar actuation rod in a third longitudinal position.

FIGS. 35-36C depict an exemplary resistance indicator system (6600) that is operable to indicate a sufficient gap distance (d) to facilitate proper release of stapled tissue between surfaces (412, 322) of anvil (400) and stapling head assembly (300). Resistance system (6600) may be readily incorporated into instrument (10). Resistance indicator system (6600) comprises a trocar actuation rod (6606) and a resistance spring (6612) that is partially fixed to a casing (6601). Trocar actuation rod (6606) is substantially similar to trocar actuation rod (220) described above. It should therefore be understood that trocar (330) and anvil (400) will translate longitudinally relative to outer sheath (210) in response to translation of trocar actuation rod (6606) relative to outer sheath (210). Unlike trocar actuation rod (220), trocar actuation rod (6606) of the present example defines a cutout (6608) comprising an angled guide surface (6607), a flat surface (6609), and a resistant surface (6610). Both resistant surface (6610) and guide surface (6607) slope inwardly toward flat surface (6609) from exterior (6612) of trocar actuation rod (6606).

Resistance spring (6612) comprises a fixed member (6605) located within a channel (6602) of casing (6601), a distal leg (6603), a proximal leg (6611), and a deforming surface (6604) in between distal leg (6603) and proximal leg (6611). Resistance spring (6612) is configured to deform is response to distal actuation of trocar actuation rod (6606) as will be described in greater detail below.

FIGS. 36A-36C depict the above-described components at various stages of operation. FIG. 36A shows resistance indicator system (6600) at a state where knife member (340) and staple driver member (350) have been actuated both distally and proximally, completing the cutting and stapling motion but before the gap distance (d) has been enlarged to facilitate release of stapled tissue between surfaces (412, 322). At this state, distal leg (6603) of resistance spring (6605) is in contact with guide surface (6607) of cutout (6608). Guide surface (6607) is in contact with distal leg (6603) until the apex of resistance spring (6612) is in contact with flat surface (6009). However, it is important to note that guide surface (6607) does not need to be in contact with distal leg (6603) at this stage.

As trocar actuation rod (6606) is advanced distally in order to enlarge gap distance (d) for removal of tissue between surfaces (412, 322), the apex of resistance spring (6612) contacts flat surface (6009) while distal leg (6603) is no longer in contact with guide surface (6607). Fixed member (6605) of resistance spring (6612) prevents resistance spring (6612) from translating distally with trocar actuation rod (6606). Trocar actuation rod (6606) is further advanced distally until deforming surface (6604) makes contact with resistance surface (6610) as shown in FIG. 36B.

Resistant surface (6610) is positioned on trocar actuation rod (6606) to make contact with deforming surface (6604) of spring (6612) when a sufficient gap distance (d) has been created. As a result of resistant surface (6610) making contact with deforming surface, the operator will then feel an increased resistance while turning knob (130) to translate trocar actuation rod (6606) further distally. This increase is resistance occurs because resistant surface (6610) of trocar actuation rod (6606) must exert additional force to deform resistance spring (6612). Resistant surface (6610) is sloped in such a manner as to push resistance spring (6612) downwardly as trocar actuation rod (6606) travels further distally. Resistance spring (6612) has sufficient column strength not to buckle when forced by actuation of resistance surface (6610). At this stage, the additional resistance provided by spring (6612) and cutout (6608) provide tactile feedback to the operator, indicating that trocar actuation rod (6606) has been advanced to a distance that provides a sufficiently large gap between surfaces (412, 322) to facilitate removal of instrument (10) from the patient.

In the event that the operator drives trocar actuation rod (6606) further distally from the position shown in FIG. 36B, resistance surface (6610) and deforming surface (6604) will cooperate to eventually transition spring (6612) to a collapsed state as shown in FIG. 36C. When spring (6612) reaches this collapsed state, the resistance to further rotation of knob (130) may drop suddenly. This sudden drop of resistance to knob (130) rotation may provide further tactile feedback to the operator indicating that trocar actuation rod (6606) has been advanced to a distance that provides a sufficiently large gap between surfaces (412, 322) to facilitate removal of instrument (10) from the patient. In some instances, though, the operator may remove instrument (10) from the patient when the above described components are in the state shown in FIG. 36B, such that the components do not ever reach the state shown in FIG. 36C.

F. Dual Mode Visual Indicator

Figure 37:
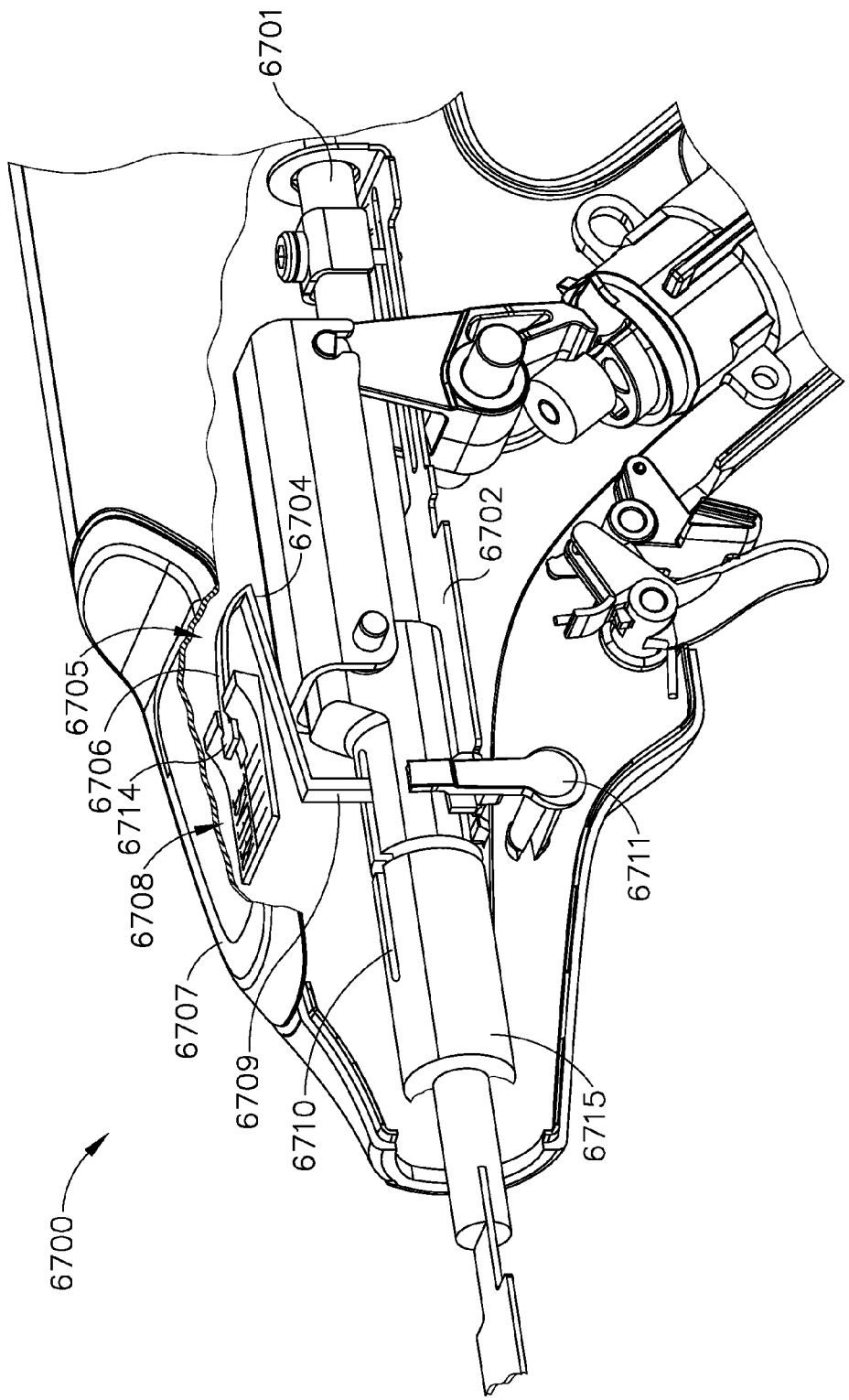
FIG. 37 depicts a perspective cut away view of an exemplary visual based tissue release indicator that may be incorporated into the circular stapler of FIG. 1.
Figure 38A:
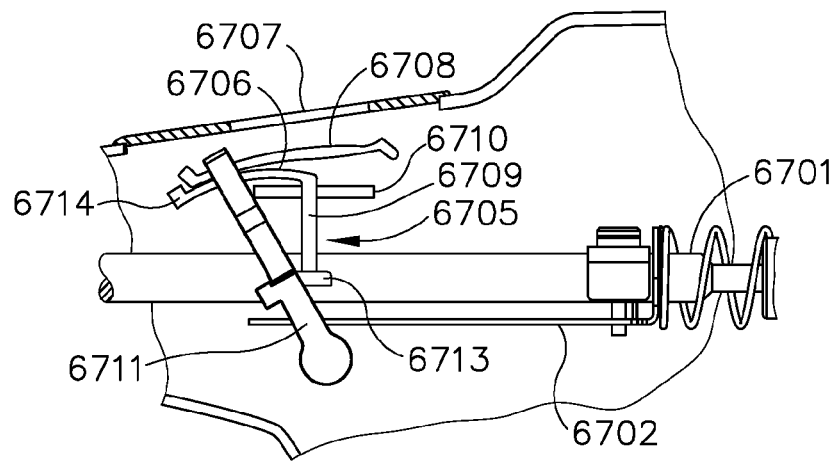
FIG. 38A depicts a side elevational view of the visual based tissue release indicator of FIG. 37, with a portion of the casing removed, and with a trocar actuation rod in a first longitudinal position.
Figure 38B:
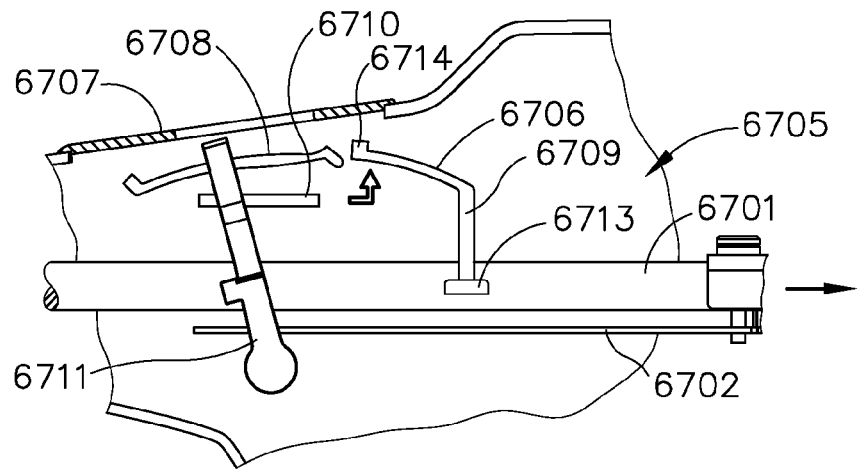
FIG. 38B depicts a side elevational view of the visual based tissue release indicator of FIG. 37, with a portion of the casing removed, and with a trocar actuation rod in a second longitudinal position.
Figure 38C:
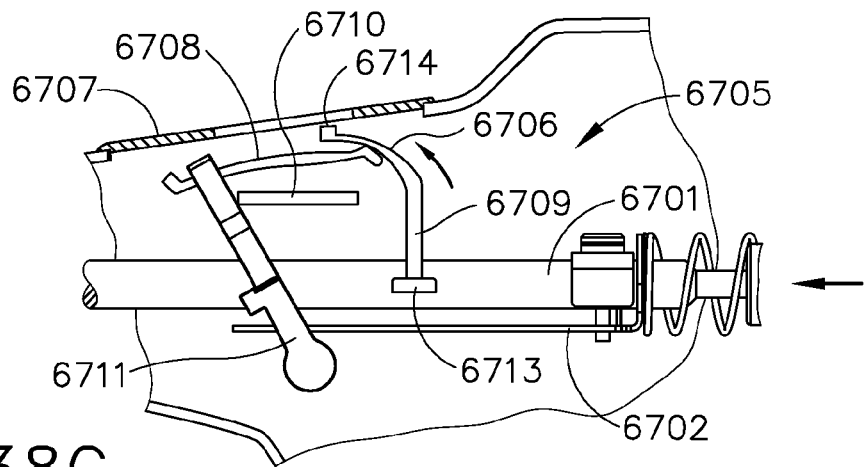
FIG. 38C depicts a side elevational view of the visual based tissue release indicator of FIG. 37, with a portion of the casing removed, and with a trocar actuation rod in a third longitudinal position.
Figure 39:
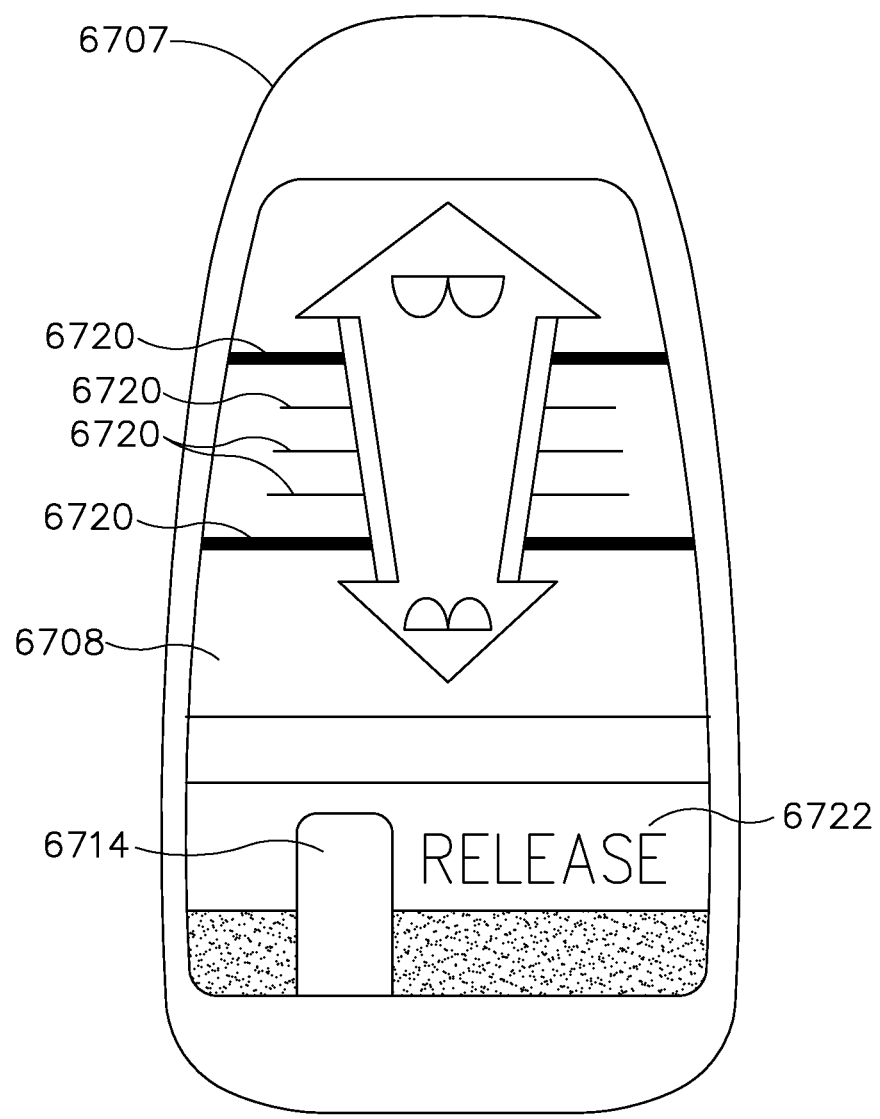
FIG. 39 depicts a top elevational view of the visual window used in the visual based tissue release indicator of FIG. 37.

FIGS. 37-39 depict an exemplary indicator system (6700) that is configured to provide another form of visual feedback to indicate a sufficient gap distance (d) to facilitate proper release of stapled tissue between stapling head assembly (300) and anvil (400). Indicator system (6700) may be readily incorporated into instrument (10). Indicator system (6700) comprises an indicator window (6707), an indicator panel (6708), a backlight (6708), a pivoting indicator member (6711), and a tissue release indicator (6705).

Indicator window (6707) is substantially the same as window (114) described above. Indicator member (6711) is positioned between indicator window (6707) and indicator panel (6708). Indicator member (6711) is substantially the same as indicator member (520) described above. Indicator member (6711) is configured to pivot in response to translation of a bracket (6702), which is substantially the same as bracket (500) described above. Bracket (6702) is configured to translate in response to translation of a trocar actuation rod (6701), which is substantially the same as trocar actuation rod (220) described above.

It should be understood from the foregoing that the operator may view indicator member (6711) through window (6707) to determine whether the gap distance (d) is within the appropriate range before the operator actuates stapling head assembly (300). As shown in FIG. 39, indicator panel (6708) may provide fixed indicia (6720) that provide reference points for the operator to view the moving indicator member (6711) against. Backlight (6708) may provide illumination that facilitates viewing of indicator member (6711) against indicator panel (6708) through indicator window (6707). FIGS. 38A-38B show indicator member (6711) moving above indicator member (6711) in response to proximal movement of trocar actuation rod (6701) and bracket (6702) as the operator adjusts the gap distance (d) between opposing surfaces (412, 322) of anvil (400) and stapling head assembly (300) before actuating stapling head assembly (300).

Tissue release indicator (6705) is fixed to trocar actuation rod (6701). Tissue release indicator (6705) comprises an anchor portion (6713), a stem (6709), an optional extension arm (6704), a spring arm (6706), and a distal tab (6714). Anchor portion (6713) is fixedly secured to trocar actuation rod (6701). Stem (6709) projects upwardly from anchor portion (6713) through a slot (6710) formed in a stapling head assembly driver (6715). Slot (6710) of stapling head assembly driver (6715) provides sufficient clearance for stem (6709) that enables tissue release indicator (6705) and trocar actuation rod (6701) to move together independently relative to stapling head assembly driver (6715). As shown in FIG. 37, extension arm (6704) may be provided to extend proximally to secure spring arm (6706) to stem (6709). Alternatively, as shown in FIGS. 38A-38C, spring arm (6706) may be secured directly to stem (6709). In both versions, distal tab (6714) is provided at the free distal end of spring arm (6706).

Spring arm (6706) is resiliently biased to urge distal tab (6714) upwardly toward window (6707). However, during the initial stages of operation before anvil (400) is retracted to bring surfaces (412, 322) within the appropriate range of gap distance (d) to actuate stapling head assembly (300), distal tab (6714) is positioned underneath indicator panel (6708) and is thus obscured by indicator panel (6708) as shown in FIG. 38A. The stage of operation shown in FIG. 38A corresponds with the stages of operation shown in FIGS. 21A-21B as described above.

Once anvil (400) is retracted to a position where surfaces (412, 322) are within the appropriate range of gap distance (d) to actuate stapling head assembly (300), distal tab (6714) clears the proximal end of indicator panel (6708), such that spring arm (6706) drives distal tab (6714) upwardly as shown in FIG. 38B. At this stage, the operator will actuate stapling head assembly (300) as described above. The stage of operation shown in FIG. 38B thus corresponds with the stages of operation shown in FIGS. 21C-21D as described above.

After stapling head assembly (300) is actuated, the operator may wish to advance anvil (400) distally to increase the gap distance (d), to thereby facilitate release of the tissue between surfaces (412, 322), to thereby facilitate removal of instrument (10) from the patient as described above in relation to FIG. 21E. As the operator advances anvil (400) distally via trocar actuation rod (6701), distal tab (6714) also travels distally. As shown in FIG. 38C, distal tab (6714) is positioned between window (6707) and indicator panel (6708) as distal tab (6714) travels distally during this stage of operation. The operator may thus visually observe the position of distal tab (6714) against indicator panel (6708) through window (6707) in order to receive visual feedback that is indicative of the expanded gap distance (d). Referring back to FIG. 39, the associated region of indicator panel (6708) may provide fixed indicia (6722) that serve as reference points for the operator to view the moving distal tab (6714) against. Again, backlight (6708) may provide illumination that facilitates viewing of distal tab (6714) against indicator panel (6708) through indicator window (6707).

It should be understood from the foregoing that indicator panel (6708) is configured to provide two different kinds of visual feedback—one indicating whether a suitable gap distance (d) has been achieved before stapling head assembly (300) has been actuated; and another indicating whether the gap distance (d) has been sufficiently increased to facilitate release of the tissue between surfaces (412, 322), to thereby facilitate removal of instrument (10) from the patient. It should be understood that the example of indicator panel (6708) shown in FIG. 39 is merely illustrative. Various other suitable forms that indicator panel (6708) may take will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body; (b) a shaft assembly extending distally from the body; (c) a stapling head assembly located at the distal end of the shaft assembly, wherein the stapling head assembly comprises a distal surface, wherein the stapling head assembly is operable to drive an annular array of staples through the distal surface; (d) an anvil, wherein the anvil is configured to couple with the stapling head assembly; (e) an anvil adjustment assembly, wherein the anvil adjustment assembly comprises a translating member, wherein the translating member is operable to translate relative to the body along a longitudinal axis to thereby adjust a gap distance between the anvil and the distal surface of the stapling head assembly; and (f) a first indicator assembly, wherein the first indicator assembly comprises: (i) a first member, wherein the first member is configured to translate in response to translation of the translating member relative to the body, and (ii) a second member, wherein the second member is configured to remain stationary relative to the body as the first member translates relative to the body, wherein the first indicator assembly is configured to provide feedback indicating whether the gap distance is sized to release tissue from between the anvil and the distal surface based on positioning of the first member in relation to the second member.

Example 2

The surgical instrument of Example 1, wherein the first member comprises an array of markers.

Example 3

The surgical instrument of Example 2, wherein the markers are configured to successively translate past the second member.

Example 4

The surgical instrument of Example 3, wherein the second member comprises a switch, wherein the markers are configured to successively actuate the switch as the markers successively translate past the switch.

Example 5

The surgical instrument of any one or more of Examples 3 through 4, wherein the first indicator assembly is operable to count a number of markers translating past the second member, wherein the first indicator assembly is configured to provide feedback indicating whether the gap distance is sized to release tissue from between the anvil and the distal surface based on the number of markers counted as translating past the second member.

Example 6

The surgical instrument of any one or more of Examples 1 through 5, further comprising a second indicator assembly, wherein the second indicator assembly is configured to indicate whether the stapling head assembly has been actuated to drive an annular array of staples through the distal surface.

Example 7

The surgical instrument of Example 6, further comprising a staple driving actuator, wherein the second indicator assembly is configured to indicate whether the stapling head assembly has been actuated to drive an annular array of staples through the distal surface based on a position of the staple driving actuator in relation to the body.

Example 8

The surgical instrument of Example 7, wherein the second indicator assembly comprises a window formed in the body, wherein the window is configured to provide a visual path for observation of movement of a portion of the staple driving actuator.

Example 9

The surgical instrument of any one or more of Examples 7 through 8, wherein the second indicator assembly comprises: (i) a light, and (ii) a switch, wherein the switch is configured to activate the light in response to movement of the staple driving actuator.

Example 10

The surgical instrument of any one or more of Examples 1 through 9, wherein the translating member comprises a rod.

Example 11

The surgical instrument of Example 10, wherein the first member comprises a bracket, wherein the bracket is configured to translate relative to the body in response to translation of the rod relative to the body.

Example 12

The surgical instrument of any one or more of Examples 1 through 11, further comprising a second indicator assembly, wherein the second indicator assembly comprises: (i) the first member, and (ii) a third member, wherein the first member is configured to drive the third member to thereby indicate whether the gap distance is sized to staple tissue between the anvil and the distal surface based on positioning of the first member in relation to the body.

Example 13

The surgical instrument of Example 12, wherein the third member is configured to pivot in response to translation of the first member, wherein the third member comprises an indicator needle.

Example 14

The surgical instrument of any one or more of Examples 12 through 13, further comprising a display, wherein the display is configured to provide visual feedback from the second indicator assembly during a first range of motion of the first member, wherein the display is not configured to provide visual feedback from the first indicator assembly during the first range of motion of the first member, wherein the display is configured to provide visual feedback from the first indicator assembly during a second range of motion of the first member.

Example 15

The surgical instrument of any one or more of Examples 1 through 14, wherein the first indicator assembly comprises a light, wherein the first indicator assembly is configured to illuminate the light in response to positioning of the first member in relation to the second member indicating that the gap distance is sized to release tissue from between the anvil and the distal surface.

Example 16

The surgical instrument of any one or more of Examples 1 through 15, wherein the first member comprises a magnet, wherein the second member comprises a Hall Effect sensor.

Example 17

The surgical instrument of any one or more of Examples 1 through 16, wherein the first member comprises a set of teeth, wherein the second member comprises a pawl configured to ratchet along the teeth.

Example 18

The surgical instrument of any one or more of Examples 1 through 17, further comprising a manual input feature operable to drive the translating member longitudinally, wherein the first indicator assembly is configured to provide increased resistance to movement of the manual input feature in response to positioning of the first member in relation to the second member indicating that the gap distance is sized to release tissue from between the anvil and the distal surface.

Example 19

A surgical instrument comprising: (a) a body; (b) a shaft assembly extending distally from the body; (c) a stapling head assembly located at the distal end of the shaft assembly, wherein the stapling head assembly comprises a distal surface, wherein the stapling head assembly is operable to drive an annular array of staples through the distal surface; (d) an anvil, wherein the anvil is configured to couple with the stapling head assembly; (e) a firing assembly, wherein the firing assembly is operable to actuate the stapling head assembly to thereby drive the staples through the distal surface toward the anvil, wherein the firing assembly comprises a motor; (f) a power source, wherein the power source is operable to provide power to the motor; (g) a control module in communication with the power source and the motor, wherein the control module is operable to monitor electrical current communicated from the power source to the motor; and (h) an indicator in communication with the control module, wherein the control module is configured to activate the indicator in response to monitored current indicating completion of a firing stroke by the firing assembly.

Example 20

A surgical instrument comprising: (a) a body; (b) a shaft assembly extending distally from the body; (c) a stapling head assembly located at the distal end of the shaft assembly, wherein the stapling head assembly comprises a distal surface, wherein the stapling head assembly is operable to drive an annular array of staples through the distal surface; (d) an anvil, wherein the anvil is configured to couple with the stapling head assembly; (e) an anvil adjustment assembly, wherein the anvil adjustment assembly comprises a translating member, wherein the translating member is operable to translate relative to the body along a longitudinal axis to thereby adjust a gap distance between the anvil and the distal surface of the stapling head assembly; and (f) an indicator assembly, wherein the first indicator assembly comprises: (i) an array of discrete marker elements, (ii) a sensor, wherein the marker elements are configured to successively activate the sensor in response to translation of the translating member, and (iii) an indicator, wherein the indicator is configured to provide feedback indicating whether the gap distance is sized to release tissue from between the anvil and the distal surface based on activation of the sensor by the marker elements.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, now U.S. Pat. No. 9,572,573, issued Feb. 21, 2017, the disclosure of which is incorporated by reference herein; U.S. Pub. No. 2014/0144968, entitled "Surgical Staple with Integral Pledget for Tip Deflection," published May 29, 2014, now U.S. Pat. No. 9,289,207, issued Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, now U.S. Pat. No. 9,498,222, issued Nov. 22, 2016, the disclosure of which is incorporated by reference herein; U.S. Pub. No. 2014/0151430, entitled "Circular Anvil Introduction System with Alignment Feature," published Jun. 5, 2014, now U.S. Pat. No. 9,724,100, issued Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, now U.S. Pat. No. 9,532,783, issued Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, now U.S. Pat. No. 9,597,081, issued Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, now U.S. Pat. No. 9,463,022, issued Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, now U.S. Pat. No. 8,408,439, issued Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
    (a) a body;
    (b) a shaft assembly extending distally from the body;
    (c) a stapling head assembly located at the distal end of the shaft assembly, wherein the stapling head assembly comprises a distal surface, wherein the stapling head assembly is operable to drive an annular array of staples through openings formed in the distal surface;
    (d) an anvil, wherein the anvil is configured to couple with the stapling head assembly;
    (e) an anvil adjustment assembly, wherein the anvil adjustment assembly comprises a translating member, wherein the translating member is operable to translate relative to the body along a longitudinal axis to thereby adjust a gap distance between the anvil and the distal surface of the stapling head assembly;
    (f) a first indicator assembly, wherein the first indicator assembly comprises:
        (i) a first member comprising an array of markers, wherein the first member is configured to translate in response to translation of the translating member relative to the body, and
        (ii) a second member, wherein the second member is configured to remain stationary relative to the body as the first member translates relative to the body, wherein the first indicator assembly is configured to provide feedback indicating whether the gap distance is sized to release tissue from between the anvil and the distal surface based on positioning of the first member in relation to the second member; and
    (g) a second indicator assembly comprising an arm pivotably coupled with the body, wherein the first member is configured pivot the arm relative to the body to indicate whether the gap distance is sized to staple tissue between the anvil and the distal surface based on position of the first member in relation to the arm.

2. The surgical instrument of claim 1, wherein the markers are configured to successively translate past the second member.

3. The surgical instrument of claim 2, wherein the second member comprises a switch, wherein the markers are configured to successively actuate the switch as the markers successively translate past the switch.

4. The surgical instrument of claim 2, wherein the first indicator assembly is operable to count a number of markers translating past the second member, wherein the first indicator assembly is configured to provide feedback indicating whether the gap distance is sized to release tissue from between the anvil and the distal surface based on the number of markers counted as translating past the second member.

5. The surgical instrument of claim 1, further comprising a third indicator assembly, wherein the third indicator assembly is configured to indicate whether the stapling head assembly has been actuated to drive an annular array of staples through the distal surface.

6. The surgical instrument of claim 5, further comprising a staple driving actuator, wherein the third indicator assembly is configured to indicate whether the stapling head assembly has been actuated to drive an annular array of staples through the distal surface based on a position of the staple driving actuator in relation to the body.

7. The surgical instrument of claim 6, wherein the third indicator assembly comprises a window formed in the body, wherein the window is configured to provide a visual path for observation of movement of a portion of the staple driving actuator.

8. The surgical instrument of claim 6, wherein the third indicator assembly comprises:
   (i) a light, and
   (ii) a switch, wherein the switch is configured to activate the light in response to movement of the staple driving actuator.

9. The surgical instrument of claim 1, wherein the first member comprises a bracket, wherein the bracket is configured to translate relative to the body in response to translation of the rod relative to the body.

10. The surgical instrument of claim 1, wherein the arm comprises an indicator needle.

11. The surgical instrument of claim 1, further comprising a display,
   wherein the display is configured to provide visual feedback from the second indicator assembly during a first range of motion of the first member,
   wherein the display is not configured to provide visual feedback from the first indicator assembly during the first range of motion of the first member,
   wherein the display is configured to provide visual feedback from the first indicator assembly during a second range of motion of the first member.

12. The surgical instrument of claim 1, wherein the first indicator assembly comprises a light, wherein the first indicator assembly is configured to illuminate the light in response to positioning of the first member in relation to the second member indicating that the gap distance is sized to release tissue from between the anvil and the distal surface.

13. The surgical instrument of claim 1, wherein the first member comprises a magnet, wherein the second member comprises a Hall Effect sensor.

14. The surgical instrument of claim 1, wherein the first member comprises a set of teeth, wherein the second member comprises a pawl configured to ratchet along the teeth.

15. The surgical instrument of claim 1, further comprising a manual input feature operable to drive the translating member longitudinally, wherein the first indicator assembly is configured to provide increased resistance to movement of the manual input feature in response to positioning of the first member in relation to the second member indicating that the gap distance is sized to release tissue from between the anvil and the distal surface.

16. A surgical instrument comprising:
   (a) a body;
   (b) a shaft assembly extending distally from the body;
   (c) a stapling head assembly located at the distal end of the shaft assembly, wherein the stapling head assembly comprises a distal surface, wherein the stapling head assembly is operable to drive an annular array of staples through the distal surface;
   (d) an anvil, wherein the anvil is configured to couple with the stapling head assembly;
   (e) an anvil adjustment assembly, wherein the anvil adjustment assembly comprises a translating member, wherein the translating member is operable to translate relative to the body along a longitudinal axis to thereby adjust a gap distance between the anvil and the distal surface of the stapling head assembly;
   (f) a staple compression height indicator assembly configured to indicate a staple compression height based on the gap distance, wherein the staple compression height indicator assembly comprises:
      (i) a bracket configured to actuate with the translating member, and
      (ii) a pivoting arm pivotably coupled with body, wherein the bracket is configured to drive the pivoting arm relative to the body; and
   (g) a tissue release indicator assembly, wherein the tissue release indicator assembly comprises:
      (i) an array of discrete marker elements fixed to the bracket of the compression height indicator assembly,
      (ii) a sensor, wherein the marker elements are configured to successively activate the sensor in response to translation of the translating member, and
      (iii) an indicator, wherein the indicator is configured to provide feedback indicating whether the gap distance is sized to release tissue from between the anvil and the distal surface based on activation of the sensor by the marker elements.

17. A surgical instrument comprising:
   (a) a body;
   (b) a shaft assembly extending distally from the body;
   (c) a stapling head assembly located at the distal end of the shaft assembly, wherein the stapling head assembly comprises a distal surface, wherein the stapling head assembly is operable to transition between an unfired position and a fired position, wherein the stapling head assembly is configured to drive an annular array of staples through the distal surface in the fired position;
   (d) a firing assembly configured to actuate the stapling head assembly, wherein the firing assembly comprises:
      (i) a motor, and
      (ii) a cam member, wherein the motor is configured to rotate the cam member, wherein the cam member is configured to actuate the stapling head assembly in response to rotation of the motor;
   (d) an anvil, wherein the anvil is configured to couple with the stapling head assembly;
   (e) an anvil adjustment assembly, wherein the anvil adjustment assembly comprises a translating member, wherein the translating member is operable to translate relative to the body along a longitudinal axis to thereby adjust a gap distance between the anvil and the distal surface of the stapling head assembly; and
   (f) an indicator assembly comprising a first indicator, wherein the first indicator is configured to transition from a disengaged position to an engaged position in response to the motor rotating the cam member.

18. The surgical instrument of claim 17, wherein the indicator assembly further comprises a second indicator configured to translate with the translating member of the anvil adjustment assembly, wherein the second indicator is configured to interact with the first indicator in the engaged position to provide feedback indicating whether the gap distance is sized to release tissue from between the anvil and the distal surface based on positioning of the first indicator in relation to the second indicator.

19. The surgical instrument of claim 17, wherein the indicator assembly is configured to indicate if the firing assembly has fired the stapling head assembly.

* * * * *